(12) United States Patent
Gong et al.

(10) Patent No.: US 11,021,719 B2
(45) Date of Patent: Jun. 1, 2021

(54) METHODS AND COMPOSITIONS FOR ASSESSING CRISPER/CAS-MEDIATED DISRUPTION OR EXCISION AND CRISPR/CAS-INDUCED RECOMBINATION WITH AN EXOGENOUS DONOR NUCLEIC ACID IN VIVO

(71) Applicant: Regeneron Pharmaceuticals, Inc., Tarrytown, NY (US)

(72) Inventors: Guochun Gong, Pleasantville, NY (US); Charleen Hunt, Dumont, NJ (US); Susannah Brydges, Putnam Valley, NY (US); Suzanne Hartford, Putnam Valley, NY (US); David Frendewey, New York, NY (US); Brian Zambrowicz, Sleepy Hollow, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 134 days.

(21) Appl. No.: 16/050,806

(22) Filed: Jul. 31, 2018

(65) Prior Publication Data
US 2019/0032092 A1 Jan. 31, 2019

Related U.S. Application Data

(60) Provisional application No. 62/539,279, filed on Jul. 31, 2017.

(51) Int. Cl.
| | |
|---|---|
| *C12N 15/90* | (2006.01) |
| *C12N 15/861* | (2006.01) |
| *C12N 15/877* | (2010.01) |
| *A01K 67/027* | (2006.01) |
| *C12N 9/38* | (2006.01) |

(52) U.S. Cl.
CPC ........ *C12N 15/907* (2013.01); *A01K 67/0275* (2013.01); *C12N 9/2471* (2013.01); *C12N 15/861* (2013.01); *C12N 15/8775* (2013.01); *A01K 2217/07* (2013.01); *A01K 2217/206* (2013.01); *A01K 2227/105* (2013.01); *A01K 2267/0393* (2013.01); *C12N 2310/20* (2017.05); *C12N 2320/11* (2013.01); *C12Y 302/01023* (2013.01)

(58) Field of Classification Search
CPC .................................................. C12N 15/907
See application file for complete search history.

(56) References Cited

U.S. PATENT DOCUMENTS

| | | | |
|---|---|---|---|
| 5,942,435 A | 8/1999 | Wheeler | |
| 6,232,524 B1 | 5/2001 | Tischfield et al. | |
| 6,586,251 B2 | 7/2003 | Economides et al. | |
| 7,294,754 B2 | 11/2007 | Poueymirou et al. | |
| 7,576,259 B2 | 8/2009 | Poueymirou et al. | |
| 7,659,442 B2 | 2/2010 | Poueymirou et al. | |
| 10,329,582 B2 | 6/2019 | Lee et al. | |
| 10,385,359 B2 | 8/2019 | Lee et al. | |
| 10,577,630 B2 | 3/2020 | Zhang et al. | |
| 2008/0078000 A1 | 3/2008 | Poueymirou et al. | |
| 2014/0178879 A1 | 6/2014 | Economides et al. | |
| 2014/0235933 A1 | 8/2014 | Lee et al. | |
| 2014/0273037 A1 | 9/2014 | Wu | |
| 2014/0273226 A1 | 9/2014 | Wu | |
| 2014/0310828 A1 | 10/2014 | Lee et al. | |
| 2015/0376628 A1 | 12/2015 | Schoenherr et al. | |
| 2015/0376651 A1 | 12/2015 | Frendewey et al. | |
| 2016/0145646 A1 | 5/2016 | Frendewey et al. | |
| 2016/0208319 A1 | 7/2016 | Berman et al. | |
| 2016/0304846 A1 | 10/2016 | Liu et al. | |

(Continued)

FOREIGN PATENT DOCUMENTS

| | | |
|---|---|---|
| CN | 105647968 A | 6/2016 |
| EP | 2966170 A1 | 1/2016 |

(Continued)

OTHER PUBLICATIONS

Garcia-Arocena D. (2014, The Jackson Laboratory, Same Mutation, Different Phenotype?) (Year: 2014).*
Heimain-Patterson et al. (2011, Amyotrophic Lateral Schlerosis, vol. 00, pp. 1-8) (Year: 2011).*
2004, Barthold S., Genetica, vol. 122, pp. 75-88, see p. 85 col. 2 parag. 2 lines 1-13 (Year: 2004).*
Wang et al., 2016, Molecular Therapy-Nucleic Acids, vol. 5, pp. 1-12 (Year: 2016).*
Bi et al. (2016, Scientific Reports, vol. 6, pp. 1-12) (Year: 2016).*

(Continued)

*Primary Examiner* — Thaian N. Ton
*Assistant Examiner* — David A. Montanari
(74) *Attorney, Agent, or Firm* — Yongjin Choi; Alston & Bird LLP

(57) ABSTRACT

Methods and compositions are provided for assessing CRISPR/Cas-mediated non-homologous end joining (NHEJ) activity and/or CRISPR/Cas-induced recombination of a target genomic locus with an exogenous donor nucleic acid in vivo or ex vivo. The methods and compositions employ non-human animals comprising a CRISPR reporter such as a genomically integrated CRISPR reporter for detecting and measuring targeted excision of a sequence between two CRISPR/Cas nuclease cleavage sites or disruption of a sequence near a CRISPR/Cas nuclease cleavage site and/or measuring CRISPR/Cas-induced recombination of the CRISPR reporter with an exogenous donor nucleic acid to convert the coding sequence for a first reporter protein to the coding sequence for a different second reporter protein. Methods and compositions are also provided for making and using these non-human animals.

30 Claims, 13 Drawing Sheets
(8 of 13 Drawing Sheet(s) Filed in Color)
Specification includes a Sequence Listing.

(56) References Cited

U.S. PATENT DOCUMENTS

| | | |
|---|---|---|
| 2016/0326548 A1 | 11/2016 | Cost |
| 2017/0107536 A1 | 4/2017 | Zhang et al. |
| 2017/0145405 A1 | 5/2017 | Tang et al. |
| 2017/0198302 A1 | 7/2017 | Feng et al. |
| 2018/0010134 A1 | 1/2018 | Sharp et al. |
| 2018/0110877 A1 | 4/2018 | Wilson et al. |
| 2018/0179553 A1 | 6/2018 | Watson et al. |
| 2018/0179601 A1 | 6/2018 | Alexandrov et al. |
| 2018/0185516 A1 | 7/2018 | Ansell et al. |
| 2019/0002869 A1 | 1/2019 | Yin et al. |
| 2019/0017055 A1 | 1/2019 | Harris |
| 2019/0024074 A1 | 1/2019 | Maresca et al. |
| 2019/0032156 A1 | 1/2019 | Gong et al. |
| 2019/0365924 A1 | 12/2019 | Conway et al. |
| 2019/0390195 A1 | 12/2019 | Tondera et al. |

FOREIGN PATENT DOCUMENTS

| | | |
|---|---|---|
| EP | 3450570 A1 | 3/2019 |
| EP | 3620524 A1 | 3/2020 |
| EP | 3011035 B1 | 5/2020 |
| WO | WO 2008/133938 A2 | 11/2008 |
| WO | WO 2013/176772 A1 | 11/2013 |
| WO | WO 2014/065596 A1 | 5/2014 |
| WO | WO 2014/099744 A1 | 6/2014 |
| WO | WO 2014/130706 A1 | 8/2014 |
| WO | WO 2014/172489 A2 | 10/2014 |
| WO | WO 2014/190181 A1 | 11/2014 |
| WO | WO 2015/007194 A1 | 1/2015 |
| WO | WO 2015/042557 A1 | 3/2015 |
| WO | WO 2015/088643 A1 | 6/2015 |
| WO | WO 2015/089406 A1 | 6/2015 |
| WO | WO 2015/131101 A1 | 9/2015 |
| WO | WO 2015/179540 A1 | 11/2015 |
| WO | WO 2015/200334 A1 | 12/2015 |
| WO | WO 2015/200805 A2 | 12/2015 |
| WO | WO 2016/010840 A1 | 1/2016 |
| WO | WO 2016/044745 A1 | 3/2016 |
| WO | WO 2016/070037 A2 | 5/2016 |
| WO | WO 2016/073990 A2 | 5/2016 |
| WO | WO 2016/081923 A2 | 5/2016 |
| WO | WO 2016/089866 A1 | 6/2016 |
| WO | WO 2016/115326 A1 | 7/2016 |
| WO | WO 2016/123514 A1 | 8/2016 |
| WO | WO 2016/132122 A1 | 8/2016 |
| WO | WO 2016/137949 A1 | 9/2016 |
| WO | WO 2016/176191 A1 | 11/2016 |
| WO | WO 2017/087780 A1 | 5/2017 |
| WO | WO 2017/122096 A1 | 7/2017 |
| WO | WO 2017/173054 A1 | 10/2017 |
| WO | WO 2017/186718 A1 | 11/2017 |
| WO | WO 2018/107026 A1 | 6/2018 |
| WO | WO 2018/107028 A1 | 6/2018 |
| WO | WO 20118/213353 A1 | 11/2018 |
| WO | WO 2019/028023 A1 | 2/2019 |
| WO | WO 2019/028029 A1 | 2/2019 |
| WO | WO 2019/089761 A1 | 5/2019 |
| WO | WO 2019/089803 A1 | 5/2019 |
| WO | WO 2019/204767 A1 | 10/2019 |
| WO | WO 2019/237069 A1 | 12/2019 |
| WO | WO 2019/246203 A1 | 12/2019 |
| WO | WO 2020/047531 A1 | 3/2020 |
| WO | WO 2020/146732 A1 | 7/2020 |

OTHER PUBLICATIONS

Brevini et al., 2010, Theriogenology, vol. 74, pp. 544-550 (Year: 2010).*

Paris et al. (2010, Theriogenology, vol. 74, pp. 516-524) (Year: 2010).*

Munozetal. (2008, Theriogenology, vol. 69, pp. 1159-1164) (Year: 2008).*

Gomez et al. (2010, Theriogenology, vol. 74, pp. 498-515) (Year: 2010).*

Butaetal. (2013, Stem Cell Res., vol. 11, pp. 552-562) (Year: 2013).*

Tong et al. (2010, Nature, vol. 467(7312), pp. 211-213) (Year: 2010).*

Hong et al. (2012, Stem Cells and Development, vol. 21(9), pp. 1571-1586) (Year: 2012).*

Barthold, "Genetically altered mice: phenotypes, no phenotypes, and Faux phenotypes," Genetica, 122(1):75-88, (2004).

Bilsland, et al., "Properties of a Telomerase-Specific Cre/Lox Switch for Transcriptionally Targeted Cancer Gene Therapy," Neoplasia, 7(11):1020-1029, (2005).

Birling, et al., "Modeling human disease in rodents by CRISPR/Cas9 genome editing," Mamm. Genome, 28(7-8):291-301, (2017).

Brevini, et al., "No shortcuts to pig embryonic stem cells," Theriogenology, 74(4):544-550, (2010).

Cao, et al., "Isolation and Culture of Primary Bovine Embryonic Stem Cell Colonies by a Novel Method," J. Exp. Zool. A. Ecol. Genet. Physiol., 311(5):368-376, (2009).

Clark, et al., "A future for transgenic livestock," Nat. Rev. Genet., 4(10):825-833, (2003).

Dechiara, T.M., et al., "VelociMouse: Fully ES Cell-Derived F0-Generation Mice Obtained from the Injection of ES Cells into Eight-Cell-Stage Embryos," Jan. 1, 2009, Methods in Molecular Biology, 530(16): 311-324.

Dennis, "Welfare Issues of Genetically Modified Animals," ILAR J., 43(2):100-109, (2002).

Frendewey, et al., "The Loss-of-Allele Assay for ES Cell Screening and Mouse Genotyping," Methods Enzymol., 476:295-307, (2010).

Genoway, "Humanized Mouse Model," retrieved from https://www.genoway.com/services/customized-mouse/knockin-models/humanisation.htm on May 12, 2018.

Gomez, et al., "Derivation of cat embryonic stem-like cells from in vitro-produced blastocysts on homologous and heterologous feeder cells," Theriogenology, 74(4): 498-515, (2010).

Graham, et al., "Resources for the design of CRISPR gene editing experiments," Genome Biol., 16:260, (2015).

Harari, et al., "Bridging the Species Divide: Transgenic Mice Humanized for Type-I Interferon Response," PLoS ONE, 9(1): e84259, (2014).

Houdebine, "Methods to Generate Transgenic Animals," pp. 31-48 in "Genetic Engineering in Livestock: New Applications and Interdisciplinary Perspectives," Ed. Engelhard et al., (2009).

Ishikawa, et al., "Conditional Bicistronic Cre Reporter Line Expressing Both Firefly Luciferase and β-glactosidase," Mol. Imaging Biol., 13(2):284-292, (2011).

Jean, et al., "Pluripotent genes in avian stem cells," Dev. Growth Differ., 55(1): 41-51, (2013).

Liu, et al., "Biallelic insertion of a transcriptional terminator via the CRISPR/Cas9 system efficiently silences expression of protein-coding and non-coding RNA genes," J. Biol. Chem., 292(14):5624-5633, (Apr. 7, 2017).

Munoz, et al., "Conventional pluripotency markers are unspecific for bovine embryonic-derived cell-lines," Theriogenology, 69(9): 1159-1164, (2008).

Niemann, "Transgenic farm animals get off the ground. Transgenic Animals in Agriculture, Conference Tahoe City, California, USA. Aug. 24-27, 1997." Transgenic Res., 7(1): 73-75, (1998).

Paix et al., "Precision genome editing using CRISPR-Cas9 and linear repair templates in C. elegans," Methods, 121-122:86-93, (2017).

Paris, et al., "Equine embryos and embryonic stem cells: defining reliable markers of pluripotency," Theriogenology, 74(4): 516-524, (2010).

Poueymirou, et al., "F0 generation mice fully derived from gene-targeted embryonic stem cells allowing immediate phenotypic analyses," Nat. Biotechnol., 25(1):91-99, (2007).

Stoller, et al., "Cre Reporter Mouse Expressing a Nuclear Localized Fusion of GFP and β-Glactosidase Reveals New Derivatives of Pax3-Expressing Precursors," Genesis, 46(4):200-204, (2008).

Wakchaure, et al., "Transgenic Animals: A Review on its Various Dimensions and Applications in Animal Biotechnology," International Journal of Emerging Technology and Advanced Engineering, 5(11):210-213, (2015).

(56) References Cited

OTHER PUBLICATIONS

Yamamoto, et al., "A Multifunctional Reporter Mouse Line for Cre- and FLP-Dependent Lineage Analysis," Genesis, 47(2):107-114, (2009).
Zhang et al., "Optimization of genome editing through CRISPR-Cas9 engineering," Bioengineered, 7(3):166-174, (2016).
Zhou, et al., "Developing tTA transgenic rats for inducible and reversible gene expression," Int. J. Biol. Sci., 5(2):171-181, (2009).
WIPO Application No. PCT/US2018/044606, PCT International Search Report and Written Opinion of the International Searching Authority dated Mar. 14, 2019.
WIPO Application No. PCT/US2018/044606, PCT Invitation to Pay Additional Fees dated Dec. 6, 2018.
Anderson, et al., "Systemic analysis of CRISPR-Cas9 mismatch tolerance reveals low levels of off-target activity," Journal of Biotechnology, 211:56-65, (2015).
Bikard et al., "Programmable repression and activation of bacterial gene expression using an engineered CRISPR-Cas system," Nucleic Acids Research, 41(15):7429-7437, (2013).
Chavez, et al., "Comparison of Cas9 activators in multiple species," Nature Methods, Advance Online Publication, 5 pages plus Online Methods, (2016).
Cheng, et al., "Multiplexed activation of endogenous genes by CRISPR-on, an RNA-guided transcriptional activator system," Cell Research, 23(10):1163-1171, (2013).
Chow et al., "AAV-mediated direct in vivo CRISPR screen identifies functional suppressors in glioblastoma," Nat. Neurosci. 20(10):1329-1341 plus supplementary materials, (Aug. 14, 2017).
Chu, et al., "Increasing the efficiency of homology-directed repair for CRISPR-Cas9-induced precise gene editing in mammalian cells," Nature Biotechnology, 33(5):543-551, (2015).
Doyle, et al., "The Construction of Transgenic and Gene Knockout/Knockin Mouse Models of Human Disease," Transgenic Res., 21(2):327-349, (2012).
Finn, et al., "A Single Administration of CRISPR/Cas9 Lipid Nanoparticles Achieves Robust and Persistent In Vivo Genome Editing," Cell Reports, 22:1-9, (Feb. 27, 2018).
Flemr, et al., "Single-Step Generation of Conditional Knockout Mouse Embryonic Stem Cells," Cell Reports, 12:709-716, (2015).
Frock, et al., "Genome-wide detection of DNA double-stranded breaks induced by engineered nucleases," Nat. Biotech., 33(2):179-186, (2015).
Fujihara, et al., "CRISPR/Cas9-Based Genome Editing in Mice by Single Plasmid Injection," Methods in Enzymology, vol. 546, Chapter 15, pp. 319-336, (2014).
Gilles, et al., "Efficient CRISPR-mediated gene targeting and transgene replacement in the beetle Tribolium castaneum," Development, 142:2832-2839 plus supplementary material, (2015).
Glaser, et al., "GFP to BFP Conversion: A Versatile Assay for Genome Editing," Molecular Therapy—Nucleic Acids, 5:e334 (4 pages), (2016).
Gori, et al., "Delivery and Specificity of CRISPR/Cas9 Genome Editing Technologies for Human Gene Therapy," Human Gene Therapy, 26(7):443-451, (2015).
Haapaniemi et al., "CRISPR-Cas9 genome induces a p53-mediated DNA damage response," Nat. Med. doi: 10.1038/s41591-018-0049-z, (Jun. 11, 2018, epub ahead of print).
Harrison, et al., "A CRISPR view of development," Genes & Development, 28:1859-1872, (2014).
He, et al., "Knock-in of large reporter genes in human cells via CRISPR/Cas9-induced homology-dependent and independent DNA repair," Nucleic Acids Research, pp. 1-14, (2016).
Heckl, et al., "Generation of mouse models of myeloid malignancy with combinatorial genetic lesions using CRISPR-Cas9 genome editing," Nat. Biotechnol., 32(9):941-946, (2014).
Hung, et al., "AAV-Mediated CRISPR/Cas Gene Editing of Retinal Cells in Vivo," Invest. Opthalmol. Vis. Sci., 57:3470-3476, (2016).
Ihry et al., "p53 inhibits CRISPR-Cas9 engineering in human pluripotent stem cells," Nat. Med. doi: 10.1038/s41591-018-0050-6 (Jun. 11, 2018, epub ahead of print).

Jo, et al., "CRISPR/Cas9 system as in innovative genetic engineering tool: Enhancements in sequence specificity and delivery methods," Biochimica et Biophysica Acta, 1856:234-243, (2015).
Juers, et al., "LacZ β-galactosidase: Structure and function of an enzyme of historial and molecular biological importance," Protein Science, 21:1792-1807, (2012).
Kamimura, et al., "Image-Guided Hydrodynamic Gene Delivery: Current Status and Future Directions," Pharmaceutics, 7:213-233, (2015).
Kim, et al., "In vivo genome editing with a small Cas9 orthologue derived from Campylobacter jejuni," Nature Communications, 12 pages (2017).
Kleinstiver, et al., "High-fidelity CRISPR-Cas9 nucleases with no detectable genome-wide off-target effects," Nature, 529:490-495 plus supporting materials, (2016).
Koo, et al., "Measuring and Reducing Off-Target Activities of Programmable Nucleases Including CRISPR-Cas9," Mol. Cells, 38(6):475-481, (2015).
Kosicki et al., "Repair of double-strand breaks induced by CRISPR-Cas9 leads to large deletions and complex rearrangments," Nat. Biotechnol., 36(8):765-771, (Jul. 16, 2018).
Kuhar, et al., "Novel fluorescent genome editing reporters for monitoring DNA repair pathway utilization at endonuclease-indued breaks," Nucleic Acids Research, 11 pages, (2013).
Li, et al., "A versatile reporter system for CRISPR-mediated chromosomal rearrangements," Genome Biology, 16:111, 11 pages (2015).
Madisen, et al., "A robust and high-throughput Cre reporting and characterization system for the whole mouse brain," Nat. Neurosci., 13(1):133-140, (2010).
Maresch, et al., "Multiplexed pancreatic genome engineering and cancer induction by transfection-based CRISPR/Cas9 delivery in mice," Nature Communications, 7:10770, 13 pages, (2016).
Mashiko, et al., "Feasibility for a large scale mouse mutagenesis by injecting CRISPR/Cas plasmid into zygotes." Develop. Growth Differ., 56:122-129, (2014).
Mou, et al., "Precision cancer mouse models through genome editing with CRISPR-Cas9," Genome Medicine, 7:53, 11 pages, (2015).
Osborn, et al., "Fanconi Anemia Gene Editing by the CRISPR/Cas9 System," Human Gene Therapy, 26:114-126, (2015).
Parnas, et al., "A Genome-wide CRISPR Screen in Primary Immune Cells to Dissect Regulatory Networks," Cell, 162:675-686, (2015).
Platt, et al., "CRISPR-Cas9 Knockin Mice for Genome Editing and Cancer Modeling," Cell, 159:440-455, (2014).
Qi, et al., "Repurposing CRISPR as an RNA-Guided Platform for Sequence-Specific Control of Gene Expression," Cell, 152:1173-1183, (2013).
Ramakrishna, et al., "Surrogate reporter-based enrichment of cells containing RNA-guided Cas9 nuclease-induced mutations," Nature Communications, 5:3378, 10 pages, (2014).
Richardson, et al., "Enhancing homology-directed genome editing by catalytically active and inactive CRISPR-Cas9 using asymmetric donor DNA," Nature Biotechnology, 34(3):339-344 plus online methods, (2016).
Ropp, et al., "Aequorea Green Fluorescent Protein: Simultaneous Analysis of Wild-Type and Blue-Fluorescing Mutant by Flow Cytometry," Cytometry, 24:284-288, (1996).
Sakurai, et al., "A single blastocyst assay optimized for detecting CRISPR/Cas9 system-induced indel mutations in mice," BMC Biotechnology, 14:69, 11 pages, (2014).
Shen, et al., "Generation of gene-modified mice via Cas9/RNA-mediated gene targeting," Cell Research, 23:720-723, (2013).
Slaymaker, et al., "Rationally engineered Cas9 nucleases with improved specificity," Science, 351(6268):84-88 plus Supplementary Materials, (2015).
Steyer, et al., "High content analysis platform for optimization of lipid mediated CRISPR-Cas9 delivery strategies in human cells," Acta Biomater., 34:143-158, (2016).
Suzuki, et al., "In vivo genome editing via CRISPR/Cas9 mediated homology-independent targeted integration," Nature, 540:144-149 plus supporting materials, (2016).

(56) References Cited

OTHER PUBLICATIONS

Swiech, et al., "In vivo interrogation of gene function in the mammalian brain using CRISPR-Cas9," Nat. Biotechnol., 33(1):102-106, (2015).
Tabebordbar, et al., "In vivo gene editing in dystrophic mouse muscle and muscle stem cells," Science, 10.1126/science.aad5117, 9 pages, (2015).
Vouillot, et al., "Comparison of T7E1 and Surveyor Mismatch Cleavage Assays to Detect Mutations Triggered by Engineered Nucleases," G3 (Genes, Genomes, Genetics), 5:407-415, (2015).
Wang et al., "Mapping a functional cancer genome atlas of tumor suppressors in mouse liver using AAV-CRISPR-mediated direct in vivo screening," Sci. Adv. 4(2):eaao5508, (Feb. 28, 2018).
Wang, et al., "In Vivo Delivery Systems for Therapeutic Genome Editing," Int. J. Mol. Sci., 17:626, 19 pages, (2016).
Wu, et al., "Correction of Genetic Disease in Mouse via Use of CRISPR-Cas9," Cell, 13:659-652, (2013).
Yang, et al., "Highly Effcient and Rapid Detection of the Cleavage Activity of Cas9/gRNA via a Fluorescent Reporter," Appl. Biochem. Biotechnol., 13 pages, published online May 21, 2016.
Yang, et al., "One-Step Generation of Mice Carrying Reporter and Conditional Alleles by CRISPR/Cas-Mediated Genome Engineering," Cell, 154:1370-1379, (2013).
Yin, et al., "Functional screening of guide RNAs targeting the regulatory and structural HIV-1 viral genome for a cure of AIDS," AIDS, 30(8):1163-1174, (2016).
Yin, et al., "Genome editing with Cas9 in adult mice corrects a disease mutation and phenotype," Nat. Biotechnol., 32(6):551-553, (2014).
Zalatin, et al., "Engineering Complex Synthetic Transcriptional Programs with CRISPR RNA Scaffolds," Cell, 160:339-350, (2015).
Zhang, et al., "Comparison of non-canonical PAMs for CRISPR/Cas9-mediated DNA cleavage in human cells," Scientific Reports, 4:5405, 5 pages, (2014).
Zou, et al., "Site-specific gene correction of a point mutation in human iPS cells derived from an adult patient with sickle cell disease," Blood, 118(17):4599-4608, (2011).
Brevini, et al., "Porcine embryonic stem cells: Facts, challenges and hopes," Theriogenology, 68 suppl. 1:S206-S213, (2007).
Burova, et al., "Characterization of the Anti-PD-1 Antibody REGN2810 and Its Antitumor Activity in Human PD-1 Knock-In Mice," Mol. Cancer Ther., 16(5):861-870, (2017).
Herndler-Brandstetter, et al., "Humanized mouse model supports development, function, and tissue residency of human natural killer cells," Proc. Natl. Acad. Sci. U.S.A., 114(45):E9626-E9634, (2017).
Kawamata, et al., "Generaion of genetically modified rats from embryonic stem cells," Proc. Natl. Acad. Sci. U.S.A., 7(32)14223-14228, (2010).
Kumar, et al., "Transgenic Mouse Technology: Principles and Methods," Methods Mol. Biol., 590:335-362, (2009).
Lute, et al., "Human CTLA4 knock-in mice unravel the quantitative link between tumor immunity and autoimmunity induced by anti-CTLA-4 antibodies," Blood, 106(9):3127-3133, (2005).
Mullins, et al., "Transgenesis in the rat and larger mammals," J. Clin. Invest. 97(7):1557-1560, (1996).
Rezza, et al., "Unexpected genomic rearrangements at targeted loci associated with CRISPR/Cas9-mediated knock-in," Sci. Rep., 9(1):3486, (2019).
Ristevski, "Making better transgenic models: conditional, temporal, and spatial approaches," Mol. Biotechnol., 29(2):153-163, (2005).
Rogers, et al., "Disruption of the CFTR Gene Produces a Model of Cystic Fibrosis in Newborn Pigs," Science, 321(5897):1837-1841, (2008).
Sigmund, "Viewpoint: Are Studies in Genetically Altered Mice Out of Control?," Arterioscler. Thromb. Vasc. Biol., 20(6):1425-1429, (2000).
Valenzuela, et al., "High-throughput engineering of the mouse genome coupled with high-resolution expression analysis," Nat. Biotechnol., 21(6):652-659, (2003).
Zhao, et al., "Inconsistency between hepatic expression and serum concentration of transthyretin in mice humanized at the transthyretin locus," Genes to Cells, 13:1257-1268, (2008).

\* cited by examiner

Untreated

Cre Plasmid

Cas9 + Pgk Poly(A) Excision sgRNAs gU2 and gD1

Cas9 + Pgk Poly(A) Excision sgRNAs gU3 and gD2

Cas9 + Pgk Poly(A) Excision sgRNAs gU3 and gD1

METHODS AND COMPOSITIONS FOR ASSESSING CRISPER/CAS-MEDIATED DISRUPTION OR EXCISION AND CRISPR/CAS-INDUCED RECOMBINATION WITH AN EXOGENOUS DONOR NUCLEIC ACID IN VIVO

CROSS-REFERENCE TO RELATED APPLICATIONS

This application claims the benefit of U.S. Application No. 62/539,279, filed Jul. 31, 2017, which is herein incorporated by reference in its entirety for all purposes.

REFERENCE TO A SEQUENCE LISTING SUBMITTED AS A TEXT FILE VIA EFS WEB

The Sequence Listing written in file 516575SEQLIST.txt is 72.7 kilobytes, was created on Jul. 31, 2018, and is hereby incorporated by reference.

BACKGROUND

CRISPR/Cas technology is a promising new therapeutic modality. However, there is a need for better means of assessing the efficiency of mutation generation or targeted gene modification by an introduced CRISPR/Cas agent in vivo. Assessing such activity in vivo currently relies on difficult molecular assays, such as single-strand DNase sensitivity assays, digital PCR, or next generation sequencing. Better methods and tools are needed to more effectively assess the activity of introduced CRISPR/Cas agents and to assess different delivery methods and parameters for targeting specific tissues or cell types in vivo.

SUMMARY

Methods and compositions are provided for assessing CRISPR/Cas-mediated non-homologous end joining activity and/or CRISPR/Cas-induced recombination activity in vivo. In one aspect, provided are non-human animals comprising a CRISPR reporter for assessing CRISPR/Cas-induced excision of a nucleic acid between first and second guide RNA target sequences, wherein the CRISPR reporter is integrated at a target genomic locus and comprises a first polyadenylation signal flanked by the first and second guide RNA target sequences followed by a reporter cassette comprising a coding sequence for a first reporter protein and a coding sequence for a second reporter protein in any order, wherein the first reporter protein and the second reporter protein are different.

In some such non-human animals, the CRISPR reporter is also for assessing CRISPR/Cas-induced recombination of the CRISPR reporter with an exogenous donor nucleic acid. Optionally, the first reporter protein comprises a third guide RNA target sequence, wherein recombination of the CRISPR reporter with the exogenous donor nucleic acid changes the coding sequence for the first reporter protein into a coding sequence for a third reporter protein. Optionally, the coding sequence for the first reporter protein is changed into the coding sequence for the third reporter protein by changing a single codon. Optionally, the third guide RNA target sequence overlaps with the portion of the coding sequence for the first reporter protein modified by the exogenous donor nucleic acid.

In some such non-human animals, one of the first and second reporter proteins comprises a fluorescent reporter protein. Optionally, the fluorescent reporter protein comprises an enhanced green fluorescent protein (eGFP) or an enhanced blue fluorescent protein (eBFP). Optionally, the first and second reporter proteins comprise a fluorescent reporter protein and a non-fluorescent reporter protein. Optionally, the fluorescent reporter protein can be detected in a flow cytometry assay, and the non-fluorescent protein can be detected in a histochemical assay. In some such non-human animals, one of the first and second reporter proteins comprises a beta-galactosidase protein.

In some such non-human animals, the first polyadenylation signal is also flanked by recombinase recognition sites for a first recombinase. Optionally, the recombinase recognition sites for the first recombinase are loxP sequences.

In some such non-human animals, the reporter cassette comprises a multicistronic nucleic acid comprising the coding sequence for the first reporter protein and the coding sequence for the second reporter protein separated by an intervening internal ribosome entry site (IRES) or an intervening 2A peptide coding sequence. Optionally, the multicistronic nucleic acid comprises a beta-galactosidase coding sequence and an enhanced blue fluorescent protein (eBFP) coding sequence or an enhanced green fluorescent protein (eGFP) coding sequence separated by an intervening P2A peptide coding sequence.

In some such non-human animals, the CRISPR reporter is operably linked to an endogenous promoter at the target genomic locus.

In some such non-human animals, the 5' end of the CRISPR reporter further comprises a 3' splicing sequence.

In some such non-human animals, the CRISPR reporter does not comprise a selection cassette. In some such non-human animals, the CRISPR reporter further comprises a selection cassette. Optionally, the selection cassette is flanked by recombinase recognition sites for a second recombinase. Optionally, the selection cassette comprises a drug resistance gene.

In some such non-human animals, the distance between the first guide RNA target sequence and the second guide RNA target sequence is less than about 500 base pairs.

In some such non-human animals, the first guide RNA target sequence and the second guide RNA target sequence are identical, and each comprises SEQ ID NO: 41.

In some such non-human animals, the non-human animal is a rat or mouse. Optionally, the non-human animal is a mouse.

In some such non-human animals, the target genomic locus is a safe harbor locus. Optionally, the safe harbor locus is a Rosa26 locus. Optionally, the CRISPR reporter is inserted into the first intron of the Rosa26 locus.

In some such non-human animals, the non-human animal is a mouse, the target genomic locus is the Rosa26 locus, and the CRISPR reporter is operably linked to the endogenous Rosa26 promoter, is inserted into the first intron of the Rosa26 locus, and comprises from 5' to 3': (a) a 3' splicing sequence; (b) a first polyadenylation signal flanked by: (i) first and second loxP sites; and (ii) first and second guide RNA target sequences, wherein the first guide RNA target sequence and the second guide RNA target sequence are identical, and each comprises SEQ ID NO: 41, 43, 44, 45, 46, or 47; and (c) a reporter cassette, comprising from 5' to 3': (i) a beta-galactosidase coding sequence; (ii) a P2A coding sequence; (iii) an enhanced blue fluorescent protein (eBFP) coding sequence, wherein the eBFP coding sequence comprises a third guide RNA target sequence comprising SEQ ID NO: 42; and (iv) a second polyadenylation signal, wherein the first polyadenylation signal and the second polyadenylation signal are different. Optionally, the CRISPR reporter further comprises: (d) a selection cassette 3' of the reporter cassette, wherein the selection cassette is flanked by FRT sites and comprises from 5' to 3': (i) a neomycin phosphotransferase coding sequence operably linked to a human ubiquitin promoter; and (ii) a third polyadenylation signal.

In some such non-human animals, the non-human animal is heterozygous for the CRISPR reporter at the target genomic locus. In some such non-human animals, the non-human animal is homozygous for the CRISPR reporter at the target genomic locus.

In another aspect, provided are methods of testing the ability of a CRISPR/Cas nuclease to excise a genomic nucleic acid in vivo. Some such methods comprise: (a) introducing into any of the above non-human animals: (i) a first guide RNA designed to hybridize to the first guide RNA target sequence in the CRISPR reporter; (ii) a second guide RNA designed to hybridize to the second guide RNA target sequence in the CRISPR reporter; and (iii) a Cas protein; and (b) measuring the activity or expression of at least one of the first and second reporter proteins.

In some such methods, the Cas protein is a Cas9 protein. In some such methods, the Cas protein is introduced into the non-human animal in the form of a protein. In some such methods, the Cas protein is introduced into the non-human animal in the form of a messenger RNA encoding the Cas protein. In some such methods, the Cas protein is introduced into the non-human animal in the form of a DNA encoding the Cas protein, wherein the DNA is operably linked to a promoter active in one or more cell types in the non-human animal.

In some such methods, the first guide RNA and the second guide RNA are identical, and each comprises the sequence set forth in SEQ ID NO: 2.

In some such methods, the reporter protein measured in step (b) is a fluorescent reporter protein, and step (b) comprises a flow cytometry assay. In some such methods, the reporter protein measured in step (b) is a beta-galactosidase protein, and step (b) comprises a histochemical staining assay.

In some such methods, the guide RNAs in step (a) are introduced in the form of RNA. In some such methods, the guide RNAs in step (a) are each introduced into the non-human animal in the form of a DNA encoding the guide RNA, wherein the DNA is operably linked to a promoter active in one or more cell types in the non-human animal.

In some such methods, the introducing comprises adeno-associated virus (AAV)-mediated delivery, lipid nanoparticle-mediated delivery, or hydrodynamic delivery. Optionally, the introducing comprises AAV-mediated delivery. Optionally, the introducing comprises AAV8-mediated delivery, and step (b) comprises measuring activity of the reporter protein in the liver of the non-human animal.

In another aspect, provided are methods of optimizing the ability of a CRISPR/Cas nuclease to excise a genomic nucleic acid in vivo. Some such methods comprise: (I) performing any of the above methods of testing the ability of a CRISPR/Cas nuclease to excise a genomic nucleic acid in vivo a first time in a first non-human animal; (II) changing a variable and performing the method of step (I) a second time with the changed variable in a second non-human animal; and (III) comparing the activity or expression of the reporter protein in step (I) with the activity or expression of the at least one of the reporter protein in step (II), and selecting the method resulting in the higher activity or expression of the reporter protein.

In some such methods, the changed variable in step (II) is the delivery method. In some such methods, the changed variable in step (II) is the delivery method of introducing the guide RNAs and/or the Cas protein into the non-human animal. In some such methods, the changed variable in step (II) is the route of administration. In some such methods, the changed variable in step (II) is the route of administration of introducing the guide RNAs and/or the Cas protein into the non-human animal. In some such methods, the changed variable in step (II) is the concentration or amount of the guide RNAs introduced into the non-human animal. In some such methods, the changed variable in step (II) is the concentration or amount of the guide RNAs and/or the Cas protein introduced into the non-human animal. In some such methods, the changed variable in step (II) is the concentration or amount of the guide RNAs introduced into the non-human animal relative to the concentration or amount of Cas protein introduced into the non-human animal. In some such methods, the changed variable in step (II) is the guide RNAs (e.g., the form of guide RNAs or the sequence of the guide RNAs) introduced into the non-human animal. In some such methods, the changed variable in step (II) is Cas protein (e.g., the form of Cas protein) introduced into the non-human animal.

In another aspect, provided are methods of testing CRISPR/Cas-induced recombination of a genomic nucleic acid with an exogenous donor nucleic acid in vivo. Some such methods comprise: (a) providing any of the above non-human animals, wherein the CRISPR reporter is also for assessing CRISPR/Cas-induced recombination of the CRISPR reporter with an exogenous donor nucleic acid, wherein the first polyadenylation signal has been removed from the CRISPR reporter, and wherein the coding sequence for the first reporter protein comprises a third guide RNA target sequence, and introducing into the non-human animal: (i) a guide RNA designed to hybridize to the third guide RNA target sequence in the CRISPR reporter; (ii) a Cas protein; and (iii) an exogenous donor nucleic acid capable of recombining with the CRISPR reporter and changing the coding sequence for the first reporter protein into a coding sequence for a third reporter protein; and (b) measuring the activity or expression of the third reporter protein.

In some such methods, the Cas protein is a Cas9 protein. In some such methods, the Cas protein is introduced into the non-human animal in the form of a protein. In some such methods, the Cas protein is introduced into the non-human animal in the form of a messenger RNA encoding the Cas protein. In some such methods, the Cas protein is introduced into the non-human animal in the form of a DNA encoding the Cas protein, wherein the DNA is operably linked to a promoter active in one or more cell types in the non-human animal.

In some such methods, the third reporter protein measured in step (b) is a fluorescent reporter protein, and step (b) comprises a flow cytometry assay. In some such methods, the first reporter protein is an enhanced blue fluorescent protein (eBFP), and the third guide RNA comprises the sequence set forth in SEQ ID NO: 14. In some such methods, the first reporter protein is an enhanced blue fluorescent protein (eBFP), and the third reporter protein is an enhanced green fluorescent protein (eGFP).

In some such methods, the exogenous donor nucleic acid comprises the sequence set forth in SEQ ID NO: 15 or SEQ ID NO: 16. In some such methods, the exogenous donor nucleic acid is a single-stranded deoxynucleotide.

In some such methods, the guide RNA in step (a) is introduced in the form of RNA. In some such methods, the guide RNA in step (a) is introduced into the non-human animal in the form of a DNA encoding the guide RNA, wherein the DNA is operably linked to a promoter active in one or more cell types in the non-human animal.

In some such methods, the introducing comprises adeno-associated virus (AAV)-mediated delivery, lipid nanoparticle-mediated delivery, or hydrodynamic delivery. Optionally, the introducing comprises AAV-mediated delivery. Optionally, the introducing comprises AAV8-mediated delivery, and step (b) comprises measuring activity of the reporter protein in the liver of the non-human animal.

In another aspect, provided are methods of optimizing the ability of CRISPR/Cas to induce recombination of a genomic nucleic acid with an exogenous donor nucleic acid in vivo. Some such methods comprise: (I) performing any of the above methods of testing CRISPR/Cas-induced recombination of a genomic nucleic acid with an exogenous donor nucleic acid in vivo a first time in a first non-human animal; (II) changing a variable and performing the method of step (I) a second time with the changed variable in a second non-human animal; and (III) comparing the activity or expression of the third reporter protein in step (I) with the activity or expression of the third reporter protein in step (II), and selecting the method resulting in the higher activity or expression of the third reporter protein.

In some such methods, the changed variable in step (II) is the delivery method. In some such methods, the changed variable in step (II) is the delivery method of introducing one or more of the guide RNA, the Cas protein, and the exogenous donor nucleic acid into the non-human animal. In some such methods, the changed variable in step (II) is the route of administration. In some such methods, the changed variable in step (II) is the route of administration of introducing one or more of the guide RNA, the Cas protein, and the exogenous donor nucleic acid into the non-human animal. In some such methods, the changed variable in step (II) is the concentration or amount of one or more of the guide RNA, the Cas protein, and the exogenous donor nucleic acid introduced into the non-human animal. In some such methods, the changed variable in step (II) is exogenous donor nucleic acid (e.g., the form or sequence of the exogenous donor nucleic acid) introduced into the non-human animal. In some such methods, the changed variable in step (II) is the concentration or amount of the guide RNA introduced into the non-human animal relative to the concentration or amount of Cas protein introduced into the non-human animal. In some such methods, the changed variable in step (II) is the guide RNA (e.g., the form or sequence of the guide RNA) introduced into the non-human animal. In some such methods, the changed variable in step (II) is the Cas protein (e.g., the form or sequence of the Cas protein) introduced into the non-human animal.

BRIEF DESCRIPTION OF THE FIGURES

The patent or application file contains at least one drawing executed in color. Copies of this patent or patent application publication with color drawing(s) will be provided by the Office upon request and payment of the necessary fee.

DEFINITIONS

Figure 1A:
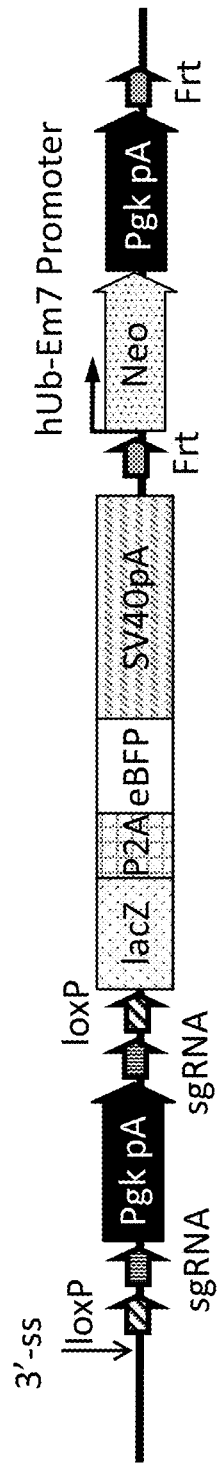
FIG. 1A shows a LSL-LacZ:eBFP CRISPR reporter allele (MAID2634; not to scale), comprising from 5' to 3': a 3' splicing sequence; a first loxP site; a first guide RNA target sequence; a first Pgk polyadenylation signal; a second guide RNA target sequence; a second loxP site; a lacZ gene; a P2A coding sequence; an enhanced blue fluorescent protein (eBFP) coding sequence; an SV40 polyadenylation signal; a first Frt site; human ubiquitin and Em7 promoters operably linked to a neomycin resistance gene coding sequence; a second Pgk polyadenylation signal; and a second Frt site.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The term "genomically integrated" refers to a nucleic acid that has been introduced into a cell such that the nucleotide sequence integrates into the genome of the cell. Any protocol may be used for the stable incorporation of a nucleic acid into the genome of a cell.

The term "expression vector" or "expression construct" refers to a recombinant nucleic acid containing a desired coding sequence operably linked to appropriate nucleic acid sequences necessary for the expression of the operably linked coding sequence in a particular host cell or organism. Nucleic acid sequences necessary for expression in prokaryotes usually include a promoter, an operator (optional), and a ribosome binding site, as well as other sequences. Eukaryotic cells are generally known to utilize promoters, enhancers, and termination and polyadenylation signals, although some elements may be deleted and other elements added without sacrificing the necessary expression.

The term "targeting vector" refers to a recombinant nucleic acid that can be introduced by homologous recombination, non-homologous-end-joining-mediated ligation, or any other means of recombination to a target position in the genome of a cell.

The term "viral vector" refers to a recombinant nucleic acid that includes at least one element of viral origin and includes elements sufficient for or permissive of packaging into a viral vector particle. The vector and/or particle can be utilized for the purpose of transferring DNA, RNA, or other nucleic acids into cells either ex vivo or in vivo. Numerous forms of viral vectors are known.

The term "isolated" with respect to proteins, nucleic acids, and cells includes proteins, nucleic acids, and cells that are relatively purified with respect to other cellular or organism components that may normally be present in situ, up to and including a substantially pure preparation of the protein, nucleic acid, or cell. The term "isolated" also includes proteins and nucleic acids that have no naturally occurring counterpart or proteins or nucleic acids that have been chemically synthesized and are thus substantially uncontaminated by other proteins or nucleic acids. The term "isolated" also includes proteins, nucleic acids, or cells that have been separated or purified from most other cellular components or organism components with which they are naturally accompanied (e.g., other cellular proteins, nucleic acids, or cellular or extracellular components).

The term "wild type" includes entities having a structure and/or activity as found in a normal (as contrasted with mutant, diseased, altered, or so forth) state or context. Wild type genes and polypeptides often exist in multiple different forms (e.g., alleles).

The term "endogenous sequence" refers to a nucleic acid sequence that occurs naturally within a cell or non-human animal. For example, an endogenous Rosa26 sequence of a non-human animal refers to a native Rosa26 sequence that naturally occurs at the Rosa26 locus in the non-human animal.

"Exogenous" molecules or sequences include molecules or sequences that are not normally present in a cell in that form. Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form in a particular cell at a particular developmental stage under particular environmental conditions.

The term "heterologous" when used in the context of a nucleic acid or a protein indicates that the nucleic acid or protein comprises at least two segments that do not naturally occur together in the same molecule. For example, the term "heterologous," when used with reference to segments of a nucleic acid or segments of a protein, indicates that the nucleic acid or protein comprises two or more sub-sequences that are not found in the same relationship to each other (e.g., joined together) in nature. As one example, a "heterologous" region of a nucleic acid vector is a segment of nucleic acid within or attached to another nucleic acid molecule that is not found in association with the other molecule in nature. For example, a heterologous region of a nucleic acid vector could include a coding sequence flanked by sequences not found in association with the coding sequence in nature. Likewise, a "heterologous" region of a protein is a segment of amino acids within or attached to another peptide molecule that is not found in association with the other peptide molecule in nature (e.g., a fusion protein, or a protein with a tag). Similarly, a nucleic acid or protein can comprise a heterologous label or a heterologous secretion or localization sequence.

"Codon optimization" takes advantage of the degeneracy of codons, as exhibited by the multiplicity of three-base pair codon combinations that specify an amino acid, and generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a Cas9 protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host are also available (see, e.g., Gene Forge).

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a eukaryotic cell, a non-human mammalian cell, a human cell, a rodent cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety for all purposes.

A constitutive promoter is one that is active in all tissues or particular tissues at all developing stages. Examples of constitutive promoters include the human cytomegalovirus immediate early (hCMV), mouse cytomegalovirus immediate early (mCMV), human elongation factor 1 alpha (hEF1α), mouse elongation factor 1 alpha (mEF1α), mouse phosphoglycerate kinase (PGK), chicken beta actin hybrid (CAG or CBh), SV40 early, and beta 2 tubulin promoters.

Examples of inducible promoters include, for example, chemically regulated promoters and physically-regulated promoters. Chemically regulated promoters include, for example, alcohol-regulated promoters (e.g., an alcohol dehydrogenase (alcA) gene promoter), tetracycline-regulated promoters (e.g., a tetracycline-responsive promoter, a tetracycline operator sequence (tetO), a tet-On promoter, or a tet-Off promoter), steroid regulated promoters (e.g., a rat glucocorticoid receptor, a promoter of an estrogen receptor, or a promoter of an ecdysone receptor), or metal-regulated promoters (e.g., a metalloprotein promoter). Physically regulated promoters include, for example temperature-regulated promoters (e.g., a heat shock promoter) and light-regulated promoters (e.g., a light-inducible promoter or a light-repressible promoter).

Tissue-specific promoters can be, for example, neuron-specific promoters, glia-specific promoters, muscle cell-specific promoters, heart cell-specific promoters, kidney cell-specific promoters, bone cell-specific promoters, endothelial cell-specific promoters, or immune cell-specific promoters (e.g., a B cell promoter or a T cell promoter).

Developmentally regulated promoters include, for example, promoters active only during an embryonic stage of development, or only in an adult cell.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

"Complementarity" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A.

Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+ 0.41(% G+C), although other known Tm computations take into account nucleic acid structural characteristics.

"Hybridization condition" includes the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment. See, e.g., Sambrook et al., Molecular Cloning, A Laboratory Manual, 2.sup.nd ed., pp. 1.90-1.91, 9.47-9.51, 1 1.47-11.57 (Cold Spring Harbor Laboratory Press, Cold Spring Harbor, N.Y., 1989), herein incorporated by reference in its entirety for all purposes.

Hybridization requires that the two nucleic acids contain complementary sequences, although mismatches between bases are possible. The conditions appropriate for hybridization between two nucleic acids depend on the length of the nucleic acids and the degree of complementation, variables which are well known. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid include at least about 15 nucleotides, at least about 20 nucleotides, at least about 22 nucleotides, at least about 25 nucleotides, and at least about 30 nucleotides. Furthermore, the temperature and wash solution salt concentration may be adjusted as necessary according to factors such as length of the region of complementation and the degree of complementation.

The sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide (e.g., gRNA) can comprise at least 70%, at least 80%, at least 90%, at least 95%, at least 99%, or 100% sequence complementarity to a target region within the target nucleic acid sequence to which they are targeted. For example, a gRNA in which 18 of 20 nucleotides are complementary to a target region, and would therefore specifically hybridize, would represent 90% complementarity. In this example, the remaining noncomplementary nucleotides may be clustered or interspersed with complementary nucleotides and need not be contiguous to each other or to complementary nucleotides.

Percent complementarity between particular stretches of nucleic acid sequences within nucleic acids can be determined routinely using BLAST programs (basic local alignment search tools) and PowerBLAST programs (Altschul et al. (1990) *J. Mol. Biol.* 215:403-410; Zhang and Madden (1997) *Genome Res.* 7:649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The methods and compositions provided herein employ a variety of different components. Some components throughout the description can have active variants and fragments. Such components include, for example, Cas proteins, CRISPR RNAs, tracrRNAs, and guide RNAs. Biological activity for each of these components is described elsewhere herein. The term "functional" refers to the innate ability of a protein or nucleic acid (or a fragment or variant thereof) to exhibit a biological activity or function. Such biological activities or functions can include, for example, the ability of a Cas protein to bind to a guide RNA and to a target DNA sequence. The biological functions of functional fragments or variants may be the same or may in fact be changed (e.g., with respect to their specificity or selectivity or efficacy) in comparison to the original, but with retention of the basic biological function.

The term "variant" refers to a nucleotide sequence differing from the sequence most prevalent in a population (e.g., by one nucleotide) or a protein sequence different from the sequence most prevalent in a population (e.g., by one amino acid).

The term "fragment" when referring to a protein means a protein that is shorter or has fewer amino acids than the full-length protein. The term "fragment" when referring to a nucleic acid means a nucleic acid that is shorter or has fewer nucleotides than the full-length nucleic acid. A fragment can be, for example, an N-terminal fragment (i.e., removal of a portion of the C-terminal end of the protein), a C-terminal fragment (i.e., removal of a portion of the N-terminal end of the protein), or an internal fragment.

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins, residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

"Percentage of sequence identity" includes the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized in Table 1 below.

TABLE 1

Amino Acid Categorizations.

| Alanine | Ala | A | Nonpolar | Neutral | 1.8 |
| Arginine | Arg | R | Polar | Positive | -4.5 |
| Asparagine | Asn | N | Polar | Neutral | -3.5 |
| Aspartic acid | Asp | D | Polar | Negative | -3.5 |
| Cysteine | Cys | C | Nonpolar | Neutral | 2.5 |
| Glutamic acid | Glu | E | Polar | Negative | -3.5 |
| Glutamine | Gln | Q | Polar | Neutral | -3.5 |
| Glycine | Gly | G | Nonpolar | Neutral | -0.4 |
| Histidine | His | H | Polar | Positive | -3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | -3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | -1.6 |
| Serine | Ser | S | Polar | Neutral | -0.8 |
| Threonine | Thr | T | Polar | Neutral | -0.7 |
| Tryptophan | Trp | W | Nonpolar | Neutral | -0.9 |
| Tyrosine | Tyr | Y | Polar | Neutral | -1.3 |
| Valine | Val | V | Nonpolar | Neutral | 4.2 |

The term "in vitro" includes artificial environments and to processes or reactions that occur within an artificial environment (e.g., a test tube). The term "in vivo" includes natural environments (e.g., a cell or organism or body) and to processes or reactions that occur within a natural environment. The term "ex vivo" includes cells that have been removed from the body of an individual and to processes or reactions that occur within such cells.

The term "reporter gene" refers to a nucleic acid having a sequence encoding a gene product (typically an enzyme) that is easily and quantifiably assayed when a construct comprising the reporter gene sequence operably linked to an endogenous or heterologous promoter and/or enhancer element is introduced into cells containing (or which can be made to contain) the factors necessary for the activation of the promoter and/or enhancer elements. Examples of reporter genes include, but are not limited, to genes encoding beta-galactosidase (lacZ), the bacterial chloramphenicol acetyltransferase (cat) genes, firefly luciferase genes, genes encoding beta-glucuronidase (GUS), and genes encoding fluorescent proteins. A "reporter protein" refers to a protein encoded by a reporter gene.

The term "fluorescent reporter protein" as used herein means a reporter protein that is detectable based on fluorescence wherein the fluorescence may be either from the reporter protein directly, activity of the reporter protein on a fluorogenic substrate, or a protein with affinity for binding to a fluorescent tagged compound. Examples of fluorescent proteins include green fluorescent proteins (e.g., GFP, GFP-2, tagGFP, turboGFP, eGFP, Emerald, Azami Green, Monomeric Azami Green, CopGFP, AceGFP, and ZsGreen1), yellow fluorescent proteins (e.g., YFP, eYFP, Citrine, Venus, YPet, PhiYFP, and ZsYellow1), blue fluorescent proteins (e.g., BFP, eBFP, eBFP2, Azurite, mKalamal, GFPuv, Sapphire, and T-sapphire), cyan fluorescent proteins (e.g., CFP, eCFP, Cerulean, CyPet, AmCyan1, and Midoriishi-Cyan), red fluorescent proteins (e.g., RFP, mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, and Jred), orange fluorescent proteins (e.g., mOrange, mKO, Kusabira-Orange, Monomeric Kusabira-Orange, mTangerine, and tdTomato), and any other suitable fluorescent protein whose presence in cells can be detected by flow cytometry methods.

Repair in response to double-strand breaks (DSBs) occurs principally through two conserved DNA repair pathways: homologous recombination (HR) and non-homologous end joining (NHEJ). See Kasparek & Humphrey (2011) *Seminars in Cell & Dev. Biol.* 22:886-897, herein incorporated by reference in its entirety for all purposes. Likewise, repair of a target nucleic acid mediated by an exogenous donor nucleic acid can include any process of exchange of genetic information between the two polynucleotides.

The term "recombination" includes any process of exchange of genetic information between two polynucleotides and can occur by any mechanism. Recombination can occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) *Cell* 153:910-918; Mandalos et al. (2012) *PLOS ONE* 7:e45768:1-9; and Wang et al. (2013) *Nat Biotechnol.* 31:530-532, each of which is herein incorporated by reference in its entirety for all purposes.

NHEJ includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break. For example, NHEJ can also result in the targeted integration of an exogenous donor nucleic acid through direct ligation of the break ends with the ends of the exogenous donor nucleic acid (i.e., NHEJ-based capture). Such NHEJ-mediated targeted integration can be preferred for insertion of an exogenous donor nucleic acid when homology directed repair (HDR) pathways are not readily usable (e.g., in non-dividing cells, primary cells, and cells which perform homology-based DNA repair poorly). In addition, in contrast to homology-directed repair, knowledge concerning large regions of sequence identity flanking the cleavage site (beyond the overhangs created by Cas-mediated cleavage) is not needed, which can be beneficial when attempting targeted insertion into organisms that have genomes for which there is limited knowledge of the genomic sequence. The integration can proceed via ligation of blunt ends between the exogenous donor nucleic acid and the cleaved genomic sequence, or via ligation of sticky ends (i.e., having 5' or 3' overhangs) using an exogenous donor nucleic acid that is flanked by overhangs that are compatible with those generated by the Cas protein in the cleaved genomic sequence. See, e.g., US 2011/020722, WO 2014/033644, WO 2014/089290, and Maresca et al. (2013) *Genome Res.* 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which it does not.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

The singular forms of the articles "a," "an," and "the" include plural references unless the context clearly dictates otherwise. For example, the term "a Cas protein" or "at least one Cas protein" can include a plurality of Cas proteins, including mixtures thereof.

Statistically significant means $p \leq 0.05$.

DETAILED DESCRIPTION

I. Overview

Assessing the efficiency of delivery and the efficiency of mutation generation or targeted gene modification by an introduced CRISPR/Cas agent in vivo currently relies on difficult molecular assays, such as single-strand DNase sensitivity assays, digital PCR, or next generation sequencing. Better methods and tools are needed to more effectively assess the activity of CRISPR/Cas agents and to assess different delivery methods and parameters for targeting specific tissues or cell types in vivo.

Methods and compositions are provided for assessing CRISPR/Cas-mediated non-homologous end joining (NHEJ) activity and/or CRISPR/Cas-induced recombination of a target genomic nucleic acid with an exogenous donor nucleic acid in vivo and ex vivo. The methods and compositions employ cells and non-human animals comprising a CRISPR reporter (e.g., a genomically integrated CRISPR reporter) for detecting and measuring targeted excision of a sequence between two CRISPR/Cas nuclease cleavage sites or disruption of a sequence near a CRISPR/Cas nuclease cleavage site and/or detecting and measuring CRISPR/Cas-induced recombination of the CRISPR reporter with an exogenous donor nucleic acid to convert the coding sequence for a first reporter protein into a coding sequence for a different second reporter protein. Some such CRISPR reporters can be multifunctional reporters comprising two or more different types of reporter genes. These reporters are an improvement over CRISPR reporters with a single type of reporter gene because they enable the use of different methods for detecting and measuring CRISPR/Cas activity in vivo and ex vivo, such as in vivo imaging of the non-human animal, detection of fluorescence in cells isolated from the animal via flow cytometry or other methods, or histochemical staining of tissues isolated from the non-human animal. In this way, the limitations of one reporter protein can be offset by the advantages of another reporter protein. For example, beta-galactosidase (encoded by the lacZ gene) and fluorescent proteins are used in combination in some reporters. LacZ allows for the ability to take sections of tissue to visualize the precise boundaries of CRISPR/Cas-induced repair. LacZ staining is permanent and can be visualized with the naked eye or standard brightfield magnification. Fluorescent reporter proteins such as eBFP or eGFP allow for a precise count of correctly edited, unedited, and alternatively edited cells. Fluorescent reporter proteins allow tissues to be analyzed on a single cell basis (e.g., via FACS analysis) for exact ratios of edited cells.

The CRISPR reporters described herein that have a lacZ gene have additional advantages over other reporters, such as "traffic light" reporters that report a change from red fluorescent protein to green fluorescent protein upon CRISPR/Cas action. The lacZ gene through its encoded beta-galactosidase is the most thoroughly established and reliable of all reporters. The reporters described herein that comprise a lacZ gene are designed to produce a histological color read-out upon the action of CRISPR/Cas. Because beta-galactosidase is a multiple turnover enzyme that converts a substrate into a visible blue dye, it has the potential to be more sensitive than fluorescent reporter proteins, which require tens of thousands of proteins per cell for a detectable fluorescent signal. Compared with fluorescent proteins, beta-galactosidase produces a higher definition signal that can reveal fine cell-type specific expression patterns. Traffic light fluorescent reporters require CRISPR/Cas-induced mutations that produce a fortuitous reading frame change. In contrast, lacZ reporters described herein do not depend on reading frames; rather, they require only a simple deletion between to CRIPSR/Cas cleavage sites to delete or inactivate a transcriptional polyadenylation termination signal, thereby permitting expression of the downstream beta-galactosidase coding sequence. Unlike the traffic light and similar dual fluorescent protein reporter systems that require analysis and interpretation of the ratio of two different fluorescent signals, the lacZ reporter systems go from no signal in the unmodified state to a strong reporter signal after CRISPR/Cas activation of the allele.

In addition, some of the CRISPR reporters disclosed herein are multifunctional reporters in that they enable testing of not only CRISPR/Cas NHEJ activity in vivo and ex vivo but also enable testing of CRISPR/Cas-induced HDR activity in vivo and ex vivo via different readouts. Because some such reporters for testing CRISPR-induced recombination require changing only a single codon in the gene encoding a reporter protein to convert that reporter protein into a different reporter protein, smaller exogenous donor nucleic acids can be used than if an entire coding sequence for a reporter protein needed to be deleted and replaced with the sequence for a different reporter protein. In some such reporters, a fluorescent reporter protein is converted into a different fluorescent reporter protein (e.g., eBFP to eGFP, or vice versa). Such conversion allows for a precise count of correctly edited, unedited, and alternatively edited cells and allows tissue to be analyzed on a single cell basis via FACs analysis for exact ratios of edited cells.

Methods and compositions are also provided for making and using these non-human animals to test and measure the ability of a CRISPR/Cas nuclease to excise or disrupt a genomically integrated nucleic acid and/or to facilitate recombination of a target genomic nucleic acid with an exogenous donor nucleic acid in vivo and to optimize the ability of a CRISPR/Cas nuclease to excise or disrupt a genomically integrated nucleic acid and/or to facilitate recombination of a target genomic locus with an exogenous donor in vivo.

II. Non-Human Animals Comprising CRISPR Reporters

The methods and compositions disclosed herein utilize a CRISPR reporter to assess the ability of introduced Clustered Regularly Interspersed Short Palindromic Repeats (CRISPR)/CRISPR-associated (Cas) systems or components of such systems to modify the CRISPR reporter in vivo or ex vivo.

The methods and compositions disclosed herein employ the CRISPR/Cas systems by testing the ability of CRISPR complexes (comprising a guide RNA (gRNA) complexed with a Cas protein) to induce two site-directed cleavage events within a CRISPR reporter in vivo or ex vivo and excise the intervening sequence between the two cleavage sites via non-homologous end joining (NHEJ) or to induce a site-directed cleavage event within a CRISPR reporter in vivo or ex vivo and disrupt a nearby sequence via NHEJ-mediated small insertions and deletions (indels). The methods and compositions disclosed herein also employ the CRISPR/Cas systems by testing the ability of CRISPR complexes (comprising a guide RNA (gRNA) complexed with a Cas protein) to induce recombination between a CRISPR reporter and an exogenous donor nucleic acid in vivo or ex vivo to repair a coding sequence for a first reporter protein in order to convert it into a coding sequence for a different second reporter protein.

A. CRISPR Reporters for Measuring CRISPR/Cas-Mediated Disruption or CRISPR/Cas-Mediated Excision Using Paired gRNAs and/or for Measuring CRISPR/Cas-Induced Recombination of a Target Genomic Nucleic Acid with an Exogenous Donor Nucleic Acid Provided herein are CRISPR reporters for detecting and measuring targeted excision of a sequence between two CRISPR/Cas nuclease cleavage sites or targeted disruption of a sequence near a CRISPR/Cas nuclease cleavage site and/or for detecting and measuring CRISPR/Cas-induced recombination of a target nucleic acid with an exogenous donor nucleic acid. The CRISPR reporters provided herein can comprise a polyadenylation signal or transcription terminator flanked by first and second guide RNA target sequences followed by a reporter cassette comprising a coding sequence for one or more reporter proteins. Alternatively or additionally, the polyadenylation signal or transcription terminator can comprise a third guide RNA target sequence at or near the canonical polyadenylation hexamer (AATAAA, referred to as a poly A recognition motif or poly A recognition sequence). Examples of guide RNA target sequences near the canonical polyadenylation hexamer in a Pgk polyadenylation signal include SEQ ID NOS: 48-52. However, any desired guide RNA target sequence can be included in or engineered into the CRISPR reporter so that any guide RNA or combination of guide RNAs can be tested. Alternatively or additionally, the polyadenylation signal or transcription terminator can be flanked by first and second recombinase recognition sites. The polyadenylation signal or transcription terminator prevents transcription and expression of the one or more reporter proteins. However, upon cleavage of the first and second guide RNA target sequences by a CRISPR/Cas nuclease and excision of the intervening sequence including the transcription terminator or polyadenylation signal, transcription can proceed through the coding sequence for the one or more reporter proteins, enabling their expression. Alternatively, upon cleavage of a guide RNA target sequence at or near the poly A recognition motif (canonical polyadenylation hexamer AATAAA) and disruption of the poly A recognition motif via NHEJ-mediated small insertions and deletions (indels), transcription can proceed through the coding sequence for the one or more reporter proteins, enabling their expression.

Any transcription terminator or polyadenylation signal can be used. A "transcription terminator" as used herein refers to a DNA sequence that causes termination of transcription. In eukaryotes, transcription terminators are recognized by protein factors, and termination is followed by polyadenylation, a process of adding a poly(A) tail to the mRNA transcripts in presence of the poly(A) polymerase. The mammalian poly(A) signal typically consists of a core sequence, about 45 nucleotides long, that may be flanked by diverse auxiliary sequences that serve to enhance cleavage and polyadenylation efficiency. The core sequence consists of a highly conserved and required upstream element (the poly A recognition motif AATAAA or AAUAAA in the mRNA), recognized by cleavage and polyadenylation-specificity factor (CPSF), and a poorly defined downstream region (rich in Us or Gs and Us), bound by cleavage stimulation factor (CstF). Examples of transcription terminators that can be used include, for example, the human growth hormone (HGH) polyadenylation signal, the simian virus 40 (SV40) late polyadenylation signal, the rabbit beta-globin polyadenylation signal, the bovine growth hormone (BGH) polyadenylation signal, the phosphoglycerate kinase (PGK) polyadenylation signal, an AOX1 transcription termination sequence, a CYC1 transcription termination sequence, or any transcription termination sequence known to be suitable for regulating gene expression in eukaryotic cells.

Optionally, the polyadenylation signal can also be flanked by recombinase recognition sites for a site-specific recombinase. The recombinase can be used as a positive control for excision of the polyadenylation signal. Site-specific recombinases include enzymes that can facilitate recombination between recombinase recognition sites, where the two recombination sites are physically separated within a single nucleic acid or on separate nucleic acids. Examples of recombinases include Cre, Flp, and Dre recombinases. One example of a Cre recombinase gene is Crei, in which two exons encoding the Cre recombinase are separated by an intron to prevent its expression in a prokaryotic cell. Such recombinases can further comprise a nuclear localization signal to facilitate localization to the nucleus (e.g., NLS-Crei). Recombinase recognition sites include nucleotide sequences that are recognized by a site-specific recombinase and can serve as a substrate for a recombination event. Examples of recombinase recognition sites include FRT, FRT11, FRT71, attp, att, rox, and lox sites such as loxP, lox511, lox2272, lox66, lox71, loxM2, and lox5171.

The first and second guide RNA target sequences can be the same or different, and any suitable guide RNA target sequence can be used. Any desired guide RNA target sequence can be included in or engineered into the CRISPR reporter so that any guide RNA or combination of guide RNAs can be tested. Guide RNA target sequences are described in more detail elsewhere herein. As one example, the first guide RNA target sequence can comprise the sequence set forth in SEQ ID NO: 41, 43, 44, or 45, and the second guide RNA target sequence can comprise the sequence set forth in SEQ ID NO: 41, 46, or 47. The first and second guide RNA target sequences (or the first and second Cas cleavage sites within the first and second guide RNA target sequences, respectively) can be separated by any desired distance to be tested. For example, they can be separated by at least 5, 6, 7, 8, 9, 10, 20, 30, 40, 50, 100, 200, 300, 400, 500, 600, or 1000 base pairs (bp), no more than 5, 6, 7, 8, 9, 10, 20, 30, 40, 50, 100, 200, 300, 400, 500, 600, or 1000 bp, or between about 5-100, 5-200, 5-300, 5-400, 5-500, 5-600, 5-1000, 6-100, 6-200, 6-300, 6-400, 6-500, 6-600, 6-1000, 10-100, 10-200, 10-300, 10-400, 10-500, 10-600, 10-1000, 50-100, 50-200, 50-300, 50-400, 50-500, 50-600, 50-1000, 100-1000, 200-1000, 300-1000, 400-1000, or 500-1000 bp. In a specific example, the guide RNA target sequences or Cas cleavage sites can separated by less than about 1000, less than about 600, less than about 500, less than about 200, or less than about 100 base pairs. Alternatively, they can be separated by at least 1, 2, 3, 4, 5, 6, 7, 8, 9, 10, 20, 30, 40, 50, or 100 kb or more, or can be separated by between about 1-10, 1-20, 1-30, 1-40, 1-50, 1-100, 10-20, 10-30, 10-40, 10-50, 10-100, 20-30, 20-40, 20-50, 20-100, 30-40, 30-50, 30-100, 40-50, 40-100, or 50-100 kb. For example, the first and second guide RNA target sequences or first and second Cas cleavage sites can be separated by between about 5 by to 10 kb, 6 by to 10 kb, 10 by to 10 kb, 50 by to 10 kb, 100 by to 10 kb, 200 bp to 10 kb, 300 bp to 10 kb, 400 bp to 10 kb, or 500 bp to 10 kb.

The first and second guide RNA target sequences (or the first and second Cas cleavage sites) are optionally at (i.e., overlapping) or near the poly A recognition motif (canonical polyadenylation signal hexamer AATAAA). For example, one or both of the first and second guide RNA target sequences or the first and second Cas cleavage sites can be within about 1, 2, 3, 4, 5, 6, 7, 8, 9, 10, 20, 30, 40, 50, 100, 200, 300, 400, 500, 600, or 1000 bp, or between about 1-100, 1-200, 1-300, 1-400, 1-500, 1-600, 1-1000, 5-100, 5-200, 5-300, 5-400, 5-500, 5-600, 5-1000, 10-100, 10-200, 10-300, 10-400, 10-500, 10-600, 10-1000, 50-100, 50-200, 50-300, 50-400, 50-500, 50-600, 50-1000, 100-1000, 200-1000, 300-1000, 400-1000, or 500-1000 bp from the canonical polyadenylation signal hexamer. Optionally, a third guide RNA target sequence (or Cas cleavage site) is at (i.e., overlapping) or near the poly A recognition motif (canonical polyadenylation signal hexamer AATAAA). For example, the third guide RNA target sequences or the third Cas cleavage site can be within about 1, 2, 3, 4, 5, 6, 7, 8, 9, 10, 20, 30, 40, 50, 60, 70, 80, 90, 100, 200, 300, 400, 500, 600, or 1000 bp, or between about 1-10, 1-20, 1-30, 1-40, 1-50, 1-60, 1-70, 1-80, 1-90, 1-100, 1-200, 1-300, 1-400, 1-500, 1-600, 1-1000, 5-10, 5-20, 5-30, 5-40, 5-50, 5-60, 5-70, 5-80, 5-90, 5-100, 5-200, 5-300, 5-400, 5-500, 5-600, 5-1000, 10-10, 10-20, 10-30, 10-40, 10-50, 10-60, 10-70, 10-80, 10-90, 10-100, 10-200, 10-300, 10-400, 10-500, 10-600, 10-1000, 50-100, 50-200, 50-300, 50-400, 50-500, 50-600, 50-1000, 100-1000, 200-1000, 300-1000, 400-1000, or 500-1000 bp from the canonical polyadenylation signal hexamer. For example, the third guide RNA target sequence or third Cas cleavage site can be within about 10-220, 20-200, 20-40, 29, 65-85, 76, 185-205, or 195 bp from the canonical polyadenylation signal hexamer.

The first and second guide RNA target sequences can be anywhere with respect to the first and second recombinase recognition sites, respectively. The first guide RNA target sequence can be upstream or downstream of the first recombinase recognition site or can overlap with the first recombinase recognition site. Likewise, the second guide RNA target sequence can be upstream or downstream of the second recombinase recognition site or can overlap with the second recombinase recognition site. In addition, the first guide RNA target sequence can be upstream of the flanked transcription terminator or polyadenylation signal or can overlap with the transcription terminator or polyadenylation signal. Likewise, the second guide RNA target sequence can be downstream of the flanked transcription terminator or polyadenylation signal or can overlap with the transcription terminator or polyadenylation signal.

Any suitable reporter proteins can be used. In some reporters, the one or more reporter proteins comprise a beta-galactosidase protein. In other reporters, there are two or more different reporter proteins. Optionally, the two or more reporter proteins can be different types of reporter proteins. For example, the two or more different reporter proteins can include at least one fluorescent reporter protein as defined elsewhere herein and at least one non-fluorescent reporter protein. Examples of fluorescent reporter proteins are provided elsewhere herein. Non-fluorescent reporter proteins include, for example, reporter proteins that can be used in histochemical or bioluminescent assays, such as beta-galactosidase, luciferase (e.g., Renilla luciferase, firefly luciferase, and NanoLuc luciferase), and beta-glucuronidase. Some reporters include both a reporter protein that can be detected in a flow cytometry assay (e.g., a fluorescent reporter protein such as a blue fluorescent protein (BFP), an enhanced BFP (eBFP), a green fluorescent protein (GFP), or an enhanced GFP (eGFP)) and a reporter protein that can be detected in a histochemical assay (e.g., beta-galactosidase protein) to provide additional functionality and enable different types of assays to be performed to detect and measure CRISPR activity in vivo. One example of such a histochemical assay is visualization of in situ beta-galactosidase expression histochemically through hydrolysis of X-Gal (5-bromo-4-chloro-3-indoyl-b-D-galactopyranoside), which yields a blue precipitate, or using fluorogenic substrates such as beta-methyl umbelliferyl galactoside (MUG) and fluorescein digalactoside (FDG).

When two or more reporter proteins are included in the CRISPR reporter, the coding sequence for the two or more reporter proteins can comprise a multicistronic nucleic acid. Multicistronic expression constructs simultaneously express two or more separate proteins from the same mRNA (i.e., a transcript produced from the same promoter). Suitable strategies for multicistronic expression of proteins include, for example, the use of a 2A peptide and the use of an internal ribosome entry site (IRES). For example, such nucleic acids can comprise coding sequences for two or more reporter proteins separated by an intervening internal ribosome entry site (IRES) or an intervening 2A peptide coding sequence. As one example, such multicistronic vectors can use one or more internal ribosome entry sites (IRES) to allow for initiation of translation from an internal region of an mRNA. As another example, such multicistronic vectors can use one or more 2A peptides. These peptides are small "self-cleaving" peptides, generally having a length of 18-22 amino acids and produce equimolar levels of multiple genes from the same mRNA. Ribosomes skip the synthesis of a glycyl-prolyl peptide bond at the C-terminus of a 2A peptide, leading to the "cleavage" between a 2A peptide and its immediate downstream peptide. See, e.g., Kim et al. (2011) *PLoS One* 6(4): e18556, herein incorporated by reference in its entirety for all purposes. The "cleavage" occurs between the glycine and proline residues found on the C-terminus, meaning the upstream cistron will have a few additional residues added to the end, while the downstream cistron will start with the proline. As a result, the "cleaved-off" downstream peptide has proline at its N-terminus. 2A-mediated cleavage is a universal phenomenon in all eukaryotic cells. 2A peptides have been identified from picornaviruses, insect viruses and type C rotaviruses. See, e.g., Szymczak et al. (2005) *Expert Opin Biol Ther* 5:627-638, herein incorporated by reference in its entirety for all purposes. Examples of 2A peptides that can be used include *Thosea asigna* virus 2A (T2A); porcine teschovirus-1 2A (P2A); equine rhinitis A virus (ERAV) 2A (E2A); and FMDV 2A (F2A). Exemplary T2A, P2A, E2A, and F2A sequences include the following: T2A (EGRGSLLTCGDVEENPGP; SEQ ID NO: 3); P2A (ATNFSLLKQAGDVEENPGP; SEQ ID NO: 4); E2A (QCTNYALLKLAGDVESNPGP; SEQ ID NO: 5); and F2A (VKQTLNFDLLKLAGDVESNPGP; SEQ ID NO: 6). GSG residues can be added to the 5' end of any of these peptides to improve cleavage efficiency.

The CRISPR reporter can be operably linked to any suitable promoter for expression in vivo within a non-human animal. The non-human animal can be any suitable non-human animal as described elsewhere herein. As one example, the CRISPR reporter can be operably linked to an endogenous promoter at a target genomic locus, such as a Rosa26 promoter at an endogenous Rosa26 locus. Alternatively, the CRISPR reporter can be operably linked to an exogenous promoter. The promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Such promoters are well-known and are discussed elsewhere herein.

The CRISPR reporters disclosed herein can comprise other components as well. Some CRISPR reporters further comprise a 3' splicing sequence at the 5' end of the CRISPR reporter and/or a second polyadenylation signal following the coding sequences for the reporter proteins at the 3' end of the CRISPR reporter. Some CRISPR reporters can further comprise a selection cassette comprising, for example, the coding sequence for a drug resistance protein. Alternatively, some CRISPR reporters disclosed herein do not comprise a selection cassette. Examples of suitable selection markers include neomycin phosphotransferase (neo$_r$), hygromycin B phosphotransferase (hyg$_r$), puromycin-N-acetyltransferase (puro$_r$), blasticidin S deaminase (bsr$_r$), xanthine/guanine phosphoribosyl transferase (gpt), and herpes simplex virus thymidine kinase (HSV-k). Optionally, the selection cassette can be flanked by recombinase recognition sites for a site-specific recombinase. If the CRISPR reporter also comprises recombinase recognition sites flanking the polyadenylation signal for use as a positive control as described above, optionally a different set of recombinase recognition sites recognized by a different recombinase are used to flank the selection cassette.

CRISPR reporters can also comprise a transcription terminator or polyadenylation signal in the reporter cassette (i.e., following or downstream of the coding sequence for the one or more reporter proteins). In some CRISPR reporters, the transcription terminator or polyadenylation signal flanked by the first and second guide RNA target sequences upstream of the reporter cassette comprising the coding sequence for the one or more reporter proteins is different from the transcription terminator or polyadenylation signal following the coding sequence for the one or more reporter proteins. In other CRISPR reporters, the transcription terminator or polyadenylation signal flanked by the first and second guide RNA target sequences upstream of the reporter cassette comprising the coding sequence for the one or more reporter proteins is the same as the transcription terminator or polyadenylation signal following the coding sequence for the one or more reporter proteins.

Alternatively or in addition to the CRISPR reporter elements described above, the CRISPR reporters provided herein can comprise a guide RNA target sequence and a coding sequence for a reporter protein that can be converted to the coding sequence for a different reporter protein. Upon cleavage of the guide RNA target sequence by a CRISPR/Cas nuclease and repair of the reporter protein coding sequence with an exogenous donor nucleic acid, the coding sequence for the reporter protein is converted to the coding sequence for a different reporter protein. Optionally, the coding sequence for original reporter protein can be changed into a coding sequence for the different reporter protein by changing a single codon. For example, some such CRISPR reporters do not comprise a polyadenylation signal or transcription terminator upstream of the coding sequence for the reporter protein. Other such CRISPR reporters do comprise a polyadenylation signal or transcription terminator upstream of the coding sequence for the reporter protein as described above. Some such CRISPR reporters comprise a single reporter protein coding sequence. See, e.g., FIG. 3 and SEQ ID NOS: 18, 57, and 60. Other such CRISPR reporters comprise coding sequences for two or more reporter proteins as described above. See, e.g., FIG. 1A and SEQ ID NOS: 17, 58, and 59. Some such CRISPR reporters can further comprise a selection cassette comprising, for example, the coding sequence for a drug resistance protein. Alternatively, some such CRISPR reporters do not comprise a selection cassette.

Any suitable guide RNA target sequence can be used as described elsewhere herein. As one example, the guide RNA target sequence can comprise the sequence set forth in SEQ ID NO: 42 or 56. The guide RNA sequence can be within the coding sequence for the reporter protein, optionally within a defined distance from the region of the coding sequence to be altered upon recombination with the exogenous donor sequence to convert the coding sequence to a coding sequence for a different reporter protein. Alternatively, the guide RNA sequence can be outside of and adjacent to the coding sequence for the reporter protein. For example, the guide RNA target sequence can be within 1, 5, 10, 50, 100, 200, 300, 400, 500, or 1000 base pairs (bp) or between about 1-100, 1-200, 1-300, 1-400, 1-500, 1-1000, 5-1000, 10-5000, 50-1000, 100-1000, 200-1000, 300-1000, 400-1000, or 500-1000 bp from the 5' or 3' end of the coding sequence for the reporter protein or from the region of the coding sequence to be altered. In a specific example, the guide RNA target sequence can be within about 1000 or within about 500 base pairs of the region to be altered or can overlap with the region to be altered. Alternatively, the guide RNA target sequence can be within about 1, 2, 3, 4, 5, or 10 kb, or between about 1-2, 1-3, 1-4, 1-5, or 1-10 kb from the 5' or 3' end of the coding sequence for the reporter protein or from the region of the coding sequence to be altered. For example, the guide RNA target sequence can be between about 1 bp to 1 kb, 1 bp to 2 kb, 1 bp to 3 kb, 1 bp to 4 kb, 1 bp to 5 kb, or 1 bp to 10 kb from the 5' or 3' end of the coding sequence for the reporter protein or the region of the coding sequence to be altered.

Any suitable reporter protein as described elsewhere herein, such as a fluorescent reporter protein, can be used. In a specific example, the reporter protein can be converted to a different reporter protein through changing a single codon. For example, enhanced GFP (eGFP) emits green fluorescence, but a single amino acid substitution of histidine to tyrosine at position 66 (Y66H) results in a spectral shift to blue fluorescence (i.e., conversion from eGFP to eBFP). Likewise, the reverse substitution in eBFP (H66Y) can convert eBFP to eGFP. Other examples of mutations in eGFP that can result in spectral shifts include T203Y (yellow derivatives) and Y66W (cyan derivatives). Yet other examples of mutations in eGFP can convert eGFP to BFP (e.g., mutating the LTYG at positions 64-67 of eGFP to FX). In one specific example, the original reporter protein is GFP or eGFP and is converted into BFP or eBFP, or vice versa. In another specific example, the original reporter protein is GFP or eGFP and is converted into CFP or eCFP, or vice versa. In another specific example, the original reporter protein is GFP or eGFP and is converted into YFP or eYFP, or vice versa.

One exemplary CRISPR reporter comprises from 5' to 3': (a) a 3' splicing sequence; (b) a first polyadenylation signal flanked by: (i) first and second recombinase recognition sites for a first recombinase (e.g., loxP sites for a Cre recombinase); and (ii) first and second guide RNA target sequences (e.g., guide RNA target sequences each comprising SEQ ID NO: 41); (c) a reporter cassette, comprising from 5' to 3': (i) a beta-galactosidase coding sequence; (ii) a P2A coding sequence; (iii) a fluorescent protein (e.g., green fluorescent protein (GFP), blue fluorescent protein (BFP), enhanced GFP (eGFP), or enhanced BFP (eBFP)) coding sequence (optionally comprising a third guide RNA target sequence); and (iv) a second polyadenylation signal. Optionally, the CRISPR reporter comprises guide RNA target sequences comprising SEQ ID NOS: 41, 43, 44, 45, 46, and 47. The first and second guide RNA target sequences can comprise, for example, SEQ ID NOS: 43 and 46, SEQ ID NOS: 43 and 47, SEQ ID NOS: 44 and 46, SEQ ID NOS: 44 and 47, SEQ ID NOS: 45 and 46, SEQ ID NOS: 45 and 47, SEQ ID NOS: 43 and 41, SEQ ID NOS: 44 and 41, SEQ ID NOS: 45 and 41, SEQ ID NOS: 41 and 46, or SEQ ID NOS: 41 and 47. Alternatively, each can comprise SEQ ID NO: 41. Optionally, the CRISPR reporter further comprises one or more guide RNA target sequences within the first polyadenylation signal. Examples of such guide RNA target sequences include SEQ ID NOS: 48-52. Optionally, the first polyadenylation signal and the second polyadenylation signal are different. Optionally, the CRISPR reporter can further comprise a selection cassette (e.g., 3' of the reporter cassette), wherein the selection cassette is flanked by recombinase recognition sites for a second recombinase (e.g., FRT sites for a Flp recombinase). The selection cassette can comprise, for example, from 5' to 3': (i) a third polyadenylation signal (e.g., in antisense orientation); and (ii) the coding sequence for a drug resistance gene (e.g., in antisense orientation) operably linked to a promoter (e.g., a neomycin resistance gene (neomycin phosphotransferase) coding sequence operably linked to a constitutive promoter such as a human ubiquitin promoter). Alternatively, the selection cassette can be flanked by recombinase recognition sites for a second recombinase (e.g., FRT sites for a Flp recombinase) and comprises from 5' to 3': (i) the coding sequence for a drug resistance gene (e.g., in sense orientation) operably linked to a promoter (e.g., a neomycin resistance gene (neomycin phosphotransferase) coding sequence operably linked to a constitutive promoter such as a human ubiquitin promoter and an EM7 promoter); and (ii) a third polyadenylation signal (e.g., Pgk polyadenylation signal in sense orientation). See, e.g., FIG. 1A and SEQ ID NO: 17. Optionally, the CRISPR reporter can be the CRISPR reporter comprising the selection cassette following treatment with the recombinase and excision of the selection cassette. See, e.g., FIG. 1A and SEQ ID NO: 17 following treatment with Flp recombinase and excision of the neomycin selection cassette. Optionally, the CRISPR reporter can be the CRISPR reporter (with or without the selection cassette) following treatment with a recombinase and excision of the first polyadenylation signal. See, e.g., FIG. 1A and SEQ ID NO: 17 following treatment with Cre recombinase and excision of the Pgk polyadenylation signal, resulting in SEQ ID NO: 58 (or SEQ ID NO: 59 upon conversion from eBFP to eGFP).

Another exemplary CRISPR reporter comprises from 5' to 3': (a) a 3' splicing sequence; (b) a first polyadenylation signal comprising a guide RNA target sequence (e.g., SEQ ID NO: 48, 49, 50, 51, or 52) flanked by first and second recombinase recognition sites for a first recombinase (e.g., loxP sites for a Cre recombinase); (c) a reporter cassette, comprising from 5' to 3': (i) a beta-galactosidase coding sequence; (ii) a P2A coding sequence; (iii) a fluorescent protein (e.g., green fluorescent protein (GFP), blue fluorescent protein (BFP), enhanced GFP (eGFP), or enhanced BFP (eBFP)) coding sequence (optionally comprising a second guide RNA target sequence); and (iv) a second polyadenylation signal. Optionally, the first polyadenylation signal and the second polyadenylation signal are different. Optionally, the CRISPR reporter can further comprise a selection cassette (e.g., 3' of the reporter cassette), wherein the selection cassette is flanked by recombinase recognition sites for a second recombinase (e.g., FRT sites for a Flp recombinase). The selection cassette can comprise, for example, from 5' to 3': (i) a third polyadenylation signal (e.g., in antisense orientation); and (ii) the coding sequence for a drug resistance gene (e.g., in antisense orientation) operably linked to a promoter (e.g., a neomycin resistance gene (neomycin phosphotransferase) coding sequence operably linked to a constitutive promoter such as a human ubiquitin promoter). Alternatively, the selection cassette can be flanked by recombinase recognition sites for a second recombinase (e.g., FRT sites for a Flp recombinase) and comprises from 5' to 3': (i) the coding sequence for a drug resistance gene (e.g., in sense orientation) operably linked to a promoter (e.g., a neomycin resistance gene (neomycin phosphotransferase) coding sequence operably linked to a constitutive promoter such as a human ubiquitin promoter and an EM7 promoter); and (ii) a third polyadenylation signal (e.g., Pgk polyadenylation signal in sense orientation). See, e.g., FIG. 1A and SEQ ID NO: 17. Optionally, the CRISPR reporter can be the CRISPR reporter comprising the selection cassette following treatment with the recombinase and excision of the selection cassette. See, e.g., FIG. 1A and SEQ ID NO: 17 following treatment with Flp recombinase and excision of the neomycin selection cassette. Optionally, the CRISPR reporter can be the CRISPR reporter (with or without the selection cassette) following treatment with a recombinase and excision of the first polyadenylation signal. See, e.g., FIG. 1A and SEQ ID NO: 17 following treatment with Cre recombinase and excision of the Pgk polyadenylation signal, resulting in SEQ ID NO: 58 (or SEQ ID NO: 59 upon conversion from eBFP to eGFP).

An exemplary CRISPR reporter for testing only CRISPR/Cas-induced recombination comprises from 5' to 3': (a) a 3' splicing sequence; (b) a first recombinase recognition site (e.g., loxP site for Cre recombinase): (c) a first polyadenylation signal (e.g., a triple polyadenylation signal); (d) a drug resistance gene operably linked to a promoter (e.g., a neomycin resistance gene operably linked to an EM7 promoter); (e) a second recombinase recognition site; (f) a fluorescent protein coding sequence (e.g., green fluorescent protein (GFP), blue fluorescent protein (BFP), enhanced GFP (eGFP), or enhanced BFP (eBFP)) comprising a guide RNA target sequence; and (g) a second polyadenylation signal (e.g., a SV40 polyadenylation signal). See, e.g., FIG. 3 and SEQ ID NO: 18. Optionally, the CRISPR reporter can be the CRISPR reporter following treatment with the recombinase and excision of the selection cassette and first polyadenylation signal. See, e.g., FIG. 3 and SEQ ID NO: 18 following treatment with Cre recombinase and excision of the neomycin selection cassette and triple polyadenylation signal, resulting in SEQ ID NO: 57 (or SEQ ID NO: 60 upon conversion from eBFP to eGFP).

The CRISPR reporters described herein can be in any form. For example, a CRISPR reporter can be in a plasmid or vector, such as a viral vector. Likewise, the CRISPR reporter can be operably linked to a promoter in an expression construct capable of directing expression of the reporter proteins upon removal of the upstream polyadenylation signal. Likewise, a CRISPR reporter can be in a targeting vector as defined elsewhere herein. For example, the targeting vector can comprise homology arms flanking the CRISPR reporter, wherein the homology arms are suitable for directing recombination with a desired target genomic locus to facilitate genomic integration.

Likewise, the CRISPR reporters described herein can be in vitro, they can be within a cell (e.g., an embryonic stem cell) ex vivo (e.g., genomically integrated or extrachromosomal), or they can be in an organism (e.g., a non-human animal) in vivo (e.g., genomically integrated or extrachromosomal). If ex vivo, the CRISPR reporter can be in any type of cell from any organism, such as a totipotent cell such as an embryonic stem cell (e.g., a mouse or a rat embryonic stem cell) or an induced pluripotent stem cell (e.g., a human induced pluripotent stem cell). If in vivo, the CRISPR reporter can be in any type of organism (e.g., a non-human animal as described further below).

B. Cells and Non-Human Animals Comprising CRISPR Reporters

Cells and non-human animals comprising the CRISPR reporters described herein are also provided. The CRISPR reporter can be stably integrated into the genome (i.e., into a chromosome) of the cell or non-human animal or it can be located outside of a chromosome (e.g., extrachromosomally replicating DNA). Optionally, the CRISPR reporter is stably integrated into the genome. The stably integrated CRISPR reporter can be randomly integrated into the genome of the non-human animal (i.e., transgenic), or it can be integrated into a predetermined region of the genome of the non-human animal (i.e., knock in). Optionally, the CRISPR reporter is stably integrated into a predetermined region of the genome, such as a safe harbor locus. The target genomic locus at which the CRISPR reporter is stably integrated can be heterozygous for the CRISPR reporter or homozygous for the CRISPR reporter. A diploid organism has two alleles at each genetic locus. Each pair of alleles represents the genotype of a specific genetic locus. Genotypes are described as homozygous if there are two identical alleles at a particular locus and as heterozygous if the two alleles differ.

The cells provided herein can be, for example, eukaryotic cells, which include, for example, fungal cells (e.g., yeast), plant cells, animal cells, mammalian cells, non-human mammalian cells, and human cells. The term "animal" includes mammals, fishes, and birds. A mammalian cell can be, for example, a non-human mammalian cell, a human cell, a rodent cell, a rat cell, a mouse cell, or a hamster cell. Other non-human mammals include, for example, non-human primates, monkeys, apes, cats, dogs, rabbits, horses, bulls, deer, bison, livestock (e.g., bovine species such as cows, steer, and so forth; ovine species such as sheep, goats, and so forth; and porcine species such as pigs and boars). Birds include, for example, chickens, turkeys, ostrich, geese, ducks, and so forth. Domesticated animals and agricultural animals are also included. The term "non-human" excludes humans.

The cells can also be any type of undifferentiated or differentiated state. For example, a cell can be a totipotent cell, a pluripotent cell (e.g., a human pluripotent cell or a non-human pluripotent cell such as a mouse embryonic stem (ES) cell or a rat ES cell), or a non-pluripotent cell. Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

Examples of human pluripotent cells include human ES cells, human adult stem cells, developmentally restricted human progenitor cells, and human induced pluripotent stem (iPS) cells, such as primed human iPS cells and naïve human iPS cells. Induced pluripotent stem cells include pluripotent stem cells that can be derived directly from a differentiated adult cell. Human iPS cells can be generated by introducing specific sets of reprogramming factors into a cell which can include, for example, Oct3/4, Sox family transcription factors (e.g., Sox1, Sox2, Sox3, Sox15), Myc family transcription factors (e.g., c-Myc, l-Myc, n-Myc), Kruppel-like family (KLF) transcription factors (e.g., KLF1, KLF2, KLF4, KLF5), and/or related transcription factors, such as NANOG, LIN28, and/or Glis 1. Human iPS cells can also be generated, for example, by the use of miRNAs, small molecules that mimic the actions of transcription factors, or lineage specifiers. Human iPS cells are characterized by their ability to differentiate into any cell of the three vertebrate germ layers, e.g., the endoderm, the ectoderm, or the mesoderm. Human iPS cells are also characterized by their ability propagate indefinitely under suitable in vitro culture conditions. See, e.g., Takahashi and Yamanaka (2006) *Cell* 126:663-676, herein incorporated by reference in its entirety for all purposes. Primed human ES cells and primed human iPS cells include cells that express characteristics similar to those of post-implantation epiblast cells and are committed for lineage specification and differentiation. Naïve human ES cells and naïve human iPS cells include cells that express characteristics similar to those of ES cells of the inner cell mass of a pre-implantation embryo and are not committed for lineage specification. See, e.g., Nichols and Smith (2009) *Cell Stem Cell* 4:487-492, herein incorporated by reference in its entirety for all purposes.

The cells provided herein can also be germ cells (e.g., sperm or oocytes). The cells can be mitotically competent cells or mitotically-inactive cells, meiotically competent cells or meiotically-inactive cells. Similarly, the cells can also be primary somatic cells or cells that are not a primary somatic cell. Somatic cells include any cell that is not a gamete, germ cell, gametocyte, or undifferentiated stem cell. For example, the cells can be liver cells, kidney cells, hematopoietic cells, endothelial cells, epithelial cells, fibroblasts, mesenchymal cells, keratinocytes, blood cells, melanocytes, monocytes, mononuclear cells, monocytic precursors, B cells, erythroid-megakaryocytic cells, eosinophils, macrophages, T cells, islet beta cells, exocrine cells, pancreatic progenitors, endocrine progenitors, adipocytes, pre-adipocytes, neurons, glial cells, neural stem cells, neurons, hepatoblasts, hepatocytes, cardiomyocytes, skeletal myoblasts, smooth muscle cells, ductal cells, acinar cells, alpha cells, beta cells, delta cells, PP cells, cholangiocytes, white or brown adipocytes, or ocular cells (e.g., trabecular meshwork cells, retinal pigment epithelial cells, retinal microvascular endothelial cells, retinal pericyte cells, conjunctival epithelial cells, conjunctival fibroblasts, iris pigment epithelial cells, keratocytes, lens epithelial cells, non-pigment ciliary epithelial cells, ocular choroid fibroblasts, photoreceptor cells, ganglion cells, bipolar cells, horizontal cells, or amacrine cells).

Suitable cells provided herein also include primary cells. Primary cells include cells or cultures of cells that have been isolated directly from an organism, organ, or tissue. Primary cells include cells that are neither transformed nor immortal. They include any cell obtained from an organism, organ, or tissue which was not previously passed in tissue culture or has been previously passed in tissue culture but is incapable of being indefinitely passed in tissue culture. Such cells can be isolated by conventional techniques and include, for example, somatic cells, hematopoietic cells, endothelial cells, epithelial cells, fibroblasts, mesenchymal cells, keratinocytes, melanocytes, monocytes, mononuclear cells, adipocytes, preadipocytes, neurons, glial cells, hepatocytes, skeletal myoblasts, and smooth muscle cells. For example, primary cells can be derived from connective tissues, muscle tissues, nervous system tissues, or epithelial tissues.

Other suitable cells provided herein include immortalized cells. Immortalized cells include cells from a multicellular organism that would normally not proliferate indefinitely but, due to mutation or alteration, have evaded normal cellular senescence and instead can keep undergoing division. Such mutations or alterations can occur naturally or be intentionally induced. Examples of immortalized cells include Chinese hamster ovary (CHO) cells, human embryonic kidney cells (e.g., HEK 293 cells or 293T cells), and mouse embryonic fibroblast cells (e.g., 3T3 cells). Numerous types of immortalized cells are well known. Immortalized or primary cells include cells that are typically used for culturing or for expressing recombinant genes or proteins.

The cells provided herein also include one-cell stage embryos (i.e., fertilized oocytes or zygotes). Such one-cell stage embryos can be from any genetic background (e.g., BALB/c, C57BL/6, 129, or a combination thereof for mice), can be fresh or frozen, and can be derived from natural breeding or in vitro fertilization.

The cells provided herein can be normal, healthy cells, or can be diseased or mutant-bearing cells.

Non-human animals comprising a CRISPR reporter as described herein can be made by the methods described elsewhere herein. The term "animal" includes mammals, fishes, and birds. Mammals include, for example, humans, non-human primates, monkeys, apes, cats, dogs, horses, bulls, deer, bison, sheep, rabbits, rodents (e.g., mice, rats, hamsters, and guinea pigs), and livestock (e.g., bovine species such as cows and steer; ovine species such as sheep and goats; and porcine species such as pigs and boars). Birds include, for example, chickens, turkeys, ostrich, geese, and ducks. Domesticated animals and agricultural animals are also included. The term "non-human animal" excludes humans. Preferred non-human animals include, for example, rodents, such as mice and rats.

The non-human animals can be from any genetic background. For example, suitable mice can be from a 129 strain, a C57BL/6 strain, a mix of 129 and C57BL/6, a BALB/c strain, or a Swiss Webster strain. Examples of 129 strains include 129P1, 129P2, 129P3, 129X1, 129S1 (e.g., 129S1/SV, 129S1/Sv1m), 129S2, 129S4, 129S5, 129S9/SvEvH, 129S6 (129/SvEvTac), 129S7, 129S8, 129T1, and 129T2. See, e.g., Festing et al. (1999) *Mammalian Genome* 10:836, herein incorporated by reference in its entirety for all purposes. Examples of C57BL strains include C57BL/A, C57BL/An, C57BL/GrFa, C57BL/Kal_wN, C57BL/6, C57BL/6J, C57BL/6ByJ, C57BL/6NJ, C57BL/10, C57BL/10ScSn, C57BL/10Cr, and C57BL/O1a. Suitable mice can also be from a mix of an aforementioned 129 strain and an aforementioned C57BL/6 strain (e.g., 50% 129 and 50% C57BL/6). Likewise, suitable mice can be from a mix of aforementioned 129 strains or a mix of aforementioned BL/6 strains (e.g., the 129S6 (129/SvEvTac) strain).

Similarly, rats can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats can also be obtained from a strain derived from a mix of two or more strains recited above. For example, a suitable rat can be from a DA strain or an ACI strain. The ACI rat strain is characterized as having black agouti, with white belly and feet and an $RT1^{av1}$ haplotype. Such strains are available from a variety of sources including Harlan Laboratories. The Dark Agouti (DA) rat strain is characterized as having an agouti coat and an $RT1^{av1}$ haplotype. Such rats are available from a variety of sources including Charles River and Harlan Laboratories. In some cases, suitable rats can be from an inbred rat strain. See, e.g., US 2014/0235933, herein incorporated by reference in its entirety for all purposes.

C. Target Genomic Loci

The CRISPR reporters described herein can be genomically integrated at a target genomic locus in a cell or a non-human animal. Any target genomic locus capable of expressing a gene can be used.

An example of a target genomic locus into which the CRISPR reporters described herein can be stably integrated is a safe harbor locus in the genome of the non-human animal. Interactions between integrated exogenous DNA and a host genome can limit the reliability and safety of integration and can lead to overt phenotypic effects that are not due to the targeted genetic modification but are instead due to unintended effects of the integration on surrounding endogenous genes. For example, randomly inserted transgenes can be subject to position effects and silencing, making their expression unreliable and unpredictable. Likewise, integration of exogenous DNA into a chromosomal locus can affect surrounding endogenous genes and chromatin, thereby altering cell behavior and phenotypes. Safe harbor loci include chromosomal loci where transgenes or other exogenous nucleic acid inserts can be stably and reliably expressed in all tissues of interest without overtly altering cell behavior or phenotype (i.e., without any deleterious effects on the host cell). See, e.g., Sadelain et al. (2012) *Nat. Rev. Cancer* 12:51-58, herein incorporated by reference in its entirety for all purposes. Optionally, the safe harbor locus is one in which expression of the inserted gene sequence is not perturbed by any read-through expression from neighboring genes. For example, safe harbor loci can include chromosomal loci where exogenous DNA can integrate and function in a predictable manner without adversely affecting endogenous gene structure or expression. Safe harbor loci can include extragenic regions or intragenic regions such as, for example, loci within genes that are non-essential, dispensable, or able to be disrupted without overt phenotypic consequences.

For example, the Rosa26 locus and its equivalent in humans offer an open chromatin configuration in all tissues and is ubiquitously expressed during embryonic development and in adults. See, e.g., Zambrowicz et al. (1997) *Proc. Natl. Acad. Sci. USA* 94:3789-3794, herein incorporated by reference in its entirety for all purposes. In addition, the Rosa26 locus can be targeted with high efficiency, and disruption of the Rosa26 gene produces no overt phenotype. Other examples of safe harbor loci include CCR5, HPRT, AAVS1, and albumin. See, e.g., U.S. Pat. Nos. 7,888,121; 7,972,854; 7,914,796; 7,951,925; 8,110,379; 8,409,861; 8,586,526; and US Patent Publication Nos. 2003/0232410; 2005/0208489; 2005/0026157; 2006/0063231; 2008/0159996; 2010/00218264; 2012/0017290; 2011/0265198; 2013/0137104; 2013/0122591; 2013/0177983; 2013/0177960; and 2013/0122591, each of which is herein incorporated by reference in its entirety for all purposes. Biallelic targeting of safe harbor loci such as the Rosa26 locus has no negative consequences, so different genes or reporters can be targeted to the two Rosa26 alleles. In one example, a CRISPR reporter is integrated into an intron of the Rosa26 locus, such as the first intron of the Rosa26 locus.

D. CRISPR/Cas Systems

CRISPR/Cas systems include transcripts and other elements involved in the expression of, or directing the activity of, Cas genes. A CRISPR/Cas system can be, for example, a type I, a type II, or a type III system. Alternatively, a CRISPR/Cas system can be a type V system (e.g., subtype V-A or subtype V-B). CRISPR/Cas systems used in the compositions and methods disclosed herein can be non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, non-naturally occurring CRISPR/Cas systems can employ CRISPR complexes comprising a gRNA and a Cas protein that do not naturally occur together, a Cas protein that does not occur naturally, or a gRNA that does not occur naturally.

(I) Cas Proteins and Polynucleotides Encoding Cas Proteins

Cas proteins generally comprise at least one RNA recognition or binding domain that can interact with guide RNAs (gRNAs, described in more detail below). Cas proteins can also comprise nuclease domains (e.g., DNase or RNase domains), DNA-binding domains, helicase domains, protein-protein interaction domains, dimerization domains, and other domains. Some such domains (e.g., DNase domains) can be from a native Cas protein. Other such domains can be added to make a modified Cas protein. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. For example, a wild type Cas9 protein will typically create a blunt cleavage product. Alternatively, a wild type Cpf1 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break at a target genomic locus (e.g., a double-strand break with blunt ends), or it can be a nickase that creates a single-strand break at a target genomic locus.

Examples of Cas proteins include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmrl, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

An exemplary Cas protein is a Cas9 protein or a protein derived from Cas9. Cas9 proteins are from a type II CRISPR/Cas system and typically share four key motifs with a conserved architecture. Motifs 1, 2, and 4 are RuvC-like motifs, and motif 3 is an HNH motif. Exemplary Cas9 proteins are from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum the rmopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Acaryochloris marina, Neisseria meningitidis*, or *Campylobacter jejuni*. Additional examples of the Cas9 family members are described in WO 2014/131833, herein incorporated by reference in its entirety for all purposes. Cas9 from *S. pyogenes* (SpCas9) (assigned SwissProt accession number Q99ZW2) is an exemplary Cas9 protein. Cas9 from *S. aureus* (SaCas9) (assigned UniProt accession number J7RUA5) is another exemplary Cas9 protein. Cas9 from *Campylobacter jejuni* (CjCas9) (assigned UniProt accession number Q0P897) is another exemplary Cas9 protein. See, e.g., Kim et al. (2017) *Nat. Comm.* 8:14500, herein incorporated by reference in its entirety for all purposes. SaCas9 is smaller than SpCas9, and CjCas9 is smaller than both SaCas9 and SpCas9. An exemplary Cas9 protein is set forth in SEQ ID NO: 53 (encoded by SEQ ID NO: 54).

Another example of a Cas protein is a Cpf1 (CRISPR from *Prevotella* and *Francisella* 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. See, e.g., Zetsche et al. (2015) *Cell* 163(3): 759-771, herein incorporated by reference in its entirety for all purposes. Exemplary Cpf1 proteins are from *Francisella tularensis* 1, *Francisella tularensis* subsp. *novicida, Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas creviorican is* 3, *Prevotella disiens*, and *Porphyromonas macacae*. Cpf1 from *Francisella novicida* U112 (FnCpf1; assigned UniProt accession number A0Q7Q2) is an exemplary Cpf1 protein.

Cas proteins can be wild type proteins (i.e., those that occur in nature), modified Cas proteins (i.e., Cas protein variants), or fragments of wild type or modified Cas proteins. Cas proteins can also be active variants or fragments with respect to catalytic activity of wild type or modified Cas proteins. Active variants or fragments with respect to catalytic activity can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can be modified to increase or decrease one or more of nucleic acid binding affinity, nucleic acid binding specificity, and enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity or a property of the Cas protein.

One example of a modified Cas protein is the modified SpCas9-HF1 protein, which is a high-fidelity variant of Streptococcus pyogenes Cas9 harboring alterations (N497A/R661A/Q695A/Q926A) designed to reduce non-specific DNA contacts. See, e.g., Kleinstiver et al. (2016) *Nature* 529(7587):490-495, herein incorporated by reference in its entirety for all purposes. Another example of a modified Cas protein is the modified eSpCas9 variant (K848A/K1003A/R1060A) designed to reduce off-target effects. See, e.g., Slaymaker et al. (2016) *Science* 351(6268):84-88, herein incorporated by reference in its entirety for all purposes. Other SpCas9 variants include K855A and K810A/K1003A/R1060A.

Cas proteins can comprise at least one nuclease domain, such as a DNase domain. For example, a wild type Cpf1 protein generally comprises a RuvC-like domain that cleaves both strands of target DNA, perhaps in a dimeric configuration. Cas proteins can also comprise at least two nuclease domains, such as DNase domains. For example, a wild type Cas9 protein generally comprises a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337:816-821, herein incorporated by reference in its entirety for all purposes.

One or more of the nuclease domains can be deleted or mutated so that they are no longer functional or have reduced nuclease activity. For example, if one of the nuclease domains is deleted or mutated in a Cas9 protein, the resulting Cas9 protein can be referred to as a nickase and can generate a single-strand break at a guide RNA target sequence within a double-stranded DNA but not a double-strand break (i.e., it can cleave the complementary strand or the non-complementary strand, but not both). An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839), H840A (histidine to alanine at amino acid position 840), or N863A (asparagine to alanine at amino acid position N863) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Research* 39:9275-9282 and WO 2013/141680, each of which is herein incorporated by reference in its entirety for all purposes. Such mutations can be generated using methods such as site-directed mutagenesis, PCR-mediated mutagenesis, or total gene synthesis. Examples of other mutations creating nickases can be found, for example, in WO 2013/176772 and WO 2013/142578, each of which is herein incorporated by reference in its entirety for all purposes.

Examples of inactivating mutations in the catalytic domains of *Staphylococcus aureus* Cas9 proteins are also known. For example, the *Staphyloccocus aureus* Cas9 enzyme (SaCas9) may comprise a substitution at position N580 (e.g., N580A substitution) and a substitution at position D10 (e.g., D10A substitution) to generate a nuclease-inactive Cas protein. See, e.g., WO 2016/106236, herein incorporated by reference in its entirety for all purposes.

Examples of inactivating mutations in the catalytic domains of Cpf1 proteins are also known. With reference to Cpf1 proteins from *Francisella novicida* U112 (FnCpf1), *Acidaminococcus* sp. BV3L6 (AsCpf1), *Lachnospiraceae bacterium* ND2006 (LbCpf1), and *Moraxella bovoculi* 237 (MbCpf1 Cpf1), such mutations can include mutations at positions 908, 993, or 1263 of AsCpf1 or corresponding positions in Cpf1 orthologs, or positions 832, 925, 947, or 1180 of LbCpf1 or corresponding positions in Cpf1 orthologs. Such mutations can include, for example one or more of mutations D908A, E993A, and D1263A of AsCpf1 or corresponding mutations in Cpf1 orthologs, or D832A, E925A, D947A, and D1180A of LbCpf1 or corresponding mutations in Cpf1 orthologs. See, e.g., US 2016/0208243, herein incorporated by reference in its entirety for all purposes.

Cas proteins can also be operably linked to heterologous polypeptides as fusion proteins. For example, a Cas protein can be fused to a cleavage domain or an epigenetic modification domain. See WO 2014/089290, herein incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein.

As one example, a Cas protein can be fused to one or more heterologous polypeptides that provide for subcellular localization. Such heterologous polypeptides can include, for example, one or more nuclear localization signals (NLS) such as the monopartite SV40 NLS and/or a bipartite alpha-importin NLS for targeting to the nucleus, a mitochondrial localization signal for targeting to the mitochondria, an ER retention signal, and the like. See, e.g., Lange et al. (2007) *J. Biol. Chem.* 282:5101-5105, herein incorporated by reference in its entirety for all purposes. Such subcellular localization signals can be located at the N-terminus, the C-terminus, or anywhere within the Cas protein. An NLS can comprise a stretch of basic amino acids, and can be a monopartite sequence or a bipartite sequence. Optionally, the Cas protein can comprise two or more NLSs, including an NLS (e.g., an alpha-importin NLS or a monopartite NLS) at the N-terminus and an NLS (e.g., an SV40 NLS or a bipartite NLS) at the C-terminus. A Cas protein can also comprise two or more NLSs at the N-terminus and/or two or more NLSs at the C-terminus.

Cas proteins can also be operably linked to a cell-penetrating domain or protein transduction domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, e.g., WO 2014/089290 and WO 2013/176772, each of which is herein incorporated by reference in its entirety for all purposes. The cell-penetrating domain can be located at the N-terminus, the C-terminus, or anywhere within the Cas protein.

Cas proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g., eBFP, eBFP2, Azurite, mKalama1, GFPuv, Sapphire, T-sapphire), cyan fluorescent proteins (e.g., eCFP, Cerulean, CyPet, AmCyan1, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (e.g., mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AUS, E, ECS, E2, FLAG, hemagglutinin (HA), nus, Softag 1, Softag 3, Strep, SBP, Glu-Glu, HSV, KT3, S, 51, T7, V5, VSV-G, histidine (His), biotin carboxyl carrier protein (BCCP), and calmodulin.

Cas proteins can also be tethered to exogenous donor nucleic acids or labeled nucleic acids. Such tethering (i.e., physical linking) can be achieved through covalent interactions or noncovalent interactions, and the tethering can be direct (e.g., through direct fusion or chemical conjugation, which can be achieved by modification of cysteine or lysine residues on the protein or intein modification), or can be achieved through one or more intervening linkers or adapter molecules such as streptavidin or aptamers. See, e.g., Pierce et al. (2005) *Mini Rev. Med. Chem.* 5(1):41-55; Duckworth et al. (2007) *Angew. Chem. Int. Ed. Engl.* 46(46):8819-8822; Schaeffer and Dixon (2009) *Australian J. Chem.* 62(10): 1328-1332; Goodman et al. (2009) *Chembiochem.* 10(9): 1551-1557; and Khatwani et al. (2012) *Bioorg. Med. Chem.*

20(14):4532-4539, each of which is herein incorporated by reference in its entirety for all purposes. Noncovalent strategies for synthesizing protein-nucleic acid conjugates include biotin-streptavidin and nickel-histidine methods. Covalent protein-nucleic acid conjugates can be synthesized by connecting appropriately functionalized nucleic acids and proteins using a wide variety of chemistries. Some of these chemistries involve direct attachment of the oligonucleotide to an amino acid residue on the protein surface (e.g., a lysine amine or a cysteine thiol), while other more complex schemes require post-translational modification of the protein or the involvement of a catalytic or reactive protein domain. Methods for covalent attachment of proteins to nucleic acids can include, for example, chemical cross-linking of oligonucleotides to protein lysine or cysteine residues, expressed protein-ligation, chemoenzymatic methods, and the use of photoaptamers. The exogenous donor nucleic acid or labeled nucleic acid can be tethered to the C-terminus, the N-terminus, or to an internal region within the Cas protein. Optionally, the exogenous donor nucleic acid or labeled nucleic acid is tethered to the C-terminus or the N-terminus of the Cas9 protein. Likewise, the Cas protein can be tethered to the 5' end, the 3' end, or to an internal region within the exogenous donor nucleic acid or labeled nucleic acid. That is, the exogenous donor nucleic acid or labeled nucleic acid can be tethered in any orientation and polarity. Optionally, the Cas protein is tethered to the 5' end or the 3' end of the exogenous donor nucleic acid or labeled nucleic acid.

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be can be codon optimized for efficient translation into protein in a particular cell or organism. For example, the nucleic acid encoding the Cas protein can be modified to substitute codons having a higher frequency of usage in a human cell, a non-human cell, a mammalian cell, a rodent cell, a mouse cell, a rat cell, or any other host cell of interest, as compared to the naturally occurring polynucleotide sequence. When a nucleic acid encoding the Cas protein is introduced into the cell, the Cas protein can be transiently, conditionally, or constitutively expressed in the cell.

Cas proteins provided as mRNAs can be modified for improved stability and/or immunogenicity properties. The modifications may be made to one or more nucleosides within the mRNA. Examples of chemical modifications to mRNA nucleobases include pseudouridine, 1-methyl-pseudouridine, and 5-methyl-cytidine. For example, capped and polyadenylated Cas mRNA containing N1-methyl pseudouridine can be used. Likewise, Cas mRNAs can be modified by depletion of uridine using synonymous codons.

Nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a vector comprising a DNA encoding a gRNA. Alternatively, it can be in a vector or plasmid that is separate from the vector comprising the DNA encoding the gRNA. Promoters that can be used in an expression construct include promoters active, for example, in one or more of a eukaryotic cell, a human cell, a non-human cell, a mammalian cell, a non-human mammalian cell, a rodent cell, a mouse cell, a rat cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allow for the generation of compact expression cassettes to facilitate delivery.

(2) Guide RNAs

A "guide RNA" or "gRNA" is an RNA molecule that binds to a Cas protein (e.g., Cas9 protein) and targets the Cas protein to a specific location within a target DNA. Guide RNAs can comprise two segments: a "DNA-targeting segment" and a "protein-binding segment." "Segment" includes a section or region of a molecule, such as a contiguous stretch of nucleotides in an RNA. Some gRNAs, such as those for Cas9, can comprise two separate RNA molecules: an "activator-RNA" (e.g., tracrRNA) and a "targeter-RNA" (e.g., CRISPR RNA or crRNA). Other gRNAs are a single RNA molecule (single RNA polynucleotide), which can also be called a "single-molecule gRNA," a "single-guide RNA," or an "sgRNA." See, e.g., WO 2013/176772, WO 2014/065596, WO 2014/089290, WO 2014/093622, WO 2014/099750, WO 2013/142578, and WO 2014/131833, each of which is herein incorporated by reference in its entirety for all purposes. For Cas9, for example, a single-guide RNA can comprise a crRNA fused to a tracrRNA (e.g., via a linker). For Cpf1, for example, only a crRNA is needed to achieve binding to and/or cleavage of a target sequence. The terms "guide RNA" and "gRNA" include both double-molecule (i.e., modular) gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A crRNA comprises both the DNA-targeting segment (single-stranded) of the gRNA and a stretch of nucleotides (i.e., the crRNA tail) that forms one half of the dsRNA duplex of the protein-binding segment of the gRNA. An example of a crRNA tail, located downstream (3') of the DNA-targeting segment, comprises, consists essentially of, or consists of GUUUUAGAGCUAUGCU (SEQ ID NO: 37). Any of the DNA-targeting segments (i.e., guide sequences or guides) disclosed herein (e.g., SEQ ID NO: 2, 14, 20, 22, 24, 26, 28, 29, 30, 31, 35, 36, or 55) can be joined to the 5' end of SEQ ID NO: 37 to form a crRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA. An example of a tracrRNA sequence comprises, consists essentially of, or consists of AGCAUAGCAAGUUAAAAUAAGGCUAGU-CCGUUAUCAACUUGAAAAAGUGGCACC GAGUCG-GUGCUUU (SEQ ID NO: 38).

In systems in which both a crRNA and a tracrRNA are needed, the crRNA and the corresponding tracrRNA hybridize to form a gRNA. In systems in which only a crRNA is needed, the crRNA can be the gRNA. The crRNA additionally provides the single-stranded DNA-targeting segment that targets a guide RNA target sequence by hybridizing to the opposite strand (i.e., the complementary strand). If used for modification within a cell, the exact sequence of a given crRNA or tracrRNA molecule can be designed to be specific to the species in which the RNA molecules will be used. See, e.g., Mali et al. (2013) *Science* 339:823-826; Jinek et al. (2012) *Science* 337:816-821; Hwang et al. (2013) *Nat. Biotechnol.* 31:227-229; Jiang et al. (2013) *Nat. Biotechnol.* 31:233-239; and Cong et al. (2013) *Science* 339:819-823, each of which is herein incorporated by reference in its entirety for all purposes.

The DNA-targeting segment (crRNA) of a given gRNA comprises a nucleotide sequence that is complementary to a sequence (i.e., the complementary strand of the guide RNA recognition sequence on the strand opposite of the guide RNA target sequence) in a target DNA. The DNA-targeting segment of a gRNA interacts with a target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR/Cas system and organism but often contain a targeting segment of between 21 to 72 nucleotides length, flanked by two direct repeats (DR) of a length of between 21 to 46 nucleotides (see, e.g., WO 2014/131833, herein incorporated by reference in its entirety for all purposes). In the case of *S. pyogenes*, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have a length of at least about 12 nucleotides, at least about 15 nucleotides, at least about 17 nucleotides, at least about 18 nucleotides, at least about 19 nucleotides, at least about 20 nucleotides, at least about 25 nucleotides, at least about 30 nucleotides, at least about 35 nucleotides, or at least about 40 nucleotides. Such DNA-targeting segments can have a length from about 12 nucleotides to about 100 nucleotides, from about 12 nucleotides to about 80 nucleotides, from about 12 nucleotides to about 50 nucleotides, from about 12 nucleotides to about 40 nucleotides, from about 12 nucleotides to about 30 nucleotides, from about 12 nucleotides to about 25 nucleotides, or from about 12 nucleotides to about 20 nucleotides. For example, the DNA targeting segment can be from about 15 nucleotides to about 25 nucleotides (e.g., from about 17 nucleotides to about 20 nucleotides, or about 17 nucleotides, about 18 nucleotides, about 19 nucleotides, or about 20 nucleotides). See, e.g., US 2016/0024523, herein incorporated by reference in its entirety for all purposes. For Cas9 from *S. pyogenes*, a typical DNA-targeting segment is between 16 and 20 nucleotides in length or between 17 and 20 nucleotides in length. For Cas9 from *S. aureus*, a typical DNA-targeting segment is between 21 and 23 nucleotides in length. For Cpf1, a typical DNA-targeting segment is at least 16 nucleotides in length or at least 18 nucleotides in length.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise, consist essentially of, or consist of all or a portion of a wild type tracrRNA sequence (e.g., about or more than about 20, 26, 32, 45, 48, 54, 63, 67, 85, or more nucleotides of a wild type tracrRNA sequence). Examples of wild type tracrRNA sequences from *S. pyogenes* include 171-nucleotide, 89-nucleotide, 75-nucleotide, and 65-nucleotide versions. See, e.g., Deltcheva et al. (2011) *Nature* 471:602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild type tracrRNA is included in the sgRNA. See U.S. Pat. No. 8,697,359, herein incorporated by reference in its entirety for all purposes.

The percent complementarity between the DNA-targeting segment and the complementary strand of the guide RNA recognition sequence within the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting segment and the complementary strand of the guide RNA recognition sequence within the target DNA can be at least 60% over about 20 contiguous nucleotides. As an example, the percent complementarity between the DNA-targeting segment and the complementary strand of the guide RNA recognition sequence within the target DNA is 100% over the 14 contiguous nucleotides at the 5' end of the complementary strand of the guide RNA recognition sequence within the complementary strand of the target DNA and as low as 0% over the remainder. In such a case, the DNA-targeting segment can be considered to be 14 nucleotides in length. As another example, the percent complementarity between the DNA-targeting segment and the complementary strand of the guide RNA recognition sequence within the target DNA is 100% over the seven contiguous nucleotides at the 5' end of the complementary strand of the guide RNA recognition sequence within the complementary strand of the target DNA and as low as 0% over the remainder. In such a case, the DNA-targeting segment can be considered to be 7 nucleotides in length. In some guide RNAs, at least 17 nucleotides within the DNA-targeting segment are complementary to the target DNA. For example, the DNA-targeting segment can be 20 nucleotides in length and can comprise 1, 2, or 3 mismatches with the complementary strand of the guide RNA recognition sequence. Optionally, the mismatches are not adjacent to a protospacer adjacent motif (PAM) sequence (e.g., the mismatches are in the 5' end of the DNA-targeting segment, or the mismatches are at least 2, 3, 4, 5, 6, 7, 8, 9, 10, 11, 12, 13, 14, 15, 16, 17, 18, or 19 base pairs away from the PAM sequence).

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Single-guide RNAs have the DNA-targeting segment and a scaffold sequence (i.e., the protein-binding or Cas-binding sequence of the guide RNA). For example, such guide RNAs have a 5' DNA-targeting segment and a 3' scaffold sequence. Exemplary scaffold sequences comprise, consist essentially of, or consist of: GUUUUAGAGCUA-GAAAUAGCAAGUUAAAAUAAGGCUAGU-CCGUUAUCAACUUGA AAAAGUGGCACCGAGUCG-GUGCU (version 1; SEQ ID NO: 39); GUUGGAACCAUUCAAAACAG-CAUAGCAAGUUAAAAUAAGGCUAGU-CCGUUAUCA ACUUGAAAAAGUGGCACCGAGUCG-GUGC (version 2; SEQ ID NO: 7); GUUUUAGAGCUA-GAAAUAGCAAGUUAAAAUAAGGCUAGU-CCGUUAUCAACUUGA AAAAGUGGCACCGAGUCG-GUGC (version 3; SEQ ID NO: 8); and GUUUAAGAGCUAUGCUGGAAACAG-CAUAGCAAGUUUAAAUAAGGCUAGUCCGUU AUCAACUUGAAAAAGUGGCACCGAGUCGGUGC (version 4; SEQ ID NO: 9). Guide RNAs targeting any guide RNA target sequence can include, for example, a DNA-targeting segment on the 5' end of the guide RNA fused to any of the exemplary guide RNA scaffold sequences on the 3' end of the guide RNA. That is, any of the DNA-targeting segments (i.e., guide sequences or guides) disclosed herein (e.g., SEQ ID NO: 2, 14, 20, 22, 24, 26, 28, 29, 30, 31, 35, 36, or 55) can be joined to the 5' end of any one of SEQ ID NOS: 39, 7, 8, or 9 to form a single guide RNA (chimeric guide RNA). Guide RNA versions 1, 2, 3, and 4 as disclosed elsewhere herein refer to DNA-targeting segments (i.e., guide sequences or guides) joined with scaffold versions 1, 2, 3, and 4, respectively.

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including DNA methyltransferases, DNA demethylases, histone acetyltransferases, histone deacetylases, and the like); and combinations thereof. Other examples of modifications include engineered stem loop duplex structures, engineered bulge regions, engineered hairpins 3' of the stem loop duplex structure, or any combination thereof. See, e.g., US 2015/0376586, herein incorporated by reference in its entirety for all purposes. A bulge can be an unpaired region of nucleotides within the duplex made up of the crRNA-like region and the minimum tracrRNA-like region. A bulge can comprise, on one side of the duplex, an unpaired 5'-XXXY-3' where X is any purine and Y can be a nucleotide that can form a wobble pair with a nucleotide on the opposite strand, and an unpaired nucleotide region on the other side of the duplex.

Unmodified nucleic acids can be prone to degradation. Exogenous nucleic acids can also induce an innate immune response. Modifications can help introduce stability and reduce immunogenicity. Guide RNAs can comprise modified nucleosides and modified nucleotides including, for example, one or more of the following: (1) alteration or replacement of one or both of the non-linking phosphate oxygens and/or of one or more of the linking phosphate oxygens in the phosphodiester backbone linkage; (2) alteration or replacement of a constituent of the ribose sugar such as alteration or replacement of the 2' hydroxyl on the ribose sugar; (3) replacement of the phosphate moiety with dephospho linkers; (4) modification or replacement of a naturally occurring nucleobase; (5) replacement or modification of the ribose-phosphate backbone; (6) modification of the 3' end or 5' end of the oligonucleotide (e.g., removal, modification or replacement of a terminal phosphate group or conjugation of a moiety); and (7) modification of the sugar. Other possible guide RNA modifications include modifications of or replacement of uracils or poly-uracil tracts. See, e.g., WO 2015/048577 and US 2016/0237455, each of which is herein incorporated by reference in its entirety for all purposes. Similar modifications can be made to Cas-encoding nucleic acids, such as Cas mRNAs.

As one example, nucleotides at the 5' or 3' end of a guide RNA can include phosphorothioate linkages (e.g., the bases can have a modified phosphate group that is a phosphorothioate group). For example, a guide RNA can include phosphorothioate linkages between the 2, 3, or 4 terminal nucleotides at the 5' or 3' end of the guide RNA. As another example, nucleotides at the 5' and/or 3' end of a guide RNA can have 2'-O-methyl modifications. For example, a guide RNA can include 2'-O-methyl modifications at the 2, 3, or 4 terminal nucleotides at the 5' and/or 3' end of the guide RNA (e.g., the 5' end). See, e.g., WO 2017/173054 A1 and Finn et al. (2018) *Cell Reports* 22:1-9, each of which is herein incorporated by reference in its entirety for all purposes. In one specific example, the guide RNA comprises 2'-O-methyl analogs and 3' phosphorothioate internucleotide linkages at the first three 5' and 3' terminal RNA residues. In another specific example, the guide RNA is modified such that all 2'OH groups that do not interact with the Cas9 protein are replaced with 2'-O-methyl analogs, and the tail region of the guide RNA, which has minimal interaction with Cas9, is modified with 5' and 3' phosphorothioate internucleotide linkages. See, e.g., Yin et al. (2017) *Nat. Biotech.* 35(12): 1179-1187, herein incorporated by reference in its entirety for all purposes.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively.

When a gRNA is provided in the form of DNA, the gRNA can be transiently, conditionally, or constitutively expressed in the cell. DNAs encoding gRNAs can be operably linked to a promoter in an expression construct. For example, the DNA encoding the gRNA can be in a vector comprising a heterologous nucleic acid, such as a nucleic acid encoding a Cas protein. Alternatively, it can be in a vector or a plasmid that is separate from the vector comprising the nucleic acid encoding the Cas protein. Promoters that can be used in such expression constructs include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Such promoters can also be, for example, bidirectional promoters. Specific examples of suitable promoters include an RNA polymerase III promoter, such as a human U6 promoter, a rat U6 polymerase III promoter, or a mouse U6 polymerase III promoter.

Alternatively, gRNAs can be prepared by various other methods. For example, gRNAs can be prepared by in vitro transcription using, for example, T7 RNA polymerase (see, e.g., WO 2014/089290 and WO 2014/065596, each of which is herein incorporated by reference in its entirety for all purposes). Guide RNAs can also be a synthetically produced molecule prepared by chemical synthesis.

(3) Guide RNA Recognition Sequences and Guide RNA Target Sequences

The term "guide RNA recognition sequence" includes nucleic acid sequences present in a target DNA to which a DNA-targeting segment of a gRNA will bind, provided sufficient conditions for binding exist. The term guide RNA recognition sequence as used herein encompasses both strands of the target double-stranded DNA (i.e., the sequence on the complementary strand to which the guide RNA hybridizes and the corresponding sequence on the non-complementary strand adjacent to the protospacer adjacent motif (PAM)). The term "guide RNA target sequence" as used herein refers specifically to the sequence on the non-complementary strand adjacent to the PAM (i.e., upstream or 5' of the PAM). That is, the guide RNA target sequence refers to the sequence on the non-complementary strand corresponding to the sequence to which the guide RNA hybridizes on the complementary strand. A guide RNA target sequence is equivalent to the DNA-targeting segment of a guide RNA, but with thymines instead of uracils. As one example, a guide RNA target sequence for a Cas9 enzyme would refer to the sequence on the non-complementary strand adjacent to the 5'-NGG-3' PAM. Guide RNA recognition sequences include sequences to which a guide RNA is designed to have complementarity, where hybridization between the complementary strand of a guide RNA recognition sequence and a DNA-targeting segment of a guide RNA promotes the formation of a CRISPR complex. Full complementarity is not necessarily required, provided that there is sufficient complementarity to cause hybridization and promote formation of a CRISPR complex. Guide RNA recognition sequences or guide RNA target sequences also include cleavage sites for Cas proteins, described in more detail below. A guide RNA recognition sequence or a guide RNA target sequence can comprise any polynucleotide, which can be located, for example, in the nucleus or cytoplasm of a cell or within an organelle of a cell, such as a mitochondrion or chloroplast.

The guide RNA recognition sequence within a target DNA can be targeted by (i.e., be bound by, or hybridize with, or be complementary to) a Cas protein or a gRNA. Suitable DNA/RNA binding conditions include physiological conditions normally present in a cell. Other suitable DNA/RNA binding conditions (e.g., conditions in a cell-free system) are known (see, e.g., Molecular Cloning: A Laboratory Manual, 3rd Ed. (Sambrook et al., Harbor Laboratory Press 2001), herein incorporated by reference in its entirety for all purposes). The strand of the target DNA that is complementary to and hybridizes with the Cas protein or gRNA can be called the "complementary strand," and the strand of the target DNA that is complementary to the "complementary strand" (and is therefore not complementary to the Cas protein or gRNA) can be called "noncomplementary strand" or "template strand."

The Cas protein can cleave the nucleic acid at a site within or outside of the nucleic acid sequence present in the target DNA to which the DNA-targeting segment of a gRNA will bind. The "cleavage site" includes the position of a nucleic acid at which a Cas protein produces a single-strand break or a double-strand break. For example, formation of a CRISPR complex (comprising a gRNA hybridized to the complementary strand of a guide RNA recognition sequence and complexed with a Cas protein) can result in cleavage of one or both strands in or near (e.g., within 1, 2, 3, 4, 5, 6, 7, 8, 9, 10, 20, 50, or more base pairs from) the nucleic acid sequence present in a target DNA to which a DNA-targeting segment of a gRNA will bind. If the cleavage site is outside of the nucleic acid sequence to which the DNA-targeting segment of the gRNA will bind, the cleavage site is still considered to be within the "guide RNA recognition sequence" or guide RNA target sequence. The cleavage site can be on only one strand or on both strands of a nucleic acid. Cleavage sites can be at the same position on both strands of the nucleic acid (producing blunt ends) or can be at different sites on each strand (producing staggered ends (i.e., overhangs)). Staggered ends can be produced, for example, by using two Cas proteins, each of which produces a single-strand break at a different cleavage site on a different strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the guide RNA recognition sequence or guide RNA target sequence of the nickase on the first strand is separated from the guide RNA recognition sequence or guide RNA target sequence of the nickase on the second strand by at least 2, 3, 4, 5, 6, 7, 8, 9, 10, 15, 20, 25, 30, 40, 50, 75, 100, 250, 500, or 1,000 base pairs.

Site-specific binding and/or cleavage of target DNA by Cas proteins can occur at locations determined by both (i) base-pairing complementarity between the gRNA and the target DNA and (ii) a short motif, called the protospacer adjacent motif (PAM), in the target DNA. The PAM can flank the guide RNA target sequence on the non-complementary strand opposite of the strand to which the guide RNA hybridizes. Optionally, the guide RNA target sequence can be flanked on the 3' end by the PAM. Alternatively, the guide RNA target sequence can be flanked on the 5' end by the PAM. For example, the cleavage site of Cas proteins can be about 1 to about 10 or about 2 to about 5 base pairs (e.g., 3 base pairs) upstream or downstream of the PAM sequence. In some cases (e.g., when Cas9 from *S. pyogenes* or a closely related Cas9 is used), the PAM sequence of the non-complementary strand can be 5'-$N_1$GG-3', where $N_1$ is any DNA nucleotide and is immediately 3' of the guide RNA recognition sequence of the non-complementary strand of the target DNA (i.e., immediately 3' of the guide RNA target sequence). As such, the PAM sequence of the complementary strand would be 5'-CCN$_2$-3', where N$_2$ is any DNA nucleotide and is immediately 5' of the guide RNA recognition sequence of the complementary strand of the target DNA. In some such cases, N$_1$ and N$_2$ can be complementary and the N$_1$-N$_2$ base pair can be any base pair (e.g., N$_1$=C and N$_2$=G; N$_1$=G and N$_2$=C; N$_1$=A and N$_2$=T; or N$_1$=T, and N$_2$=A). In the case of Cas9 from *S. aureus*, the PAM can be NNGRRT or NNGRR, where N can A, G, C, or T, and R can be G or A. In the case of Cas9 from *C. jejuni*, the PAM can be, for example, NNNNACAC or NNNNRYAC, where N can be A, G, C, or T, and R can be G or A. In some cases (e.g., for FnCpf1), the PAM sequence can be upstream of the 5' end and have the sequence 5'-TTN-3'.

Examples of guide RNA target sequences or guide RNA target sequences in addition to a PAM sequence are provided below. For example, the guide RNA target sequence can be a 20-nucleotide DNA sequence immediately preceding an NGG motif recognized by a Cas9 protein. Examples of such guide RNA target sequences plus a PAM sequence are GN$_{19}$NGG (SEQ ID NO: 10) or N$_{20}$NGG (SEQ ID NO: 11). See, e.g., WO 2014/165825, herein incorporated by reference in its entirety for all purposes. The guanine at the 5' end can facilitate transcription by RNA polymerase in cells. Other examples of guide RNA target sequences plus a PAM sequence can include two guanine nucleotides at the 5' end (e.g., GGN$_{20}$NGG; SEQ ID NO: 12) to facilitate efficient transcription by T7 polymerase in vitro. See, e.g., WO 2014/065596, herein incorporated by reference in its entirety for all purposes. Other guide RNA target sequences plus a PAM sequence can have between 4-22 nucleotides in length of SEQ ID NOS: 10-12, including the 5' G or GG and the 3' GG or NGG. Yet other guide RNA target sequences can have between 14 and 20 nucleotides in length of SEQ ID NOS: 10-12.

The guide RNA recognition sequence or guide RNA target sequence can be any nucleic acid sequence endogenous or exogenous to a cell. The guide RNA recognition sequence or guide RNA target sequence can be a sequence coding a gene product (e.g., a protein) or a non-coding sequence (e.g., a regulatory sequence) or can include both.

III. Methods of Assessing CRISPR/Cas Activity In Vivo

Various methods are provided for assessing CRISPR/Cas delivery to and for assessing CRISPR/Cas activity in tissues and organs of a live animal. Such methods make use of non-human animals comprising a CRISPR reporter as described elsewhere herein.

A. Methods of Testing Ability of CRISPR/Cas to Excise or Disrupt a Target Genomic Nucleic Acid In Vivo or Ex Vivo Various methods are provided for assessing CRISPR/Cas-induced NHEJ activity in vivo using non-human animals comprising a CRISPR reporter as described elsewhere herein. Such methods can comprise introducing into the non-human animal: (i) a first guide RNA designed to target the first guide RNA target sequence in the CRISPR reporter; (ii) a second guide RNA designed to target the second guide RNA target sequence in the CRISPR reporter; and (iii) a Cas protein (e.g., a Cas9 protein); and (b) measuring the activity or expression of at least one of the one or more different reporter proteins. Optionally, the first guide RNA and the second guide RNA can be identical, and the first guide RNA target sequence and the second guide RNA target sequence can be identical. Alternatively, the first guide RNA and the second guide RNA can be different, and the first guide RNA target sequence and the second guide RNA target sequence can be different. Activity or expression of the reporter proteins will be induced when the first guide RNA forms a complex with the Cas protein and directs the Cas protein to the CRISPR reporter, the second guide RNA forms a complex with the Cas protein and directs the Cas protein to the CRISPR reporter, the first Cas/guide RNA complex cleaves the first guide RNA target sequence, and the second Cas/guide RNA complex cleaves the second guide RNA target sequence, resulting in excision of the polyadenylation signal or transcription terminator upstream of the one or more reporter proteins. Alternatively, if the first or second guide RNA target sequence or a third guide RNA target sequence is at or near the poly A recognition motif (canonical polyadenylation hexamer AATAAA), a single guide RNA can be introduced instead of the pair of first and second guide RNAs, and the single guide RNA forms a complex with the Cas protein and directs the Cas protein to the CRISPR reporter, the Cas/guide RNA complex cleaves the guide RNA target sequence at or near the canonical polyadenylation hexamer, resulting in disruption of the canonical polyadenylation hexamer and consequently disruption of the polyadenylation signal or transcription terminator upstream of the one or more reporter proteins.

Likewise, the various methods provided above for assessing CRISPR/Cas activity in vivo can also be used to assess CRISPR/Cas activity ex vivo using cells comprising a CRISPR reporter as described elsewhere herein.

Guide RNAs and Cas proteins can be introduced into the cell or non-human animal via any delivery method (e.g., AAV, LNP, or HDD) and any route of administration as disclosed elsewhere herein. In particular methods, the guide RNA (or guide RNAs) is delivered via AAV-mediated delivery. For example, AAV8 can be used if the liver is being targeted. In one specific example, Cas9, gRNAs, and optionally exogenous donor nucleic acid (e.g., ssODN) are delivered via AAV8 as disclosed elsewhere herein. In another specific example, Cas9 mRNA and gRNAs (in the form of RNA) and optionally exogenous donor nucleic acid are delivered via LNP as disclosed elsewhere herein.

Methods for assessing modification of the target genomic locus are provided elsewhere herein and are well known. Assessment of modification of the target genomic locus can be in any cell type, any tissue type, or any organ type as disclosed elsewhere herein. In some methods, modification of the target genomic locus is assessed in liver cells.

B. Methods of Optimizing Ability of CRISPR/Cas to Excise a Target Genomic Nucleic Acid In Vivo or Ex Vivo Various methods are provided for optimizing delivery of CRISPR/Cas to a cell or non-human animal or optimizing CRISPR/Cas-induced NHEJ activity in vivo or ex vivo. Such methods can comprise, for example: (a) performing the method of testing the ability of CRISPR/Cas to excise the polyadenylation signal or transcription terminator in the CRISPR reporter as described elsewhere herein a first time in a first non-human animal; (b) changing a variable and performing the method a second time with the changed variable in a second non-human animal (i.e., of the same species); and (c) comparing the activity or expression of at least one of the one or more reporter proteins in step (a) with the activity or expression of the at least one of the one or more different proteins in step (b), and selecting the method resulting in the higher activity or expression of the at least one of the one or more different reporter proteins (i.e., the method resulting in higher efficacy).

Alternatively, the method selected in step (c) can be the method resulting in targeted modification of the CRISPR reporter or increased activity or expression of the at least one of the one or more different reporter proteins with higher efficacy, higher precision, higher consistency, or higher specificity. Higher efficacy refers to higher levels of modification of the target locus in the CRISPR reporter (e.g., a higher percentage of cells is targeted within a particular target cell type, within a particular target tissue, or within a particular target organ). Higher precision refers to more precise modification of the target locus in the CRISPR reporter (e.g., a higher percentage of targeted cells having the same modification or having the desired modification without extra unintended insertions and deletions (e.g., NHEJ indels)). Higher consistency refers to more consistent modification of the target locus in the CRISPR reporter among different types of targeted cells, tissues, or organs if more than one type of cell, tissue, or organ is being targeted (e.g., modification of a greater number of cell types within a target organ). If a particular organ is being targeted, higher consistency can also refer to more consistent modification throughout all locations within the organ. Higher specificity can refer to higher specificity with respect to the locus targeted within the CRISPR reporter, higher specificity with respect to the cell type targeted, higher specificity with respect to the tissue type targeted, or higher specificity with respect to the organ targeted. For example, increased locus specificity refers to less modification of off-target genomic loci (e.g., a lower percentage of targeted cells having modifications at unintended, off-target genomic loci instead of or in addition to modification of the target locus in the CRISPR reporter). Likewise, increased cell type, tissue, or organ type specificity refers to less modification of off-target cell types, tissue types, or organ types if a particular cell type, tissue type, or organ type is being targeted (e.g., when a particular organ is targeted (e.g., the liver), there is less modification of cells in organs or tissues that are not intended targets).

The variable that is changed can be any parameter. As one example, the changed variable can be the packaging or the delivery method by which one or more or all of the guide RNAs and the Cas protein are introduced into the cell or non-human animal. Examples of delivery methods, such as LNP, HDD, and AAV, are disclosed elsewhere herein. As another example, the changed variable can be the route of administration for introduction of one or more or all of the guide RNAs and the Cas protein into the non-human animal. Examples of routes of administration, such as intravenous, intravitreal, intraparenchymal, and nasal instillation, are disclosed elsewhere herein.

As another example, the changed variable can be the concentration or amount of one or more or all of the guide RNAs introduced and the Cas protein introduced. As another example, the changed variable can be the concentration or the amount of guide RNAs introduced relative to the concentration or the amount of Cas protein introduced.

As another example, the changed variable can be the timing of introducing one or more or all of the guide RNAs and the Cas protein relative to the timing of measuring expression or activity of the one or more reporter proteins. As another example, the changed variable can be the number of times or frequency with which one or more or all of the guide RNA and the Cas protein are introduced. As another example, the changed variable can be the timing of introduction of guide RNAs relative to the timing of introduction of Cas protein.

As another example, the changed variable can be the form in which one or more or all of the guide RNAs and the Cas protein are introduced. For example, the guide RNAs can be introduced in the form of DNA or in the form of RNA. The Cas protein can be introduced in the form of DNA, RNA, or protein. Similarly, each of the components can comprise various combinations of modifications for stability, to reduce off-target effects, to facilitate delivery, and so forth. As another example, the changed variable can be one or more or all of the guide RNAs that are introduced (e.g., introducing a different guide RNA with a different sequence) and the Cas protein that is introduced (e.g., introducing a different Cas protein with a different sequence, or a nucleic acid with a different sequence but encoding the same Cas protein amino acid sequence).

C. Methods of Testing Ability of CRISPR/Cas to Induce Recombination of a Target Genomic Nucleic Acid with an Exogenous Donor Nucleic Acid In Vivo or Ex Vivo Various methods are provided for assessing CRISPR/Cas-induced recombination activity in vivo using non-human animals comprising a CRISPR reporter as described elsewhere herein. If the CRISPR reporter is a CRISPR reporter comprising a polyadenylation signal upstream of the coding sequences for the reporter protein(s), optionally the polyadenylation signal has been removed through CRISPR/Cas-mediated excision or recombinase-mediated excision. Such methods can comprise introducing into the non-human animal: (i) a guide RNA designed to target a guide RNA target sequence in the CRISPR reporter; (ii) a Cas protein (e.g., a Cas9 protein); and (iii) an exogenous donor nucleic acid capable of recombining with the CRISPR reporter and changing the coding sequence for a reporter protein within the CRISPR reporter into a coding sequence for a different reporter protein; and (b) measuring the activity or expression of the different reporter protein. The guide RNA target sequence can be, for example, within the coding sequence for the reporter protein being modified. Optionally, the Cas protein can be tethered to the exogenous donor nucleic acid as described elsewhere herein. Activity or expression of the reporter proteins will be induced when the guide RNA forms a complex with the Cas protein and directs the Cas protein to the CRISPR reporter, the Cas/guide RNA complex cleaves the guide RNA target sequence, and the CRISPR reporter recombines with the exogenous donor nucleic acid to convert the coding sequence for the reporter protein within the CRISPR reporter into a coding sequence for a different reporter protein. The exogenous donor nucleic acid can recombine with the CRISPR reporter, for example, via homology-directed repair (HDR) or via NHEJ-mediated insertion. Any type of exogenous donor nucleic acid can be used, examples of which are provided elsewhere herein.

Likewise, the various methods provided above for assessing CRISPR/Cas activity in vivo can also be used to assess CRISPR/Cas activity ex vivo using cells comprising a CRISPR reporter as described elsewhere herein.

In one example, the reporter protein is BFP or eBFP, and the exogenous donor nucleic acid comprises mutations to convert the BFP or eBFP coding sequence into a GFP or eGFP coding sequence by altering a single codon. An exemplary guide RNA targeting this region of the BFP or eBFP coding sequence comprises the targeting sequence set forth in SEQ ID NO: 42. The sequence for an exemplary exogenous donor nucleic acid is set forth in SEQ ID NO: 15 or SEQ ID NO: 16. In another example, the reporter protein is GFP or eGFP, and the exogenous donor nucleic acid comprises mutations to convert the GFP or eGFP coding sequence into a BFP or eBFP coding sequence by altering a single codon.

Guide RNAs, Cas proteins, and exogenous donor nucleic acids can be introduced into the cell or non-human animal via any delivery method (e.g., AAV, LNP, or HDD) and any route of administration as disclosed elsewhere herein. In particular methods, the guide RNA (or guide RNAs) is delivered via AAV-mediated delivery. For example, AAV8 can be used if the liver is being targeted.

Methods for assessing modification of the target genomic locus are provided elsewhere herein and are well known. Assessment of modification of the target genomic locus can be in any cell type, any tissue type, or any organ type as disclosed elsewhere herein. In some methods, modification of the target genomic locus is assessed in liver cells.

(I) Exogenous Donor Nucleic Acids

The methods and compositions disclosed herein utilize exogenous donor nucleic acids to modify the CRISPR reporter (i.e., the target genomic locus) following cleavage of the CRISPR reporter with a Cas protein. In such methods, the Cas protein cleaves the CRISPR reporter to create a single-strand break (nick) or double-strand break, and the exogenous donor nucleic acid recombines the target nucleic acid via non-homologous end joining (NHEJ)-mediated ligation or through a homology-directed repair event. Optionally, repair with the exogenous donor nucleic acid removes or disrupts the guide RNA target sequence or the Cas cleavage site so that alleles that have been targeted cannot be re-targeted by the Cas protein.

Exogenous donor nucleic acids can comprise deoxyribonucleic acid (DNA) or ribonucleic acid (RNA), they can be single-stranded or double-stranded, and they can be in linear or circular form. For example, an exogenous donor nucleic acid can be a single-stranded oligodeoxynucleotide (ssODN). See, e.g., Yoshimi et al. (2016) *Nat. Commun.* 7:10431, herein incorporated by reference in its entirety for all purposes. An exemplary exogenous donor nucleic acid is between about 50 nucleotides to about 5 kb in length, is between about 50 nucleotides to about 3 kb in length, or is between about 50 to about 1,000 nucleotides in length. Other exemplary exogenous donor nucleic acids are between about 40 to about 200 nucleotides in length. For example, an exogenous donor nucleic acid can be between about 50-60, 60-70, 70-80, 80-90, 90-100, 100-110, 110-120, 120-130, 130-140, 140-150, 150-160, 160-170, 170-180, 180-190, or 190-200 nucleotides in length. Alternatively, an exogenous donor nucleic acid can be between about 50-100, 100-200, 200-300, 300-400, 400-500, 500-600, 600-700, 700-800, 800-900, or 900-1000 nucleotides in length. Alternatively, an exogenous donor nucleic acid can be between about 1-1.5, 1.5-2, 2-2.5, 2.5-3, 3-3.5, 3.5-4, 4-4.5, or 4.5-5 kb in length. Alternatively, an exogenous donor nucleic acid can be, for example, no more than 5 kb, 4.5 kb, 4 kb, 3.5 kb, 3 kb, 2.5 kb, 2 kb, 1.5 kb, 1 kb, 900 nucleotides, 800 nucleotides, 700 nucleotides, 600 nucleotides, 500 nucleotides, 400 nucleotides, 300 nucleotides, 200 nucleotides, 100 nucleotides, or 50 nucleotides in length. Exogenous donor nucleic acids (e.g., targeting vectors) can also be longer.

In one example, an exogenous donor nucleic acid is an ssODN that is between about 80 nucleotides and about 200 nucleotides in length. In another example, an exogenous donor nucleic acids is an ssODN that is between about 80 nucleotides and about 3 kb in length. Such an ssODN can have homology arms, for example, that are each between about 40 nucleotides and about 60 nucleotides in length. Such an ssODN can also have homology arms, for example, that are each between about 30 nucleotides and 100 nucleotides in length. The homology arms can be symmetrical (e.g., each 40 nucleotides or each 60 nucleotides in length), or they can be asymmetrical (e.g., one homology arm that is 36 nucleotides in length, and one homology arm that is 91 nucleotides in length).

Exogenous donor nucleic acids can include modifications or sequences that provide for additional desirable features (e.g., modified or regulated stability; tracking or detecting with a fluorescent label; a binding site for a protein or protein complex; and so forth). Exogenous donor nucleic acids can comprise one or more fluorescent labels, purification tags, epitope tags, or a combination thereof. For example, an exogenous donor nucleic acid can comprise one or more fluorescent labels (e.g., fluorescent proteins or other fluorophores or dyes), such as at least 1, at least 2, at least 3, at least 4, or at least 5 fluorescent labels. Exemplary fluorescent labels include fluorophores such as fluorescein (e.g., 6-carboxyfluorescein (6-FAM)), Texas Red, HEX, Cy3, Cy5, Cy5.5, Pacific Blue, 5-(and-6)-carboxytetramethylrhodamine (TAMRA), and Cy7. A wide range of fluorescent dyes are available commercially for labeling oligonucleotides (e.g., from Integrated DNA Technologies). Such fluorescent labels (e.g., internal fluorescent labels) can be used, for example, to detect an exogenous donor nucleic acid that has been directly integrated into a cleaved target nucleic acid having protruding ends compatible with the ends of the exogenous donor nucleic acid. The label or tag can be at the 5' end, the 3' end, or internally within the exogenous donor nucleic acid. For example, an exogenous donor nucleic acid can be conjugated at 5' end with the IR700 fluorophore from Integrated DNA Technologies (5'IRDYE® 700).

Exogenous donor nucleic acids can also comprise nucleic acid inserts including segments of DNA to be integrated at target genomic loci. Integration of a nucleic acid insert at a target genomic locus can result in addition of a nucleic acid sequence of interest to the target genomic locus, deletion of a nucleic acid sequence of interest at the target genomic locus, or replacement of a nucleic acid sequence of interest at the target genomic locus (i.e., deletion and insertion). Some exogenous donor nucleic acids are designed for insertion of a nucleic acid insert at a target genomic locus without any corresponding deletion at the target genomic locus. Other exogenous donor nucleic acids are designed to delete a nucleic acid sequence of interest at a target genomic locus without any corresponding insertion of a nucleic acid insert. Yet other exogenous donor nucleic acids are designed to delete a nucleic acid sequence of interest at a target genomic locus and replace it with a nucleic acid insert.

The nucleic acid insert or the corresponding nucleic acid at the target genomic locus being deleted and/or replaced can be various lengths. An exemplary nucleic acid insert or corresponding nucleic acid at the target genomic locus being deleted and/or replaced is between about 1 nucleotide to about 5 kb in length or is between about 1 nucleotide to about 1,000 nucleotides in length. For example, a nucleic acid insert or a corresponding nucleic acid at the target genomic locus being deleted and/or replaced can be between about 1-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, or 190-120 nucleotides in length. Likewise, a nucleic acid insert or a corresponding nucleic acid at the target genomic locus being deleted and/or replaced can be between 1-100, 100-200, 200-300, 300-400, 400-500, 500-600, 600-700, 700-800, 800-900, or 900-1000 nucleotides in length. Likewise, a nucleic acid insert or a corresponding nucleic acid at the target genomic locus being deleted and/or replaced can be between about 1-1.5, 1.5-2, 2-2.5, 2.5-3, 3-3.5, 3.5-4, 4-4.5, or 4.5-5 kb in length or longer.

The nucleic acid insert can comprise a sequence that is homologous or orthologous to all or part of sequence targeted for replacement. For example, the nucleic acid insert can comprise a sequence that comprises one or more point mutations (e.g., 1, 2, 3, 4, 5, or more) compared with a sequence targeted for replacement at the target genomic locus. Optionally, such point mutations can result in a conservative amino acid substitution (e.g., substitution of aspartic acid [Asp, D] with glutamic acid [Glu, E]) in the encoded polypeptide.

(2) Donor Nucleic Acids for Non-Homologous-End-Joining-Mediated Insertion

Some exogenous donor nucleic acids have short single-stranded regions at the 5' end and/or the 3' end that are complementary to one or more overhangs created by Cas-protein-mediated cleavage at the target genomic locus. These overhangs can also be referred to as 5' and 3' homology arms. For example, some exogenous donor nucleic acids have short single-stranded regions at the 5' end and/or the 3' end that are complementary to one or more overhangs created by Cas-protein-mediated cleavage at 5' and/or 3' target sequences at the target genomic locus. Some such exogenous donor nucleic acids have a complementary region only at the 5' end or only at the 3' end. For example, some such exogenous donor nucleic acids have a complementary region only at the 5' end complementary to an overhang created at a 5' target sequence at the target genomic locus or only at the 3' end complementary to an overhang created at a 3' target sequence at the target genomic locus. Other such exogenous donor nucleic acids have complementary regions at both the 5' and 3' ends. For example, other such exogenous donor nucleic acids have complementary regions at both the 5' and 3' ends e.g., complementary to first and second overhangs, respectively, generated by Cas-mediated cleavage at the target genomic locus. For example, if the exogenous donor nucleic acid is double-stranded, the single-stranded complementary regions can extend from the 5' end of the top strand of the donor nucleic acid and the 5' end of the bottom strand of the donor nucleic acid, creating 5' overhangs on each end. Alternatively, the single-stranded complementary region can extend from the 3' end of the top strand of the donor nucleic acid and from the 3' end of the bottom strand of the template, creating 3' overhangs.

The complementary regions can be of any length sufficient to promote ligation between the exogenous donor nucleic acid and the target nucleic acid. Exemplary complementary regions are between about 1 to about 5 nucleotides in length, between about 1 to about 25 nucleotides in length, or between about 5 to about 150 nucleotides in length. For example, a complementary region can be at least about 1, 2, 3, 4, 5, 6, 7, 8, 9, 10, 11, 12, 13, 14, 15, 16, 17, 18, 19, 20, 21, 22, 23, 24, or 25 nucleotides in length. Alternatively, the complementary region can be about 5-10, 10-20, 20-30, 30-40, 40-50, 50-60, 60-70, 70-80, 80-90, 90-100, 100-110, 110-120, 120-130, 130-140, or 140-150 nucleotides in length, or longer.

Such complementary regions can be complementary to overhangs created by two pairs of nickases. Two double-strand breaks with staggered ends can be created by using first and second nickases that cleave opposite strands of DNA to create a first double-strand break, and third and fourth nickases that cleave opposite strands of DNA to create a second double-strand break. For example, a Cas protein can be used to nick first, second, third, and fourth guide RNA target sequences corresponding with first, second, third, and fourth guide RNAs. The first and second guide RNA target sequences can be positioned to create a first cleavage site such that the nicks created by the first and second nickases on the first and second strands of DNA create a double-strand break (i.e., the first cleavage site comprises the nicks within the first and second guide RNA target sequences). Likewise, the third and fourth guide RNA target sequences can be positioned to create a second cleavage site such that the nicks created by the third and fourth nickases on the first and second strands of DNA create a double-strand break (i.e., the second cleavage site comprises the nicks within the third and fourth guide RNA target sequences). Optionally, the nicks within the first and second guide RNA target sequences and/or the third and fourth guide RNA target sequences can be off-set nicks that create overhangs. The offset window can be, for example, at least about 5 bp, 10 bp, 20 bp, 30 bp, 40 bp, 50 bp, 60 bp, 70 bp, 80 bp, 90 bp, 100 bp or more. See Ran et al. (2013) *Cell* 154:1380-1389; Mali et al. (2013) *Nat. Biotech*.31:833-838; and Shen et al. (2014) *Nat. Methods* 11:399-404, each of which is herein incorporated by reference in its entirety for all purposes. In such cases, a double-stranded exogenous donor nucleic acid can be designed with single-stranded complementary regions that are complementary to the overhangs created by the nicks within the first and second guide RNA target sequences and by the nicks within the third and fourth guide RNA target sequences. Such an exogenous donor nucleic acid can then be inserted by non-homologous-end-joining-mediated ligation.

(3) Donor Nucleic Acids for Insertion by Homology-Directed Repair

Some exogenous donor nucleic acids comprise homology arms. If the exogenous donor nucleic acid also comprises a nucleic acid insert, the homology arms can flank the nucleic acid insert. For ease of reference, the homology arms are referred to herein as 5' and 3' (i.e., upstream and downstream) homology arms. This terminology relates to the relative position of the homology arms to the nucleic acid insert within the exogenous donor nucleic acid. The 5' and 3' homology arms correspond to regions within the target genomic locus, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found in the exogenous donor nucleic acid can be any degree of sequence identity that allows for homologous recombination to occur. For example, the amount of sequence identity shared by the homology arm of the exogenous donor nucleic acid (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination. Exemplary homology arms are between about 25 nucleotides to about 2.5 kb in length, are between about 25 nucleotides to about 1.5 kb in length, or are between about 25 to about 500 nucleotides in length. For example, a given homology arm (or each of the homology arms) and/or corresponding target sequence can comprise corresponding regions of homology that are between about 25-30, 30-40, 40-50, 50-60, 60-70, 70-80, 80-90, 90-100, 100-150, 150-200, 200-250, 250-300, 300-350, 350-400, 400-450, or 450-500 nucleotides in length, such that the homology arms have sufficient homology to undergo homologous recombination with the corresponding target sequences within the target nucleic acid. Alternatively, a given homology arm (or each homology arm) and/or corresponding target sequence can comprise corresponding regions of homology that are between about 0.5 kb to about 1 kb, about 1 kb to about 1.5 kb, about 1.5 kb to about 2 kb, or about 2 kb to about 2.5 kb in length. For example, the homology arms can each be about 750 nucleotides in length. The homology arms can be symmetrical (each about the same size in length), or they can be asymmetrical (one longer than the other).

When a CRISPR/Cas system is used in combination with an exogenous donor nucleic acid, the 5' and 3' target sequences are optionally located in sufficient proximity to the Cas cleavage site (e.g., within sufficient proximity to a the guide RNA target sequence) so as to promote the occurrence of a homologous recombination event between the target sequences and the homology arms upon a single-strand break (nick) or double-strand break at the Cas cleavage site. The term "Cas cleavage site" includes a DNA sequence at which a nick or double-strand break is created by a Cas enzyme (e.g., a Cas9 protein complexed with a guide RNA). The target sequences within the targeted locus that correspond to the 5' and 3' homology arms of the exogenous donor nucleic acid are "located in sufficient proximity" to a Cas cleavage site if the distance is such as to promote the occurrence of a homologous recombination event between the 5' and 3' target sequences and the homology arms upon a single-strand break or double-strand break at the Cas cleavage site. Thus, the target sequences corresponding to the 5' and/or 3' homology arms of the exogenous donor nucleic acid can be, for example, within at least 1 nucleotide of a given Cas cleavage site or within at least 10 nucleotides to about 1,000 nucleotides of a given Cas cleavage site. As an example, the Cas cleavage site can be immediately adjacent to at least one or both of the target sequences.

The spatial relationship of the target sequences that correspond to the homology arms of the exogenous donor nucleic acid and the Cas cleavage site can vary. For example, target sequences can be located 5' to the Cas cleavage site, target sequences can be located 3' to the Cas cleavage site, or the target sequences can flank the Cas cleavage site.

D. Methods of Optimizing Ability of CRISPR/Cas to Induce Recombination of a Target Genomic Nucleic Acid with an Exogenous Donor Nucleic Acid In Vivo or Ex Vivo Various methods are provided for optimizing delivery of CRISPR/Cas to a cell or non-human animal or optimizing CRISPR/Cas-induced recombination activity in vivo or ex vivo. Such methods can comprise, for example: (a) performing the method of testing CRISPR/Cas-induced recombination of a target genomic locus with an exogenous donor nucleic acid as described elsewhere herein a first time in a first non-human animal; (b) changing a variable and performing the method a second time with the changed variable in a second non-human animal (i.e., of the same species); and (c) comparing the activity or expression of the reporter protein in step (a) with the activity or expression of the reporter protein in step (b), and selecting the method resulting in the higher activity or expression the reporter protein (i.e., selecting the method resulting in higher efficacy).

Alternatively, the method selected in step (c) can be the method resulting in targeted modification of the CRISPR reporter or increased activity or expression of the reporter protein with higher efficacy, higher precision, higher consistency, or higher specificity. Higher efficacy refers to higher levels of modification of the target locus in the CRISPR reporter (e.g., a higher percentage of cells is targeted within a particular target cell type, within a particular target tissue, or within a particular target organ). Higher precision refers to more precise modification of the target locus in the CRISPR reporter (e.g., a higher percentage of targeted cells having the same modification or having the desired modification without extra unintended insertions and deletions (e.g., NHEJ indels)). Higher consistency refers to more consistent modification of the target locus in the CRISPR reporter among different types of targeted cells, tissues, or organs if more than one type of cell, tissue, or organ is being targeted (e.g., modification of a greater number of cell types within a target organ). If a particular organ is being targeted, higher consistency can also refer to more consistent modification throughout all locations within the organ. Higher specificity can refer to higher specificity with respect to the locus targeted within the CRISPR reporter, higher specificity with respect to the cell type targeted, higher specificity with respect to the tissue type targeted, or higher specificity with respect to the organ targeted. For example, increased locus specificity refers to less modification of off-target genomic loci (e.g., a lower percentage of targeted cells having modifications at unintended, off-target genomic loci instead of or in addition to modification of the target locus in the CRISPR reporter). Likewise, increased cell type, tissue, or organ type specificity refers to less modification of off-target cell types, tissue types, or organ types if a particular cell type, tissue type, or organ type is being targeted (e.g., when a particular organ is targeted (e.g., the liver), there is less modification of cells in organs or tissues that are not intended targets).

The variable that is changed can be any parameter. As one example, the changed variable can be the packaging or the delivery method by which one or more or all of the guide RNA, the exogenous donor nucleic acid, and the Cas protein are introduced into the cell or non-human animal. Examples of delivery methods, such as LNP, HDD, and AAV, are disclosed elsewhere herein. As another example, the changed variable can be the route of administration for introduction of one or more or all of the guide RNA, the exogenous donor nucleic acid, and the Cas protein into the non-human animal. Examples of routes of administration, such as intravenous, intravitreal, intraparenchymal, and nasal instillation, are disclosed elsewhere herein.

As another example, the changed variable can be the concentration or amount of one or more or all of the guide RNA introduced, the Cas protein introduced, and the exogenous donor nucleic acid introduced. As another example, the changed variable can be the concentration or the amount of guide RNA introduced relative to the concentration or the amount of Cas protein introduced, the concentration or the amount of guide RNA introduced relative to the concentration or the amount of exogenous donor nucleic acid introduced, or the concentration or the amount of exogenous donor nucleic acid introduced relative to the concentration or the amount of Cas protein introduced.

As another example, the changed variable can be the timing of introducing one or more or all of the guide RNA, exogenous donor nucleic acid, and the Cas protein relative to the timing of measuring expression or activity of the one or more reporter proteins. As another example, the changed variable can be the number of times or frequency with which one or more or all of the guide RNA, exogenous donor nucleic acid, and the Cas protein are introduced. As another example, the changed variable can be the timing of introduction of guide RNA relative to the timing of introduction of Cas protein, the timing of introduction of guide RNA relative to the timing of introduction of exogenous donor nucleic acid, or the timing of introduction of exogenous donor nucleic acid relative to the timing of introduction of Cas protein.

As another example, the changed variable can be the form in which one or more or all of the guide RNA, the exogenous donor nucleic acid, and the Cas protein are introduced. For example, the guide RNA can be introduced in the form of DNA or in the form of RNA. The Cas protein can be introduced in the form of DNA, RNA, or protein. The exogenous donor nucleic acid can be DNA, RNA, single-stranded, double-stranded, linear, circular, and so forth. Similarly, each of the components can comprise various combinations of modifications for stability, to reduce off-target effects, to facilitate delivery, and so forth. As another example, the changed variable can be one or more or all of the guide RNA that is introduced (e.g., introducing a different guide RNA with a different sequence), the exogenous donor nucleic acid that is introduced (e.g., introducing a different exogenous donor nucleic acid with a different sequence), and the Cas protein that is introduced (e.g., introducing a different Cas protein with a different sequence, or a nucleic acid with a different sequence but encoding the same Cas protein amino acid sequence).

E. Introducing Guide RNAs and Cas Proteins into Cells and Non-Human Animals

The methods disclosed herein comprise introducing into a cell or non-human animal one or more or all of guide RNAs, exogenous donor nucleic acids, and Cas proteins. "Introducing" includes presenting to the cell or non-human animal the nucleic acid or protein in such a manner that the nucleic acid or protein gains access to the interior of the cell or to the interior of cells within the non-human animal. The introducing can be accomplished by any means, and two or more of the components (e.g., two of the components, or all of the components) can be introduced into the cell or non-human animal simultaneously or sequentially in any combination. For example, a Cas protein can be introduced into a cell or non-human animal before introduction of a guide RNA, or it can be introduced following introduction of the guide RNA. As another example, an exogenous donor nucleic acid can be introduced prior to the introduction of a Cas protein and a guide RNA, or it can be introduced following introduction of the Cas protein and the guide RNA (e.g., the exogenous donor nucleic acid can be administered about 1, 2, 3, 4, 8, 12, 24, 36, 48, or 72 hours before or after introduction of the Cas protein and the guide RNA). See, e.g., US 2015/0240263 and US 2015/0110762, each of which is herein incorporated by reference in its entirety for all purposes. In addition, two or more of the components can be introduced into the cell or non-human animal by the same delivery method or different delivery methods. Similarly, two or more of the components can be introduced into a non-human animal by the same route of administration or different routes of administration.

A guide RNA can be introduced into the cell in the form of an RNA (e.g., in vitro transcribed RNA) or in the form of a DNA encoding the guide RNA. When introduced in the form of a DNA, the DNA encoding a guide RNA can be operably linked to a promoter active in the cell. For example, a guide RNA may be delivered via AAV and expressed in vivo under a U6 promoter. Such DNAs can be in one or more expression constructs. For example, such expression constructs can be components of a single nucleic acid molecule. Alternatively, they can be separated in any combination among two or more nucleic acid molecules (i.e., DNAs encoding one or more CRISPR RNAs and DNAs encoding one or more tracrRNAs can be components of a separate nucleic acid molecules).

Likewise, Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a bacterial cell, a yeast cell, a human cell, a non-human cell, a mammalian cell, a rodent cell, a mouse cell, a rat cell, or any other host cell of interest, as compared to the naturally occurring polynucleotide sequence. When a nucleic acid encoding the Cas protein is introduced into the cell, the Cas protein can be transiently, conditionally, or constitutively expressed in the cell.

Nucleic acids encoding Cas proteins or guide RNAs can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a vector comprising a DNA encoding one or more gRNAs. Alternatively, it can be in a vector or plasmid that is separate from the vector comprising the DNA encoding one or more gRNAs. Suitable promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allows for the generation of compact expression cassettes to facilitate delivery.

Exogenous donor nucleic acids, guide RNAs, and Cas proteins (or nucleic acids encoding guide RNAs or Cas proteins) can be provided in compositions comprising a carrier increasing the stability of the exogenous donor nucleic acid, guide RNA, or Cas protein (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly (lactic acid) (PLA) microspheres, poly(D,L-lactic-coglycolic-acid) (PLGA) microspheres, liposomes, micelles, inverse micelles, lipid cochleates, and lipid microtubules.

Various methods and compositions are provided herein to allow for introduction of a nucleic acid or protein into a cell or non-human animal. Methods for introducing nucleic acids into various cell types are known in the art and include, for example, stable transfection methods, transient transfection methods, and virus-mediated methods.

Transfection protocols as well as protocols for introducing nucleic acid sequences into cells may vary. Non-limiting transfection methods include chemical-based transfection methods using liposomes; nanoparticles; calcium phosphate (Graham et al. (1973) *Virology* 52 (2): 456-67, Bacchetti et al. (1977) *Proc. Natl. Acad. Sci. USA* 74 (4): 1590-4, and Kriegler, M (1991). Transfer and Expression: A Laboratory Manual. New York: W. H. Freeman and Company. pp. 96-97); dendrimers; or cationic polymers such as DEAE-dextran or polyethylenimine. Non-chemical methods include electroporation, Sono-poration, and optical transfection. Particle-based transfection includes the use of a gene gun, or magnet-assisted transfection (Bertram (2006) *Current Pharmaceutical Biotechnology* 7, 277-28). Viral methods can also be used for transfection.

Introduction of nucleic acids or proteins into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEOFECTOR™ system.

Introduction of nucleic acids or proteins into a cell (e.g., a zygote) can also be accomplished by microinjection. In zygotes (i.e., one-cell stage embryos), microinjection can be into the maternal and/or paternal pronucleus or into the cytoplasm. If the microinjection is into only one pronucleus, the paternal pronucleus is preferable due to its larger size. Microinjection of an mRNA is preferably into the cytoplasm (e.g., to deliver mRNA directly to the translation machinery), while microinjection of a Cas protein or a polynucleotide encoding a Cas protein or encoding an RNA is preferable into the nucleus/pronucleus. Alternatively, microinjection can be carried out by injection into both the nucleus/pronucleus and the cytoplasm: a needle can first be introduced into the nucleus/pronucleus and a first amount can be injected, and while removing the needle from the one-cell stage embryo a second amount can be injected into the cytoplasm. If a Cas protein is injected into the cytoplasm, the Cas protein optionally comprises a nuclear localization signal to ensure delivery to the nucleus/pronucleus. Methods for carrying out microinjection are well known. See, e.g., Nagy et al. (Nagy A, Gertsenstein M, Vintersten K, Behringer R., 2003, Manipulating the Mouse Embryo. Cold Spring Harbor, New York: Cold Spring Harbor Laboratory Press); see also Meyer et al. (2010) *Proc. Natl. Acad. Sci. USA* 107:15022-15026 and Meyer et al. (2012) *Proc. Natl. Acad. Sci. USA* 109:9354-9359.

Other methods for introducing nucleic acid or proteins into a cell or non-human animal can include, for example, vector delivery, particle-mediated delivery, exosome-mediated delivery, lipid-nanoparticle-mediated delivery, cell-penetrating-peptide-mediated delivery, or implantable-device-mediated delivery. As specific examples, a nucleic acid or protein can be introduced into a cell or non-human animal in a carrier such as a poly(lactic acid) (PLA) microsphere, a poly(D,L-lactic-coglycolic-acid) (PLGA) microsphere, a liposome, a micelle, an inverse micelle, a lipid cochleate, or a lipid microtubule. Some specific examples of delivery to a non-human animal include hydrodynamic delivery, virus-mediated delivery (e.g., adeno-associated virus (AAV)-mediated delivery), and lipid-nanoparticle-mediated delivery.

Introduction of nucleic acids and proteins into cells or non-human animals can be accomplished by hydrodynamic delivery (HDD). Hydrodynamic delivery has emerged as a method for intracellular DNA delivery in vivo. For gene delivery to parenchymal cells, only essential DNA sequences need to be injected via a selected blood vessel, eliminating safety concerns associated with current viral and synthetic vectors. When injected into the bloodstream, DNA is capable of reaching cells in the different tissues accessible to the blood. Hydrodynamic delivery employs the force generated by the rapid injection of a large volume of solution into the incompressible blood in the circulation to overcome the physical barriers of endothelium and cell membranes that prevent large and membrane-impermeable compounds from entering parenchymal cells. In addition to the delivery of DNA, this method is useful for the efficient intracellular delivery of RNA, proteins, and other small compounds in vivo. See, e.g., Bonamassa et al. (2011) *Pharm. Res.* 28(4): 694-701, herein incorporated by reference in its entirety for all purposes.

Introduction of nucleic acids can also be accomplished by virus-mediated delivery, such as AAV-mediated delivery or lentivirus-mediated delivery. Other exemplary viruses/viral vectors include retroviruses, adenoviruses, vaccinia viruses, poxviruses, and herpes simplex viruses. The viruses can infect dividing cells, non-dividing cells, or both dividing and non-dividing cells. Such viruses can also be engineered to have reduced immunity. The viruses can be replication-competent or can be replication-defective (e.g., defective in one or more genes necessary for additional rounds of virion replication and/or packaging). Viruses can cause transient expression, long-lasting expression (e.g., at least 1 week, 2 weeks, 1 month, 2 months, or 3 months), or permanent expression (e.g., of Cas9 and/or gRNA). Exemplary viral titers (e.g., AAV titers) include $10^{12}$, $10^{13}$, $10^{14}$, $10^{15}$, and $10^{16}$ vector genomes/mL.

The ssDNA AAV genome consists of two open reading frames, Rep and Cap, flanked by two inverted terminal repeats that allow for synthesis of the complementary DNA strand. When constructing an AAV transfer plasmid, the transgene is placed between the two ITRs, and Rep and Cap can be supplied in trans. In addition to Rep and Cap, AAV can require a helper plasmid containing genes from adenovirus. These genes (E4, E2a, and VA) mediated AAV replication. For example, the transfer plasmid, Rep/Cap, and the helper plasmid can be transfected into HEK293 cells containing the adenovirus gene E1+ to produce infectious AAV particles. Alternatively, the Rep, Cap, and adenovirus helper genes may be combined into a single plasmid. Similar packaging cells and methods can be used for other viruses, such as retroviruses.

Multiple serotypes of AAV have been identified. These serotypes differ in the types of cells they infect (i.e., their tropism), allowing preferential transduction of specific cell types. Serotypes for CNS tissue include AAV1, AAV2, AAV4, AAV5, AAV8, and AAV9. Serotypes for heart tissue include AAV1, AAV8, and AAV9. Serotypes for kidney tissue include AAV2. Serotypes for lung tissue include AAV4, AAV5, AAV6, and AAV9. Serotypes for pancreas tissue include AAV8. Serotypes for photoreceptor cells include AAV2, AAV5, and AAV8. Serotypes for retinal pigment epithelium tissue include AAV1, AAV2, AAV4, AAV5, and AAV8. Serotypes for skeletal muscle tissue include AAV1, AAV6, AAV7, AAV8, and AAV9. Serotypes for liver tissue include AAV7, AAV8, and AAV9, and particularly AAV8.

Tropism can be further refined through pseudotyping, which is the mixing of a capsid and a genome from different viral serotypes. For example AAV2/5 indicates a virus containing the genome of serotype 2 packaged in the capsid from serotype 5. Use of pseudotyped viruses can improve transduction efficiency, as well as alter tropism. Hybrid capsids derived from different serotypes can also be used to alter viral tropism. For example, AAV-DJ contains a hybrid capsid from eight serotypes and displays high infectivity across a broad range of cell types in vivo. AAV-DJ8 is another example that displays the properties of AAV-DJ but with enhanced brain uptake. AAV serotypes can also be modified through mutations. Examples of mutational modifications of AAV2 include Y444F, Y500F, Y730F, and S662V. Examples of mutational modifications of AAV3 include Y705F, Y731F, and T492V. Examples of mutational modifications of AAV6 include S663V and T492V. Other pseudotyped/modified AAV variants include AAV2/1, AAV2/6, AAV2/7, AAV2/8, AAV2/9, AAV2.5, AAV8.2, and AAV/SASTG.

To accelerate transgene expression, self-complementary AAV (scAAV) variants can be used. Because AAV depends on the cell's DNA replication machinery to synthesize the complementary strand of the AAV's single-stranded DNA genome, transgene expression may be delayed. To address this delay, scAAV containing complementary sequences that are capable of spontaneously annealing upon infection can be used, eliminating the requirement for host cell DNA synthesis. However, single-stranded AAV (ssAAV) vectors can also be used.

To increase packaging capacity, longer transgenes may be split between two AAV transfer plasmids, the first with a 3' splice donor and the second with a 5' splice acceptor. Upon co-infection of a cell, these viruses form concatemers, are spliced together, and the full-length transgene can be expressed. Although this allows for longer transgene expression, expression is less efficient. Similar methods for increasing capacity utilize homologous recombination. For example, a transgene can be divided between two transfer plasmids but with substantial sequence overlap such that co-expression induces homologous recombination and expression of the full-length transgene.

Introduction of nucleic acids and proteins can also be accomplished by lipid nanoparticle (LNP)-mediated delivery. For example, LNP-mediated delivery can be used to deliver a combination of Cas mRNA and guide RNA or a combination of Cas protein and guide RNA. Delivery through such methods results in transient Cas expression, and the biodegradable lipids improve clearance, improve tolerability, and decrease immunogenicity. Lipid formulations can protect biological molecules from degradation while improving their cellular uptake. Lipid nanoparticles are particles comprising a plurality of lipid molecules physically associated with each other by intermolecular forces. These include microspheres (including unilamellar and multilamellar vesicles, e.g., liposomes), a dispersed phase in an emulsion, micelles, or an internal phase in a suspension. Such lipid nanoparticles can be used to encapsulate one or more nucleic acids or proteins for delivery. Formulations which contain cationic lipids are useful for delivering polyanions such as nucleic acids. Other lipids that can be included are neutral lipids (i.e., uncharged or zwitterionic lipids), anionic lipids, helper lipids that enhance transfection, and stealth lipids that increase the length of time for which nanoparticles can exist in vivo. Examples of suitable cationic lipids, neutral lipids, anionic lipids, helper lipids, and stealth lipids can be found in WO 2016/010840 A1, herein incorporated by reference in its entirety for all purposes. An exemplary lipid nanoparticle can comprise a cationic lipid and one or more other components. In one example, the other component can comprise a helper lipid such as cholesterol. In another example, the other components can comprise a helper lipid such as cholesterol and a neutral lipid such as DSPC. In another example, the other components can comprise a helper lipid such as cholesterol, an optional neutral lipid such as DSPC, and a stealth lipid such as S010, S024, S027, S031, or S033.

The LNP may contain one or more all of the following: (i) a lipid for encapsulation and for endosomal escape; (ii) a neutral lipid for stabilization; (iii) a helper lipid for stabilization; and (iv) a stealth lipid. See, e.g., Finn et al. (2018) Cell Reports 22:1-9 and WO 2017/173054 A1, each of which is herein incorporated by reference in its entirety for all purposes. In certain LNPs, the cargo can include a guide RNA or a nucleic acid encoding a guide RNA. In certain LNPs, the cargo can include an exogenous donor nucleic acid. In certain LNPs, the cargo can include a guide RNA or a nucleic acid encoding a guide RNA and a Cas protein or a nucleic acid encoding a Cas protein. In certain LNPs, the cargo can include a guide RNA or a nucleic acid encoding a guide RNA, a Cas protein or a nucleic acid encoding a Cas protein, and an exogenous donor nucleic acid.

The lipid for encapsulation and endosomal escape can be a cationic lipid. The lipid can also be a biodegradable lipid, such as a biodegradable ionizable lipid. One example of a suitable lipid is Lipid A or LP01, which is (9Z,12Z)-3-((4, 4-bis(octyloxy)butanoyl)oxy)-2-((((3-(diethylamino) propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z, 12Z)-octadeca-9,12-dienoate. See, e.g., Finn et al. (2018) Cell Reports 22:1-9 and WO 2017/173054 A1, each of which is herein incorporated by reference in its entirety for all purposes. Another example of a suitable lipid is Lipid B, which is ((5-((dimethylamino)methyl)-1,3-phenylene)bis (oxy))bis(octane-8,1-diyl)bis(decanoate), also called ((5-((dimethylamino)methyl)-1,3-phenylene)bis(oxy))bis(octane-8,1-diyl)bis(decanoate). Another example of a suitable lipid is Lipid C, which is 2-((4-(((3-(dimethylamino) propoxy)carbonyl)oxy)hexadecanoyl)oxy)propane-1,3-diyl (9Z,9'Z,12Z,12Z)-bis(octadeca-9,12-dienoate). Another example of a suitable lipid is Lipid D, which is 3-(((3-(dimethylamino)propoxy)carbonyl)oxy)-13-(octanoyloxy) tridecyl 3-octylundecanoate. Other suitable lipids include heptatriaconta-6,9,28,31-tetraen-19-yl4-(dimethylamino) butanoate (also known as Dlin-MC3-DMA (MC3))).

Some such lipids suitable for use in the LNPs described herein are biodegradable in vivo. For example, LNPs comprising such a lipid include those where at least 75% of the lipid is cleared from the plasma within 8, 10, 12, 24, or 48 hours, or 3, 4, 5, 6, 7, or 10 days. As another example, at least 50% of the LNP is cleared from the plasma within 8, 10, 12, 24, or 48 hours, or 3, 4, 5, 6, 7, or 10 days.

Such lipids may be ionizable depending upon the pH of the medium they are in. For example, in a slightly acidic medium, the lipids may be protonated and thus bear a positive charge. Conversely, in a slightly basic medium, such as, for example, blood where pH is approximately 7.35, the lipids may not be protonated and thus bear no charge. In some embodiments, the lipids may be protonated at a pH of at least about 9, 9.5, or 10. The ability of such a lipid to bear a charge is related to its intrinsic pKa. For example, the lipid may, independently, have a pKa in the range of from about 5.8 to about 6.2.

Neutral lipids function to stabilize and improve processing of the LNPs. Examples of suitable neutral lipids include a variety of neutral, uncharged or zwitterionic lipids. Examples of neutral phospholipids suitable for use in the present disclosure include, but are not limited to, 5-heptadecylbenzene-1,3-diol (resorcinol), dipalmitoylphosphatidylcholine (DPPC), distearoylphosphatidylcholine (DSPC), phosphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1,2-diarachidoyl-sn-glycero-3-pho sphocholine (DBPC), 1-stearoyl-2-palmitoyl phosphatidylcholine (SPPC), 1,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine distearoylphosphatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine, and combinations thereof. For example, the neutral phospholipid may be selected from the group consisting of distearoylphosphatidylcholine (DSPC) and dimyristoyl phosphatidyl ethanolamine (DMPE).

Helper lipids include lipids that enhance transfection. The mechanism by which the helper lipid enhances transfection can include enhancing particle stability. In certain cases, the helper lipid can enhance membrane fusogenicity. Helper lipids include steroids, sterols, and alkyl resorcinols. Examples of suitable helper lipids suitable include cholesterol, 5-heptadecylresorcinol, and cholesterol hemisuccinate. In one example, the helper lipid may be cholesterol or cholesterol hemisuccinate.

Stealth lipids include lipids that alter the length of time the nanoparticles can exist in vivo. Stealth lipids may assist in the formulation process by, for example, reducing particle aggregation and controlling particle size. Stealth lipids may modulate pharmacokinetic properties of the LNP. Suitable stealth lipids include lipids having a hydrophilic head group linked to a lipid moiety.

The hydrophilic head group of stealth lipid can comprise, for example, a polymer moiety selected from polymers based on PEG (sometimes referred to as poly(ethylene oxide)), poly(oxazoline), poly(vinyl alcohol), poly(glycerol), poly(N-vinylpyrrolidone), polyaminoacids, and poly N-(2-hydroxypropyl)methacrylamide. The term PEG means any polyethylene glycol or other polyalkylene ether polymer. In certain LNP formulations, the PEG, is a PEG-2K, also termed PEG 2000, which has an average molecular weight of about 2,000 daltons. See, e.g., WO 2017/173054 A1, herein incorporated by reference in its entirety for all purposes.

The lipid moiety of the stealth lipid may be derived, for example, from diacylglycerol or diacylglycamide, including those comprising a dialkylglycerol or dialkylglycamide group having alkyl chain length independently comprising from about C4 to about C40 saturated or unsaturated carbon atoms, wherein the chain may comprise one or more functional groups such as, for example, an amide or ester. The dialkylglycerol or dialkylglycamide group can further comprise one or more substituted alkyl groups.

As one example, the stealth lipid may be selected from PEG-dilauroylglycerol, PEG-dimyristoylglycerol (PEG-DMG), PEG-dipalmitoylglycerol, PEG-distearoylglycerol (PEG-DSPE), PEG-dilaurylglycamide, PEG-dimyristylglycamide, PEG-dipalmitoylglycamide, and PEG-distearoylglycamide, PEG-cholesterol (1-[8'-(Cholest-5-en-3 [beta]-oxy)carboxamido-3',6'-dioxaoctanyl]carbamoyl-[omega]-methyl-poly(ethylene glycol), PEG-DMB (3,4-ditetradecoxylbenzyl-[omega]-methyl-poly(ethylene glycol)ether), 1,2-dimyristoyl-sn-glycero-3-phosphoethanolamine-N-[methoxy(polyethylene glycol)-2000] (PEG2k-DMG), 1,2-distearoyl-sn-glycero-3-phosphoethanolamine-N-[methoxy(polyethylene glycol)-2000] (PEG2k-DSPE), 1,2-distearoyl-sn-glycerol, methoxypoly ethylene glycol (PEG2k-DSG), poly(ethylene glycol)-2000-dimethacrylate (PEG2k-DMA), and 1,2-distearyloxypropyl-3-amine-N-[methoxy(polyethylene glycol)-2000] (PEG2k-DSA). In one particular example, the stealth lipid may be PEG2k-DMG.

The LNPs can comprise different respective molar ratios of the component lipids in the formulation. The mol-% of the CCD lipid may be, for example, from about 30 mol-% to about 60 mol-%, from about 35 mol-% to about 55 mol-%, from about 40 mol-% to about 50 mol-%, from about 42 mol-% to about 47 mol-%, or about 45%. The mol-% of the helper lipid may be, for example, from about 30 mol-% to about 60 mol-%, from about 35 mol-% to about 55 mol-%, from about 40 mol-% to about 50 mol-%, from about 41 mol-% to about 46 mol-%, or about 44 mol-%. The mol-% of the neutral lipid may be, for example, from about 1 mol-% to about 20 mol-%, from about 5 mol-% to about 15 mol-%, from about 7 mol-% to about 12 mol-%, or about 9 mol-%. The mol-% of the stealth lipid may be, for example, from about 1 mol-% to about 10 mol-%, from about 1 mol-% to about 5 mol-%, from about 1 mol-% to about 3 mol-%, about 2 mol-%, or about 1 mol-%.

The LNPs can have different ratios between the positively charged amine groups of the biodegradable lipid (N) and the negatively charged phosphate groups (P) of the nucleic acid to be encapsulated. This may be mathematically represented by the equation N/P. For example, the N/P ratio may be from about 0.5 to about 100, from about 1 to about 50, from about 1 to about 25, from about 1 to about 10, from about 1 to about 7, from about 3 to about 5, from about 4 to about 5, about 4, about 4.5, or about 5.

In some LNPs, the cargo can comprise Cas mRNA and gRNA. The Cas mRNA and gRNAs can be in different ratios. For example, the LNP formulation can include a ratio of Cas mRNA to gRNA nucleic acid ranging from about 25:1 to about 1:25, ranging from about 10:1 to about 1:10, ranging from about 5:1 to about 1:5, or about 1:1. Alternatively, the LNP formulation can include a ratio of Cas mRNA to gRNA nucleic acid from about 1:1 to about 1:5, or about 10:1. Alternatively, the LNP formulation can include a ratio of Cas mRNA to gRNA nucleic acid of about 1:10, 25:1, 10:1, 5:1, 3:1, 1:1, 1:3, 1:5, 1:10, or 1:25.

In some LNPs, the cargo can comprise exogenous donor nucleic acid and gRNA. The exogenous donor nucleic acid and gRNAs can be in different ratios. For example, the LNP formulation can include a ratio of exogenous donor nucleic acid to gRNA nucleic acid ranging from about 25:1 to about 1:25, ranging from about 10:1 to about 1:10, ranging from about 5:1 to about 1:5, or about 1:1. Alternatively, the LNP formulation can include a ratio of exogenous donor nucleic acid to gRNA nucleic acid from about 1:1 to about 1:5, about 5:1 to about 1:1, about 10:1, or about 1:10. Alternatively, the LNP formulation can include a ratio of exogenous donor nucleic acid to gRNA nucleic acid of about 1:10, 25:1, 10:1, 5:1, 3:1, 1:1, 1:3, 1:5, 1:10, or 1:25.

A specific example of a suitable LNP has a nitrogen-to-phosphate (N/P) ratio of 4.5 and contains biodegradable cationic lipid, cholesterol, DSPC, and PEG2k-DMG in a 45:44:9:2 molar ratio. The biodegradable cationic lipid can be (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl) propyl (9Z,12Z)-octadeca-9,12-dienoate. See, e.g., Finn et al. (2018) *Cell Reports* 22:1-9, herein incorporated by reference in its entirety for all purposes. Another specific example of a suitable LNP contains Dlin-MC3-DMA (MC3), cholesterol, DSPC, and PEG-DMG in a 50:38.5:10:1.5 molar ratio.

The mode of delivery can be selected to decrease immunogenicity. For example, a Cas protein and a gRNA may be delivered by different modes (e.g., bi-modal delivery). These different modes may confer different pharmacodynamics or pharmacokinetic properties on the subject delivered molecule (e.g., Cas or nucleic acid encoding, gRNA or nucleic acid encoding, or exogenous donor nucleic acid/repair template). For example, the different modes can result in different tissue distribution, different half-life, or different temporal distribution. Some modes of delivery result in more persistent expression and presence of the molecule, whereas other modes of delivery are transient and less persistent (e.g., delivery of an RNA or a protein). Delivery of Cas proteins in a more transient manner, for example as mRNA or protein, can ensure that the Cas/gRNA complex is only present and active for a short period of time and can reduce immunogenicity caused by peptides from the bacterially-derived Cas enzyme being displayed on the surface of the cell by MHC molecules. Such transient delivery can also reduce the possibility of off-target modifications.

Administration in vivo can be by any suitable route including, for example, parenteral, intravenous, oral, subcutaneous, intra-arterial, intracranial, intrathecal, intraperitoneal, topical, intranasal, or intramuscular. Systemic modes of administration include, for example, oral and parenteral routes. Examples of parenteral routes include intravenous, intraarterial, intraosseous, intramuscular, intradermal, subcutaneous, intranasal, and intraperitoneal routes. A specific example is intravenous infusion. Nasal instillation and intravitreal injection are other specific examples. Local modes of administration include, for example, intrathecal, intracerebroventricular, intraparenchymal (e.g., localized intraparenchymal delivery to the striatum (e.g., into the caudate or into the putamen), cerebral cortex, precentral gyrus, hippocampus (e.g., into the dentate gyrus or CA3 region), temporal cortex, amygdala, frontal cortex, thalamus, cerebellum, medulla, hypothalamus, tectum, tegmentum, or substantia nigra), intraocular, intraorbital, subconjuctival, intravitreal, subretinal, and transscleral routes. Significantly smaller amounts of the components (compared with systemic approaches) may exert an effect when administered locally (for example, intraparenchymal or intravitreal) compared to when administered systemically (for example, intravenously). Local modes of administration may also reduce or eliminate the incidence of potentially toxic side effects that may occur when therapeutically effective amounts of a component are administered systemically.

Administration in vivo can be by any suitable route including, for example, parenteral, intravenous, oral, subcutaneous, intra-arterial, intracranial, intrathecal, intraperitoneal, topical, intranasal, or intramuscular. A specific example is intravenous infusion. Compositions comprising the guide RNAs and/or Cas proteins (or nucleic acids encoding the guide RNAs and/or Cas proteins) can be formulated using one or more physiologically and pharmaceutically acceptable carriers, diluents, excipients or auxiliaries. The formulation can depend on the route of administration chosen. The term "pharmaceutically acceptable" means that the carrier, diluent, excipient, or auxiliary is compatible with the other ingredients of the formulation and not substantially deleterious to the recipient thereof.

The frequency of administration and the number of dosages can be depend on the half-life of the exogenous donor nucleic acids, guide RNAs, or Cas proteins (or nucleic acids encoding the guide RNAs or Cas proteins) and the route of administration among other factors. The introduction of nucleic acids or proteins into the cell or non-human animal can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

F. Measuring CRISPR/Cas Activity In Vivo

The methods disclosed herein can further comprise detecting or measuring expression or activity of one or more reporter proteins encoded by the CRISPR reporter. The methods for detecting or measuring expression or activity will depend on the reporter protein.

For example, for fluorescent reporter proteins, the detecting or measuring can comprise spectrophotometry or flow cytometry assays or fluorescence microscopy of cells isolated from the non-human animal or macro-photography assays or in vivo imaging of the non-human animal itself.

For luciferase reporter proteins, the assay can comprise a luciferase reporter assay comprising breaking open cells isolated from the non-human animal to release all the proteins (including the luciferase), adding luciferin (for firefly luciferase) or coelenterazine (for Renilla luciferase) and all the necessary cofactors, and measuring the enzymatic activity using a luminometer. Luciferin is converted to oxyluciferin by the luciferase enzyme. Some of the energy released by this reaction is in the form of light. Alternatively, bioluminescence imaging of the non-human animal can be performed following injection of the luciferase substrate (e.g., luciferin or coelenterazine) into the non-human animal. Such assays enable noninvasive optical imaging of living animals with high sensitivity.

For beta-galactosidase reporter proteins, the assay can comprise histochemical staining of cells or tissues isolated from the non-human animal. Beta-galactosidase catalyzes the hydrolysis of X-Gal producing a blue precipitate that can be easily visualized under a microscope, thereby providing a simple and convenient method for the visual detection of LacZ expression within cells or tissues.

Other reporter proteins and assays for detecting or measuring expression or activity of such reporter proteins are well known.

Alternatively, the methods disclosed herein can further comprise identifying a cell having a modified CRISPR reporter in which the polyadenylation signal or transcription terminator sequence has been excised or identifying a cell having a modified CRISPR reporter in which the coding sequence for one reporter protein has been altered and converted into the coding sequence for a different reporter protein. Various methods can be used to identify cells having a targeted genetic modification. The screening can comprise a quantitative assay for assessing modification of allele (MOA) of a parental chromosome. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence. Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, herein incorporated by reference in its entirety for all purposes).

Next-generation sequencing (NGS) can also be used for screening. Next-generation sequencing can also be referred to as "NGS" or "massively parallel sequencing" or "high throughput sequencing." NGS can be used as a screening tool in addition to the MOA assays to define the exact nature of the targeted genetic modification and whether it is consistent across cell types or tissue types or organ types.

Assessing modification of the target genomic locus in a non-human animal can be in any cell type from any tissue or organ. For example, detecting or measuring expression or activity of one or more reporter proteins encoded by the CRISPR reporter can be assessed in multiple cell types from the same tissue or organ or in cells from multiple locations within the tissue or organ. This can provide information about which cell types within a target tissue or organ are being modified or which sections of a tissue or organ are being reached by the CRISPR/Cas and modified. As another example, detecting or measuring expression or activity of one or more reporter proteins encoded by the CRISPR reporter can be assessed in multiple types of tissue or in multiple organs. In methods in which a particular tissue or organ is being targeted, this can provide information about how effectively that tissue or organ is being targeted and whether there are off-target effects in other tissues or organs.

As one example, the CRISPR reporters disclosed herein can be a CRISPR reporter comprising both a lacZ gene and a gene encoding a fluorescent reporter protein and can be used to detect both NHEJ and homology-directed repair (HDR). For example, primary hepatocytes can be harvested from non-human animals comprising the CRISPR reporters to evaluate strategies to induce NHEJ and HDR in this cell type. Cas9 can be introduced, for example, as either an AAV, mRNA, or protein, and the gRNA can be introduced as either single guide RNA (modified and unmodified) or modular (duplex) RNA. DNA repair templates can be introduced as symmetric or asymmetric single-strand, symmetric or asymmetric double strand, or AAV vector. As a specific example, lacZ staining can be completed to assess the success of NHEJ, and fluorescent microscopy and FACs analysis can then be used to evaluate HDR efficiencies. Information gathered ex vivo can then applied to the adult non-human animal (e.g., mouse). Cas9, guide RNA, and repair template may be introduced in any of the states listed above.

IV. Methods of Making Non-Human Animals Comprising a CRISPR Reporter

Various methods are provided for making a non-human animal comprising a CRISPR reporter as disclosed elsewhere herein. Any convenient method or protocol for producing a genetically modified organism is suitable for producing such a genetically modified non-human animal. See, e.g., Cho et al. (2009) *Current Protocols in Cell Biology* 42:19.11:19.11.1-19.11.22 and Gama Sosa et al. (2010) *Brain Struct. Funct.* 214(2-3):91-109, each of which is herein incorporated by reference in its entirety for all purposes. Such genetically modified non-human animals can be generated, for example, through gene knock-in at a targeted locus (e.g., a safe harbor locus such as Rosa26) or through use of a randomly integrating transgene. See, e.g., WO 2014/093622 and WO 2013/176772, each of which is herein incorporated by reference in its entirety for all purposes. Methods of targeting a construct to the Rosa26 locus are described, for example, in US 2012/0017290, US 2011/0265198, and US 2013/0236946, each of which is herein incorporated by reference in its entirety for all purposes.

For example, the method of producing a non-human animal comprising a CRISPR reporter as disclosed elsewhere herein can comprise: (1) modifying the genome of a pluripotent cell to comprise a CRISPR reporter; (2) identifying or selecting the genetically modified pluripotent cell comprising the CRISPR reporter; (3) introducing the genetically modified pluripotent cell into a non-human animal host embryo; and (4) implanting and gestating the host embryo in a surrogate mother. Optionally, the host embryo comprising modified pluripotent cell (e.g., a non-human ES cell) can be incubated until the blastocyst stage before being implanted into and gestated in the surrogate mother to produce an F0 non-human animal. The surrogate mother can then produce an F0 generation non-human animal comprising a CRISPR reporter.

The methods can further comprise identifying a cell or animal having a modified target genomic locus. Various methods can be used to identify cells and animals having a targeted genetic modification.

The screening step can comprise, for example, a quantitative assay for assessing modification of allele (MOA) of a parental chromosome. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence.

Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, incorporated herein by reference in its entirety for all purposes).

An example of a suitable pluripotent cell is an embryonic stem (ES) cell (e.g., a mouse ES cell or a rat ES cell). The modified pluripotent cell can be generated, for example, by (a) introducing into the cell one or more targeting vectors comprising an insert nucleic acid flanked by 5' and 3' homology arms corresponding to 5' and 3' target sites, wherein the insert nucleic acid comprises a CRISPR reporter; and (b) identifying at least one cell comprising in its genome the insert nucleic acid integrated at the target genomic locus. Alternatively, the modified pluripotent cell can be generated by (a) introducing into the cell: (i) a nuclease agent, wherein the nuclease agent induces a nick or double-strand break at a target sequence within the target genomic locus; and (ii) one or more targeting vectors comprising an insert nucleic acid flanked by 5' and 3' homology arms corresponding to 5' and 3' target sites located in sufficient proximity to the target sequence, wherein the insert nucleic acid comprises a CRISPR reporter; and (c) identifying at least one cell comprising a modification (e.g., integration of the insert nucleic acid) at the target genomic locus. Any nuclease agent that induces a nick or double-strand break into a desired target sequence can be used. Examples of suitable nucleases include a Transcription Activator-Like Effector Nuclease (TALEN), a zinc-finger nuclease (ZFN), a meganuclease, and Clustered Regularly Interspersed Short Palindromic Repeats (CRISPR)/CRISPR-associated (Cas) systems or components of such systems (e.g., CRISPR/Cas9). See, e.g., US 2013/0309670 and US 2015/0159175, each of which is herein incorporated by reference in its entirety for all purposes.

The donor cell can be introduced into a host embryo at any stage, such as the blastocyst stage or the pre-morula stage (i.e., the 4 cell stage or the 8 cell stage). Progeny that are capable of transmitting the genetic modification though the germline are generated. See, e.g., U.S. Pat. No. 7,294,754, herein incorporated by reference in its entirety for all purposes.

Alternatively, the method of producing the non-human animals described elsewhere herein can comprise: (1) modifying the genome of a one-cell stage embryo to comprise the CRISPR reporter using the methods described above for modifying pluripotent cells; (2) selecting the genetically modified embryo; and (3) implanting and gestating the genetically modified embryo into a surrogate mother. Progeny that are capable of transmitting the genetic modification though the germline are generated.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods, oocytes are generally retrieved from deceased animals, although they may be isolated also from either oviducts and/or ovaries of live animals. Oocytes can be matured in a variety of well-known media prior to enucleation. Enucleation of the oocyte can be performed in a number of well-known manners. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in well-known media and then transferred to the womb of an animal. See, e.g., US 2008/0092249, WO 1999/005266, US 2004/0177390, WO 2008/017234, and U.S. Pat. No. 7,612,250, each of which is herein incorporated by reference in its entirety for all purposes.

The various methods provided herein allow for the generation of a genetically modified non-human F0 animal wherein the cells of the genetically modified F0 animal comprise the CRISPR reporter. It is recognized that depending on the method used to generate the F0 animal, the number of cells within the F0 animal that have the CRISPR reporter will vary. The introduction of the donor ES cells into a pre-morula stage embryo from a corresponding organism (e.g., an 8-cell stage mouse embryo) via for example, the VELOCIMOUSE® method allows for a greater percentage of the cell population of the F0 animal to comprise cells having the nucleotide sequence of interest comprising the targeted genetic modification. For example, at least 50%, 60%, 65%, 70%, 75%, 85%, 86%, 87%, 87%, 88%, 89%, 90%, 91%, 92%, 93%, 94%, 95%, 96%, 97%, 98%, 99% or 100% of the cellular contribution of the non-human F0 animal can comprise a cell population having the targeted modification.

The cells of the genetically modified F0 animal can be heterozygous for the CRISPR reporter or can be homozygous for the CRISPR reporter.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus.

TABLE 2

Description of Sequences.

| SEQ ID NO | Type | Description |
|---|---|---|
| 1 | DNA | Complementary Strand of Pgk Poly(A) Excision Guide RNA Recognition Sequence v1 |
| 2 | RNA | Pgk Poly(A) Excision Guide Sequence v1 (gRNA#16; pA removal guide) |
| 3 | Protein | T2A |
| 4 | Protein | P2A |
| 5 | Protein | E2A |
| 6 | Protein | F2A |
| 7 | RNA | Generic Guide RNA Scaffold v.2 |
| 8 | RNA | Generic Guide RNA Scaffold v.3 |
| 9 | RNA | Generic Guide RNA Scaffold v.4 |
| 10 | DNA | Generic Guide RNA Target Sequence Plus PAM v.1 |
| 11 | DNA | Generic Guide RNA Target Sequence Plus PAM v.2 |
| 12 | DNA | Generic Guide RNA Target Sequence Plus PAM v.3 |
| 13 | DNA | Complementary Strand of eBFP Guide RNA Recognition Sequence |
| 14 | RNA | eBFP Guide Sequence |
| 15 | DNA | eBFP to eGFP Repair Donor - ssODN F |
| 16 | DNA | eBFP to eGFP Repair Donor - ssODN R |
| 17 | DNA | LSL-LacZ-P2A-eBFP/eGFP Reporter Allele (MAID2634) |
| 18 | DNA | LSL-eBFP/eGFP Reporter Allele (MAID2652) |
| 19 | DNA | Complementary Strand of Pgk Poly(A) Excision Guide RNA Recognition Sequence v2 |
| 20 | RNA | Pgk Poly(A) Excision Guide Sequence v2 (LSL_LacZ_gU2) |
| 21 | DNA | Complementary Strand of Pgk Poly(A) Excision Guide RNA Recognition Sequence v3 |
| 22 | RNA | Pgk Poly(A) Excision Guide Sequence v3 (LSL_LacZ_gU3) |
| 23 | DNA | Complementary Strand of Pgk Poly(A) Excision Guide RNA Recognition Sequence v4 |
| 24 | RNA | Pgk Poly(A) Excision Guide Sequence v4 (LSL_LacZ_gU1) |
| 25 | DNA | Complementary Strand of Pgk Poly(A) Excision Guide RNA Recognition Sequence v5 |
| 26 | RNA | Pgk Poly(A) Excision Guide Sequence v5 (LSL_LacZ_gD2) |
| 27 | DNA | Complementary Strand of Pgk Poly(A) Excision Guide RNA Recognition Sequence v6 |
| 28 | RNA | Pgk Poly(A) Excision Guide Sequence v6 (LSL_LacZ_gD1) |
| 29 | RNA | Pgk Poly(A) Disruption Guide Sequence v1 (cGM2) |
| 30 | RNA | Pgk Poly(A) Disruption Guide Sequence v2 (cGM) |
| 31 | RNA | Pgk Poly(A) Disruption Guide Sequence v3 (cGM3) |
| 32 | DNA | Complementary Strand of Pgk Poly(A) Disruption Guide RNA Recognition Sequence v1 (cGM2) |
| 33 | DNA | Complementary Strand of Pgk Poly(A) Disruption Guide RNA Recognition Sequence v2 (cGM) |
| 34 | DNA | Complementary Strand of Pgk Poly(A) Disruption Guide RNA Recognition Sequence v3 (cGM3) |
| 35 | RNA | Pgk Poly(A) Disruption Guide Sequence v4 cGM4 |
| 36 | RNA | Pgk Poly(A) Disruption Guide Sequence v5 cGM5 |
| 37 | RNA | crRNA Tail |
| 38 | RNA | TracrRNA |
| 39 | RNA | Generic Guide RNA Scaffold v.1 |
| 40 | RNA | Cre mRNA |

TABLE 2-continued

Description of Sequences.

| SEQ ID NO | Type | Description |
|---|---|---|
| 41 | DNA | Pgk Poly(A) Excision Guide RNA Target Sequence v1 (gRNA#16; pA removal guide) |
| 42 | DNA | eBFP Guide RNA Target Sequence |
| 43 | DNA | Pgk Poly(A) Excision Guide RNA Target Sequence v2 (LSL_LacZ_gU2) |
| 44 | DNA | Pgk Poly(A) Excision Guide RNA Target Sequence v3 (LSL_LacZ_gU3) |
| 45 | DNA | Pgk Poly(A) Excision Guide RNA Target Sequence v4 (LSL_LacZ_gU1) |
| 46 | DNA | Pgk Poly(A) Excision Guide RNA Target Sequence v5 (LSL_LacZ_gD2) |
| 47 | DNA | Pgk Poly(A) Excision Guide RNA Target Sequence v6 (LSL_LacZ_gD1) |
| 48 | DNA | Pgk Poly(A) Disruption Guide RNA Target Sequence v1 (cGM2) |
| 49 | DNA | Pgk Poly(A) Disruption Guide RNA Target Sequence v2 (cGM) |
| 50 | DNA | Pgk Poly(A) Disruption Guide RNA Target Sequence v3 (cGM3) |
| 51 | DNA | Pgk Poly(A) Disruption Guide RNA Target Sequence v4 cGM4 |
| 52 | DNA | Pgk Poly(A) Disruption Guide RNA Target Sequence v5 cGM5 |
| 53 | Protein | Cas9 Protein |
| 54 | DNA | Cas9 Coding Sequence |
| 55 | RNA | eBFP Guide Sequence |
| 56 | DNA | eBFP Guide Target Sequence |
| 57 | DNA | L-eBFP CRISPR Reporter Allele (MAID20090) |
| 58 | DNA | L-LacZ: eBFP CRISPR Reporter Allele (MAID2809) |
| 59 | DNA | L-LacZ: eGFP CRISPR Reporter Allele |
| 60 | DNA | L-eGFP CRISPR Reporter Allele |

EXAMPLES

Example 1

Validation of CRISPR Reporters

The CRISPR/Cas9 technology is a promising new therapeutic modality. Assessing the efficiency of mutation generation or targeted gene modification by an introduced CRISPR/Cas9 agent in vivo currently relies on difficult molecular assays, such as single-strand DNase sensitivity assays, digital PCR, or next generation sequencing.

CRISPR/Cas9, an RNA-guided DNA endonuclease, catalyzes the double strand break (DSB) of DNA at the binding site of its RNA guide. The RNA guide can consist of a 42-nucleotide CRISPR RNA (crRNA) that joins with an 87-nucleotide trans-activating RNA (tracrRNA). The tracrRNA is complementary to and base pairs with the crRNA to form a functional crRNA/tracrRNA guide. This duplex RNA becomes bound to the Cas9 protein to form an active ribonucleoprotein (RNP) that can interrogate the genome for the specific seed sequence. A secondary requirement for strand breakage is that the Cas9 protein must recognize a protospacer adjacent motif (PAM) directly adjacent to the 3' CRISPR target sequence. Alternatively, an active RNP complex can also be formed by replacing the crRNA/tracrRNA duplex with a single chimeric RNA (sgRNA). This sgRNA can be formed by fusing the 20 nucleotide seed sequence directly to the processed tracrRNA sequence. The sgRNA can interact with both the Cas9 protein and the DNA in the same way and with similar efficiency as the crRNA/tracrRNA duplex would. This bacterial natural defense mechanism has been shown to function effectively in mammalian cells and activate break induced endogenous repair pathways. When a double strand break occurs in the genome, repair pathways will attempt to fix the DNA by either the error prone non-homologous end joining (NHEJ) pathway or homology-directed repair (HDR) if an appropriate template is available. We can leverage these pathways to facilitate site specific deletion of genomic regions or HDR in mammalian cells.

Figure 2:
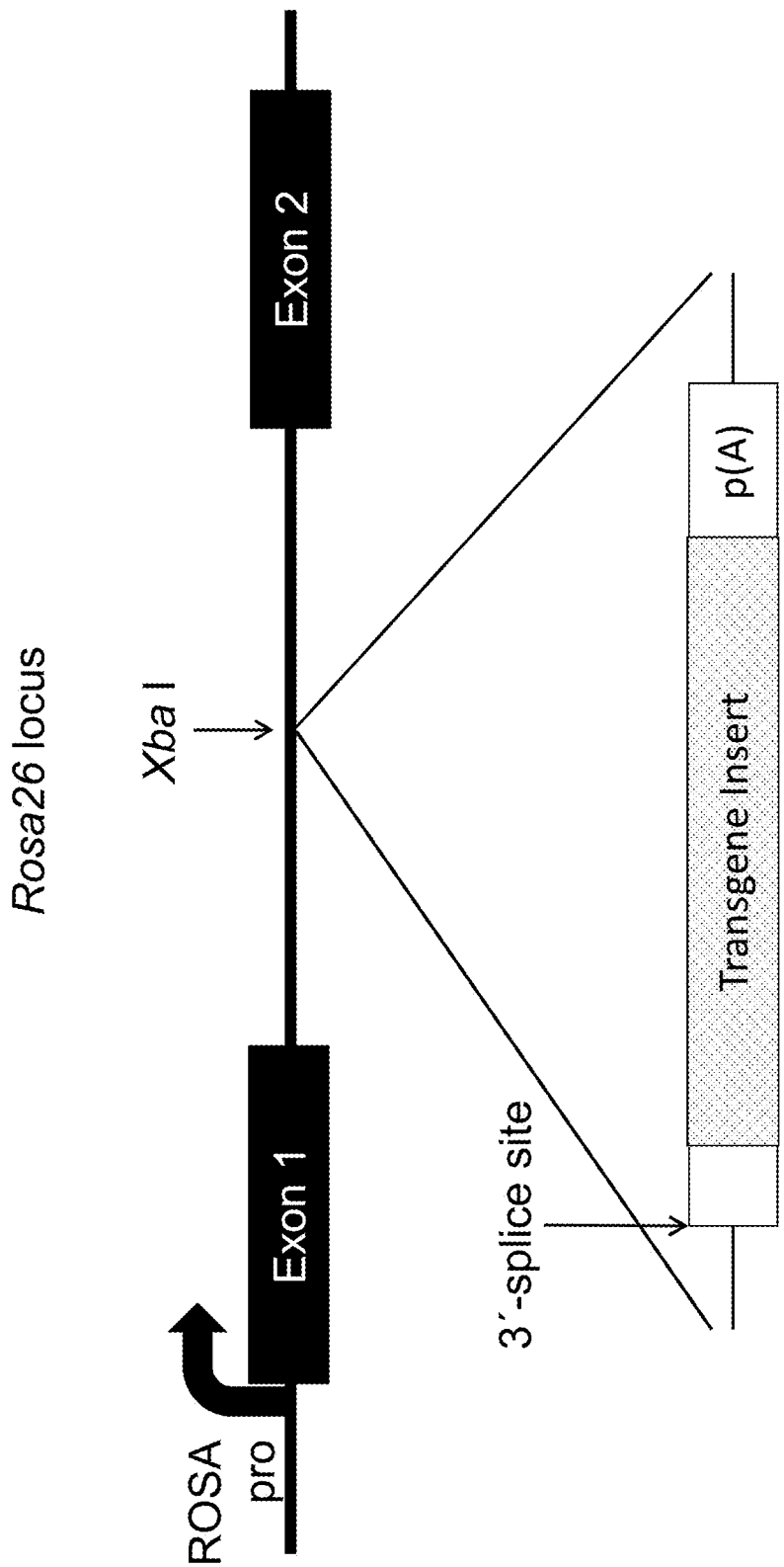
FIG. 2 shows a general schematic for targeting a transgene into the first intron of the Rosa26 locus.

To provide better assays of CRISPR/Cas9 delivery to and activity in tissues and organs of a live animal, mice were developed carrying genetic alleles that have the ability to report CRISPR/Cas9-induced non-homologous end joining (NHEJ) (e.g., Cas9-mediated excision caused by a pair of Cas9-mediated cleavage events) and/or CRISPR/Cas9-induced homology-directed repair (HDR) using a donor sequence to convert eBFP to eGFP (or eGFP to eBFP) following a Cas9-mediated single-strand or double-strand cleavage event. The CRISPR reporter alleles described in this example are based on modification of the mouse Gt(ROSA)26Sor (Rosa26) locus. The Rosa26 locus exhibits strong and ubiquitous expression of a long non-coding RNA of unknown function. Mice with a homozygous deletion of Rosa26 are viable, healthy, and fertile. The first general property of the first CRISPR reporter allele described herein is that CRISPR/Cas9-induced excision of a polyadenylation signal will activate expression of reporter proteins being expressed from the Rosa26 promoter, and the reporter proteins can then be detected by enzymatic activity or by fluorescence (or an immune assay or other means). The second general property of the first CRISPR reporter allele described herein (and the property of the second CRISPR reporter allele described herein) is that CRISPR/Cas9-induced recombination of a gene encoding a first fluorescent reporter protein with a donor sequence will convert the first fluorescent reporter protein being expressed from the Rosa26 promoter into a different second fluorescent reporter protein which can then be detected by fluorescence. The CRISPR reporter alleles described in this example were targeted to the first intron of the Rosa26 locus (see FIG. 2) and take advantage of the strong universal expression of the Rosa26 locus and the ease of targeting the Rosa26 locus.

The first CRISPR reporter allele (i.e., the LSL-LacZ: eBFP CRISPR reporter allele) is depicted in FIG. 1A and in SEQ ID NO: 17. It uses lacZ as a high definition histological reporter and eBFP (or alternatively eGFP) as a fluorescent reporter of the extent and location of CRISPR/Cas9-mediated NHEJ action (e.g., excision of a target sequence) in the liver or other target organs and uses eGFP (or alternatively eBFP) as a fluorescent reporter of the extent and location of delivered CRISPR/Cas9-induced HDR following recombination with a donor nucleic acid in the liver or other target organs. In addition, if only one organ is being targeted, the CRISPR reporter allele can also be used to assess off-target effects in other organs and tissues. Accordingly, the CRISPR reporter allele can be used to test and optimize CRISPR/Cas9 delivery methods in vivo. The components of the first CRISPR reporter allele from 5' to 3' are shown in Table 3 and in SEQ ID NO: 17. The sequence of the first CRISPR reporter allele after treatment with Cre recombinase to remove the first Pgk polyadenylation signal is set forth in SEQ ID NO: 58. The sequence of the Cre-treated reporter allele after conversion of eBFP to eGFP (e.g., after treatment with ssODN as described in more detail below) is set forth in SEQ ID NO: 59.

TABLE 3

LSL-LacZ: eBFP CRISPR Reporter Allele.

| Component | Nucleotide Region(s) Within SEQ ID NO: 17 |
|---|---|
| First loxP site | 248-281 |
| Pgk poly(A) excision guide RNA target sequence v1A for excising polyadenylation signal | 305-327 |
| First Pgk polyadenylation signal | 336-796 |
| Poly(A) recognition motif AATAAA | 371-376 |
| Multiple Pgk poly(A) disruption guide RNA target sequences within the Pgk polyadenylation signal | 337-356 |
|  | 385-404 |
|  | 405-424 |
|  | 452-471 |
|  | 571-590 |
| Pgk poly(A) excision guide RNA target sequence v1B for excising polyadenylation signal | 797-819 |
| Second loxP site | 820-853 |
| LacZ gene | 862-3930 |
| P2A coding sequence | 3931-3996 |
| eBFP coding sequence | 3997-4713 |
| eBFP guide RNA target sequence within eBFP coding sequence for converting eBFP to eGFP | 4193-4212 |
| SV40 polyadenylation signal | 4748-4969 |
| Frt site | 4976-5023 |
| Human ubiquitin C promoter | 5030-6242 |
| EM7 promoter | 6243-6309 |
| Sequence encoding neomycin phosphotransferase for resistance to neomycin family antibiotics (e.g. G418) | 6310-7113 |
| Second Pgk polyadenylation signal | 7122-7598 |
| Second Frt site | 7609-7656 |

Alternate guide RNA target sequences flanking the first Pgk polyadenylation signal can also be used. A table summarizing different guide RNA target sequences in the first CRISPR reporter, their nucleotide positions in the first CRISPR reporter, and the guide sequences within the corresponding guide RNAs targeting those guide RNA target sequences are provided in Table 4. Table 4 also provide the positions of the first and second loxP sites, the first Pgk polyadenylation signal, and the eBFP coding sequence for reference.

TABLE 4

Locations of Guide RNA Target Sequences in LSL-LacZ: eBFP CRISPR Reporter Allele.

| Guide RNA Target Sequence or Other Region (SEQ ID NO) | Nucleotide Region Within SEQ ID NO: 17 | Guide Sequence in Guide RNA (SEQ ID NO) |
|---|---|---|
| Pgk poly(A) excision guide RNA target sequence v2 (SEQ ID NO: 43) | 215-234 | Pgk poly(A) excision guide sequence v2 (SEQ ID NO: 20) |
| Pgk poly(A) excision guide RNA target sequence v4 (SEQ ID NO: 45) | 243-262 | Pgk poly(A) excision guide sequence v4 (SEQ ID NO: 24) |
| First loxP site | 248-281 | N/A |

TABLE 4-continued

Locations of Guide RNA Target Sequences in LSL-LacZ: eBFP CRISPR Reporter Allele.

| Guide RNA Target Sequence or Other Region (SEQ ID NO) | Nucleotide Region Within SEQ ID NO: 17 | Guide Sequence in Guide RNA (SEQ ID NO) |
|---|---|---|
| Pgk poly(A) excision guide RNA target sequence v3 (SEQ ID NO: 44) | 263-282 | Pgk poly(A) excision guide sequence v3 (SEQ ID NO: 22) |
| Pgk poly(A) excision guide RNA target sequence v1A (SEQ ID NO: 41) | 305-327 | Pgk poly(A) excision guide sequence v1A (SEQ ID NO: 2) |
| First Pgk polyadenylation signal | 336-796 | N/A |
| Pgk Poly(A) disruption guide RNA target sequence v4 (SEQ ID NO: 51) | 357-356 | Pgk Poly(A) disruption guide sequence v4 (SEQ ID NO: 35) |
| Pgk Poly(A) disruption guide RNA target sequence v5 (SEQ ID NO: 52) | 385-404 | Pgk Poly(A) disruption guide sequence v5 (SEQ ID NO: 36) |
| Pgk Poly(A) disruption guide RNA target sequence v1 (SEQ ID NO: 48) | 405-424 | Pgk Poly(A) disruption guide sequence v1 (SEQ ID NO: 29) |
| Pgk Poly(A) disruption guide RNA target sequence v2 (SEQ ID NO: 49) | 452-471 | Pgk Poly(A) disruption guide sequence v2 (SEQ ID NO: 30) |
| Pgk Poly(A) disruption guide RNA target sequence v3 (SEQ ID NO: 50) | 571-590 | Pgk Poly(A) disruption guide sequence v3 (SEQ ID NO: 31) |
| Pgk poly(A) excision guide RNA target sequence v5 (SEQ ID NO: 46) | 794-813 | Pgk poly(A) excision guide sequence v5 (SEQ ID NO: 26) |
| Pgk poly(A) excision guide RNA target sequence v1B (SEQ ID NO: 41) | 797-819 | Pgk poly(A) excision guide sequence v1B (SEQ ID NO: 2) |
| Pgk poly(A) excision guide RNA target sequence v6 (SEQ ID NO: 47) | 803-822 | Pgk poly(A) excision guide sequence v6 (SEQ ID NO: 28) |
| Second loxP site | 820-853 | N/A |
| eBFP coding sequence | 3997-4713 | N/A |
| eBFP Guide RNA target sequence (SEQ ID NO: 42) | 4193-4212 | eBFP guide sequence (SEQ ID NO: 14) |

The first Pgk polyadenylation signal normally blocks expression of the beta-galactosidase protein from the lacZ gene and the eBFP protein. Upon excision of the first Pgk polyadenylation signal following cleavage of the guide RNA target sequences flanking the first Pgk polyadenylation signal (SEQ ID NO: 41 for each, or SEQ ID NO: 41, 43, 44, or 45 for the first guide RNA target sequence and SEQ ID NO: 41, 46, or 47 for the second guide RNA target sequence) by a Cas9 nuclease, the lacZ gene and the eBFP coding sequence will normally be expressed. A beta-galactosidase protein and an eBFP protein are then expressed and can be used to quantify the cells modified by the CRISPR/Cas9-induced excision via NHEJ.

Upon recognition and cleavage of the guide RNA target sequence within the eBFP coding sequence (SEQ ID NO: 42) by a Cas9 nuclease and induction of repair with a donor sequence, the eBFP coding sequence in the CRISPR reporter allele can be repaired by homology-directed repair to convert it into an eGFP coding sequence. An eGFP protein is then expressed and can be used to quantify the cells modified by the combination of the CRISPR/Cas9 and the donor sequence via HDR. The guide sequence of a guide RNA used to target the eBFP coding sequence comprises the sequence set forth in SEQ ID NO: 14, and a donor nucleic acid that can be used to repair the eBFP coding sequence and convert it to an eGFP coding sequence is set forth in SEQ ID NO: 15 or SEQ ID NO: 16.

Figure 3:
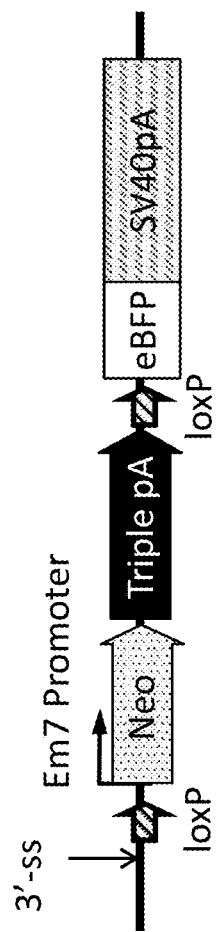
FIG. 3 shows a LSL-eBFP CRISPR reporter allele (MAID2652; not to scale) comprising from 5' to 3': a 3' splicing sequence; a first loxP site; an Em7 promoter; a neomycin resistance gene coding sequence; a triple polyadenylation signal; a second loxP site; an enhanced blue fluorescent protein (eBFP) coding sequence; and an SV40 polyadenylation signal.

The second CRISPR reporter allele (i.e., the LSL-eBFP CRISPR reporter allele) is depicted in FIG. 3 and SEQ ID NO: 18 and can be used to directly assess CRISPR/Cas9-induced HDR. It uses eGFP (or alternatively eBFP) as a fluorescent reporter of the extent and location of CRISPR/Cas9-induced HDR following recombination with a donor nucleic acid in the liver or other target organs. In addition, if only one organ is being targeted, the CRISPR reporter allele can also be used to assess off-target effects in other organs and tissues. Accordingly, the CRISPR reporter allele can be used to test and optimize CRISPR/Cas9 delivery methods in vivo. The components of the second CRISPR reporter allele from 5' to 3' are shown in the Table 5 and SEQ ID NO: 18. The sequence of the second CRISPR reporter allele after treatment with Cre recombinase to remove the selection cassette is set forth in SEQ ID NO: 57. The sequence of the Cre-treated reporter allele after conversion of eBFP to eGFP (e.g., after treatment with ssODN as described in more detail below) is set forth in SEQ ID NO: 60).

TABLE 5

LSL-eBFP CRISPR Reporter Allele.

| Component | Nucleotide Region Within SEQ ID NO: 18 |
|---|---|
| First loxP site | 226-259 |
| EM7 promoter | 357-423 |
| Sequence encoding neomycin phosphotransferase for resistance to neomycin family antibiotics (e.g. G418) | 424-1227 |
| Triple polyadenylation signal | 1236-2489 |
| Second loxP site | 2517-2550 |
| eBFP coding sequence | 2596-3315 |
| Guide RNA target sequence within eBFP coding sequence for converting eBFP to eGFP | 2795-2814 |
| SV40 polyadenylation signal | 3350-3571 |

The triple polyadenylation signal blocks expression of the eBFP protein. Upon excision of the polyadenylation signal by a Cre recombinase, the eBFP coding sequence will be expressed. Upon recognition and cleavage of the guide RNA target sequence within the eBFP coding sequence (SEQ ID NO: 42) by a Cas9 nuclease and induction of repair with a donor sequence, the eBFP coding sequence in CRISPR reporter allele can be repaired by homology-directed repair to convert it into an eGFP coding sequence. An eGFP protein is then expressed and can be used to quantify the cells modified by the combination of the CRISPR/Cas9 and the donor sequence via HDR. The guide sequence of the guide RNA used to target the eBFP coding sequence comprises the sequence set forth in SEQ ID NO: 14, and a donor nucleic acid that can be used to repair the eBFP coding sequence and convert it to an eGFP coding sequence is set forth in SEQ ID NO: 15 or SEQ ID NO: 16.

LacZ is a naturally occurring gene in *E. coli* that encodes the protein beta-galactosidase. This protein is responsible for the breakdown of lactose by cleaving the bond between the two carbon rings in lactose to produce glucose and galactose. Originally used in *E. coli*, lacZ is an important gene in research as it can be used as a histochemical reporter. When in the presence of lactose analog X-Gal, beta-galactosidase will hydrolyze the substrate to produce a blue color that is easily visualized under a microscope.

Enhanced Green Fluorescent Protein (eGFP) is a protein that emits a green fluorescence when exposed to light in the blue to ultraviolet range. eGFP was derived from the GFP originally isolated from the jellyfish *Aequorea victoria*. Mutations were engineered that increased fluorescence and photostability as well as allowed proper folding at 37° C. for use in mammalian cells. The major excitation peak is 488 nanometers (nm) with peak emission at 509 nm. A single mutation, Y66H, converts eGFP into enhanced Blue Fluorescent Protein (eBFP) with major excitation peak is shifted to 380 nm with peak emission at 448 nm. We have engineered the expression of lacZ and a P2A linked eBFP into the first intron of mouse Rosa26 locus with a preceding foxed poly(A) sequence and appropriate splicing signals. Prior to floxing out the poly(A), the lacZ and eBFP coding sequences will not be expressed as the poly(A) region will block transcription. Upon floxing out the poly(A), beta-galactosidase and eBFP proteins will be constitutively expressed by the Rosa26 promoter. Alternatively, the poly (A) can be removed using the Cas9 system to delete the region by incorporating two sgRNA sites flanking the sequence. Pre- and post-floxed targeted cells are first verified by TAQMAN® quantitative Polymerase Chain Reaction (qPCR) to detect the single, site specific, integration of the targeting vector at Rosa26.

The Lox-Stop-Lox (LSL) LacZ-2A-eBFP allele as depicted in FIG. 1A (or alternatively, a LSL LacZ-2A-eGFP allele) can be an effective NHEJ and HDR reporter in mouse embryonic stem cells (mESCs) as well as in adult mouse tissue. By incorporating this allele into Rosa26, lacZ or eBFP will not normally not be expressed in cells and tissues. Introduction of the sgRNA to drop out the poly(A) along with Cas9 protein can turn on lacZ and eBFP expression. If no repair template is provided, this deletion can take place using the NHEJ pathway. In this way, this allele can be used to indicate when and where NHEJ has taken place within an adult mouse. Further, a guide RNA can then be introduced to induce double strand break in eBFP, and a repair donor containing an H66Y mutation to convert eBFP to eGFP (or alternatively, for a LSL LacZ-2A-eGFP allele, a repair donor containing a Y66H mutation to convert eGFP to eBFP).

Figure 4A:
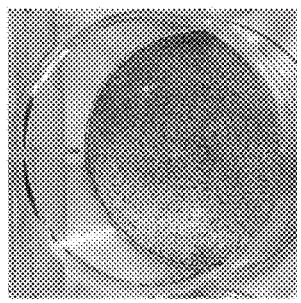
FIGS. 4A-4E show lacZ-stained mouse embryonic stem cells (mESCs) comprising the LSL-LacZ:eBFP CRISPR reporter allele. The cells in FIG. 4A are untreated, the cells in FIG. 4B were electroporated with a Cre recombinase plasmid to excise the first Pgk polyadenylation signal, the cells in FIG. 4C were electroporated with a ribonucleoprotein complex comprising Cas9 protein complexed together with the gU3 and gD1 synthetic sgRNAs to target the first Pgk polyadenylation signal for excision, the cells in FIG. 4D were electroporated with a ribonucleoprotein complex comprising Cas9 protein complexed together with the gU3 and gD2 synthetic sgRNAs to target the first Pgk polyadenylation signal for excision, and the cells in FIG. 4E were electroporated with a ribonucleoprotein complex comprising Cas9 protein complexed together with the gU2 and gD1 synthetic sgRNAs to target the first Pgk polyadenylation signal for excision.
Figure 4B:
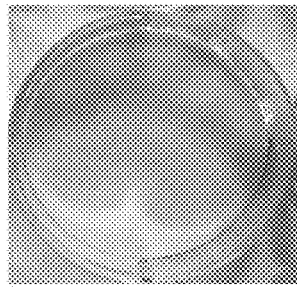
Figure 4E:
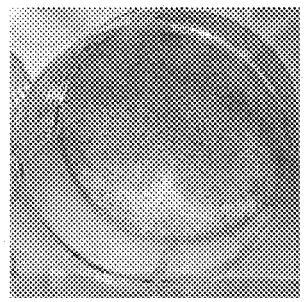
Figure 4D:
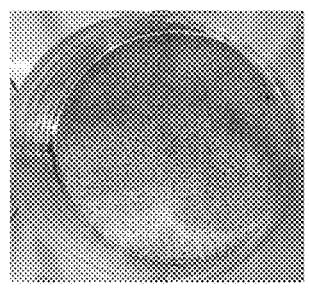
Figure 4C:
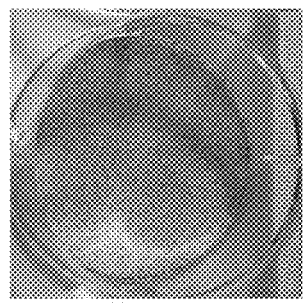

LacZ can be turned on in mESCs targeted with the CRISPR allele as shown in FIG. 1A by deleting the poly(A) region by either the Cre-Lox system or Cas9-induced NHEJ. To test the ability of CRISPR/Cas9 to delete the poly(A) region in the LSL-LacZ:eBFP CRISPR reporter allele, embryonic stem cells comprising the reporter allele were electroporated with ribonucleoprotein complexes of Cas9 and various guide RNAs designed to target upstream and downstream of the poly(A) region. The cells were plated onto 6-well plates (3×10⁵ cells) and stained for LacZ for two hours 3 days post-electroporation. The results are shown in FIGS. 4A-4E. The figures show untreated cells (FIG. 4A), cells electroporated with a plasmid encoding Cre recombinase (FIG. 4B), and cells electroporated with ribonucleoprotein complexes comprising Cas9 protein complexed together with synthetic sgRNAs targeting guide RNA target sequences flanking the Pgk polyadenylation signal upstream of the lacZ gene (FIGS. 4C-4E). As shown in FIG. 4B compared to FIG. 4A, treatment with the Cre recombinase plasmid activated expression of lacZ. Likewise, as shown in FIGS. 4C-4E compared to FIG. 4A, treatment with the CRISPR/Cas9 activated expression of lacZ, confirming that the upstream polyadenylation signal had been excised. The cells in FIG. 4C were targeted with the gU3 and gD1 sgRNAs targeting Pgk poly(A) excision guide RNA target sequences v3 and v6 (SEQ ID NOS: 44 and 47, respectively). These guide RNAs included the sequences set forth in SEQ ID NOS: 22 and 28, respectively. The cells in FIG. 4D were targeted with the gU3 and gD2 sgRNAs targeting Pgk poly(A) excision guide RNA target sequences v3 and v5 (SEQ ID NOS: 44 and 46, respectively). These guide RNAs included the sequences set forth in SEQ ID NOS: 22 and 26, respectively. The cells in FIG. 4E were targeted with the gU2 and gD1 sgRNAs targeting Pgk poly(A) excision guide RNA target sequences v2 and v6 (SEQ ID NOS: 43 and 47, respectively). These guide RNAs included the sequences set forth in SEQ ID NOS: 20 and 28, respectively. Similar results were obtained for the combination of the gU1 and gD1 sgRNAs, the combination of the gU1 and gD2 sgRNAs, and the gU2 and the gD2 sgRNAs (data not shown).

Figure 1B:
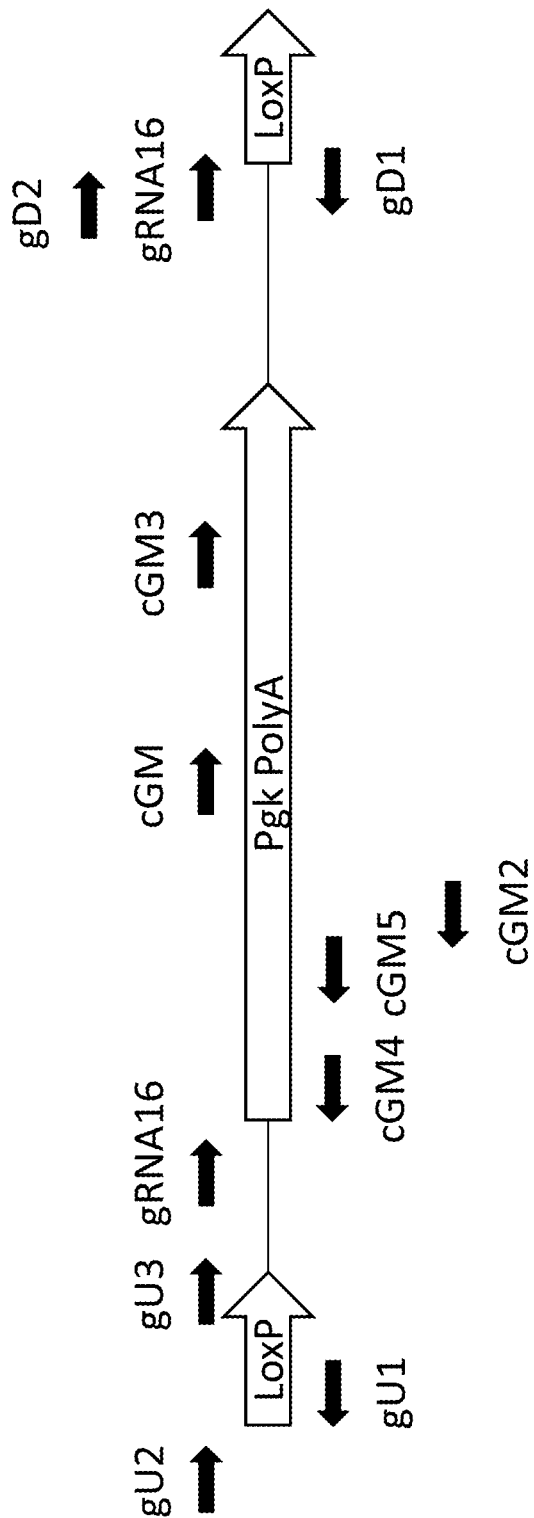
FIG. 1B shows the positions of various guide RNA target sequences in a schematic of the region of the LSL-LacZ:eBFP CRISPR reporter allele comprising the first loxP site, the first Pgk polyadenylation signal, and the second loxP site (not to scale).
Figure 5:
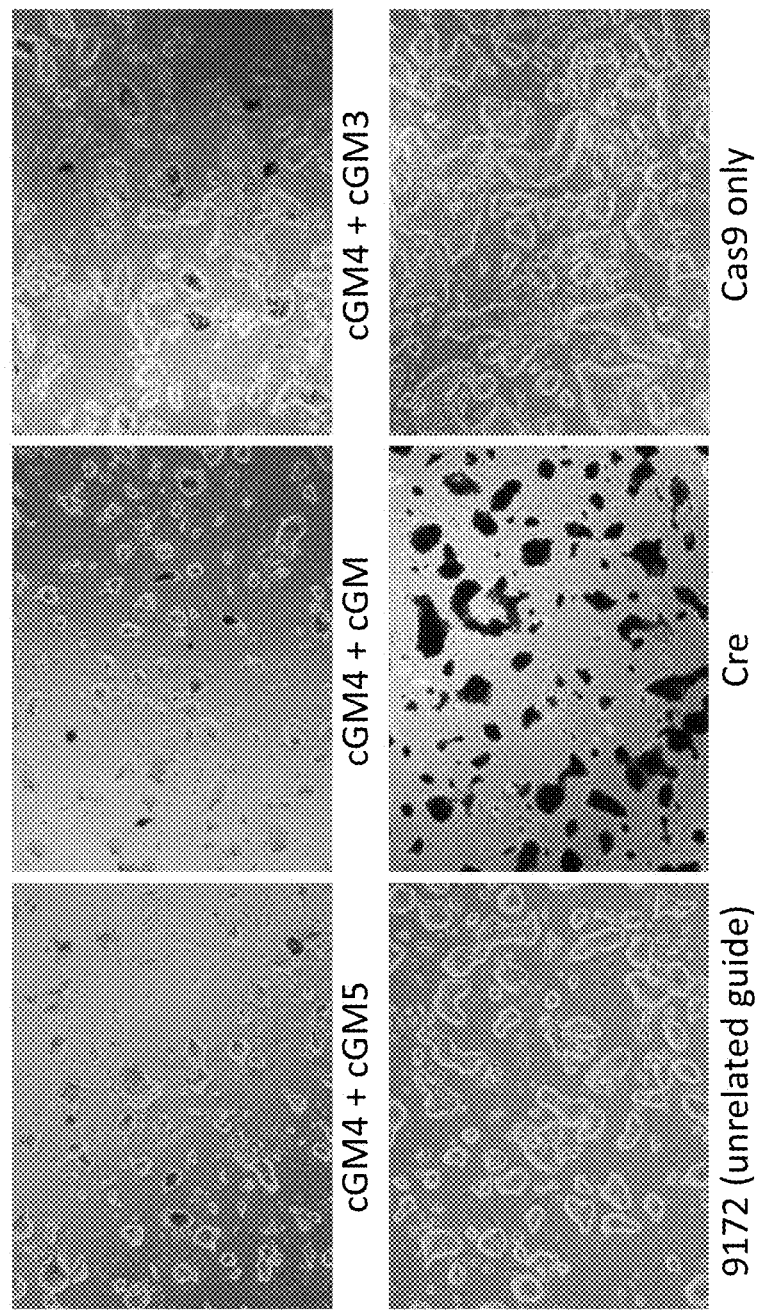
FIG. 5 shows lacZ-stained mouse embryonic stem cells (mESCs) comprising the LSL-LacZ:eBFP CRISPR reporter allele three days post-electroporation. The cells were electroporated with a ribonucleoprotein complex comprising Cas9 protein complexed together with synthetic sgRNAs cGM4 and cGM5, a ribonucleoprotein complex comprising Cas9 protein complexed together with synthetic sgRNAs cGM4 and cGM, a ribonucleoprotein complex comprising Cas9 protein complexed together with synthetic sgRNAs cGM4 and cGM3, a ribonucleoprotein complex comprising Cas9 protein complexed together with synthetic sgRNA 9172 (non-cutting control guide RNA), Cas9 protein alone, or a Cre recombinase plasmid.
Figure 6:
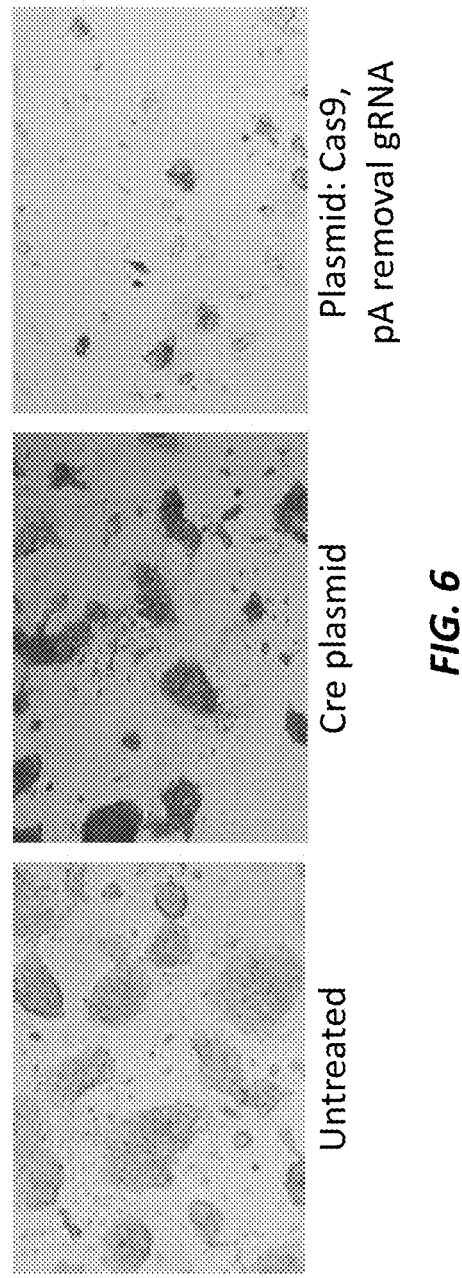
FIG. 6 shows lacZ-stained mouse embryonic stem cells (mESCs) comprising the LSL-LacZ:eBFP CRISPR reporter allele three days post-electroporation. The cells were either untreated, were electroporated with a Cas9 plasmid and sgRNA #16 plasmid, or were electroporated with a Cre recombinase plasmid.

Similar experiments were done in mouse ES cells comprising the LSL-LacZ:eBFP CRISPR reporter allele by treating with three other combinations of guide RNAs that target within the Pgk polyadenylation signal (see FIG. 1B): cGM4+cGM5, cGM4+cGM, and cGM4+cGM3. The guide RNA target sequences for cGM, cGM3, cGM4, and cGM5 are set forth in SEQ ID NOS: 49, 50, 51, and 52, respectively, and the guide RNA guide sequences are set forth in SEQ ID NOS: 30, 31, 35, and 36, respectively. The results are shown in FIG. 5. Cre was used as a positive control, and Cas9-only or Cas9+ a non-cutting guide RNA (9172) were used as negative controls. Treatment with Cas9 and each of the three combinations of guide RNAs activated expression of lacZ, confirming that the upstream polyadenylation signal had been excised. Likewise, a similar experiment was done with guide RNA #16, which has target sequences both upstream and downstream of the polyadenylation signal. The guide RNA target sequence for gRNA#16 is set forth in SEQ ID NO: 41, and the guide sequence of the guide RNA is set forth in SEQ ID NO: 2. As shown in FIG. 6, treatment with Cas9 and guide RNA #16 activated expression of lacZ, confirming that the upstream polyadenylation signal had been excised.

To determine the effectiveness of lacZ as an NHEJ readout in adult mice, mESCs targeted with the CRISPR reporter allele shown in FIG. 1A were microinjected into 8-cell mouse embryos using the VELOCIMOUSE® method. See, e.g., U.S. Pat. Nos. 7,576,259; 7,659,442; 7,294,754; US 2008/007800; and Poueymirou et al. (2007) *Nature Biotech.* 25(1):91-99, each of which is herein incorporated by reference in its entirety for all purposes. Specifically, a small hole was created in the zona pellucida to facilitate the injection of targeted mESCs. These injected 8-cell embryos were transferred to surrogate mothers to produce live pups carrying the transgene. Upon gestation in a surrogate mother, the injected embryos produced F0 mice that carry no detectable host embryo contribution. The fully ES cell-derived mice were normal, healthy, and fertile (with germline transmission). This allele can be used to evaluate the off-target editing potential of the Cas9 system. When Cas9 and sgRNA are introduced to a mouse via tail vein injection of lipid nanoparticles (LNP) or adeno-associated virus (AAV), they can edit the liver. Assessment of editing in other tissues can also be undertaken using these delivery methods. Post-injection, the various mouse tissues are harvested, and lacZ staining is completed. All tissues that are edited by the introduced Cas9 and sgRNA express lacZ, thus allowing a determination if any unexpected tissues are affected by Cas9 editing. This system can be used to evaluate additional delivery methods as well as the editing potential of various AAV serotypes.

Figure 7:
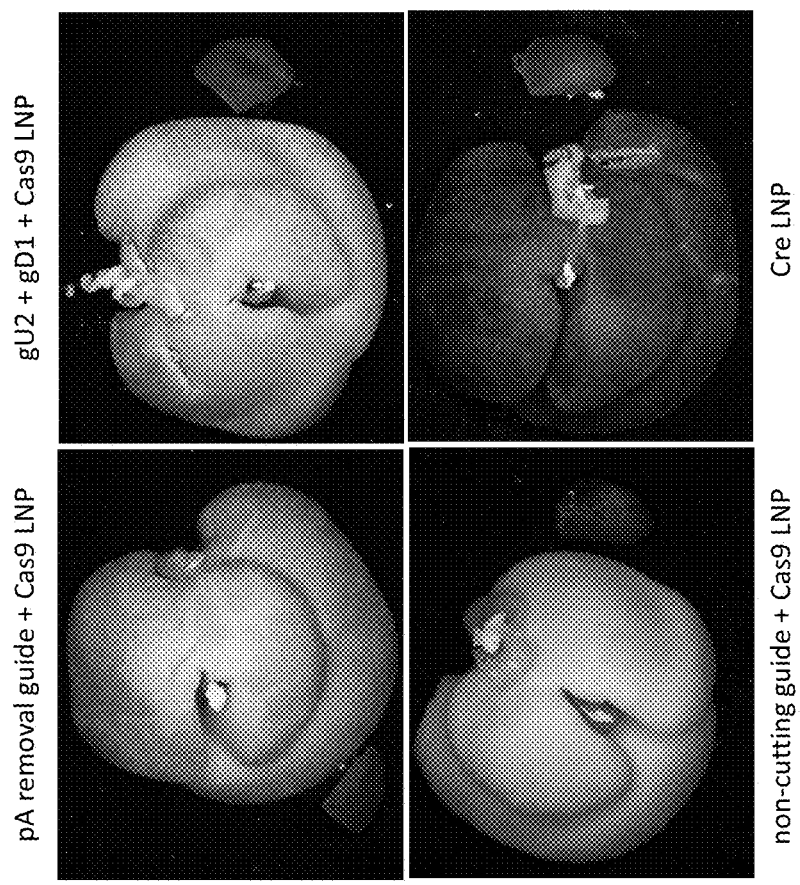
FIG. 7 shows lacZ-stained livers isolated from LSL-LacZ:eBFP mice 1 week post-injection with lipid nanoparticles comprising guide RNA, Cas9 mRNA and guide RNA, or Cre recombinase mRNA. The treatment conditions included Cas9 plus pA removal sgRNA (sgRNA #16), Cas9 together with sgRNAs gU2 and gD1, Cas9 together with a control non-cutting sgRNA, and Cre recombinase.
Figure 8:
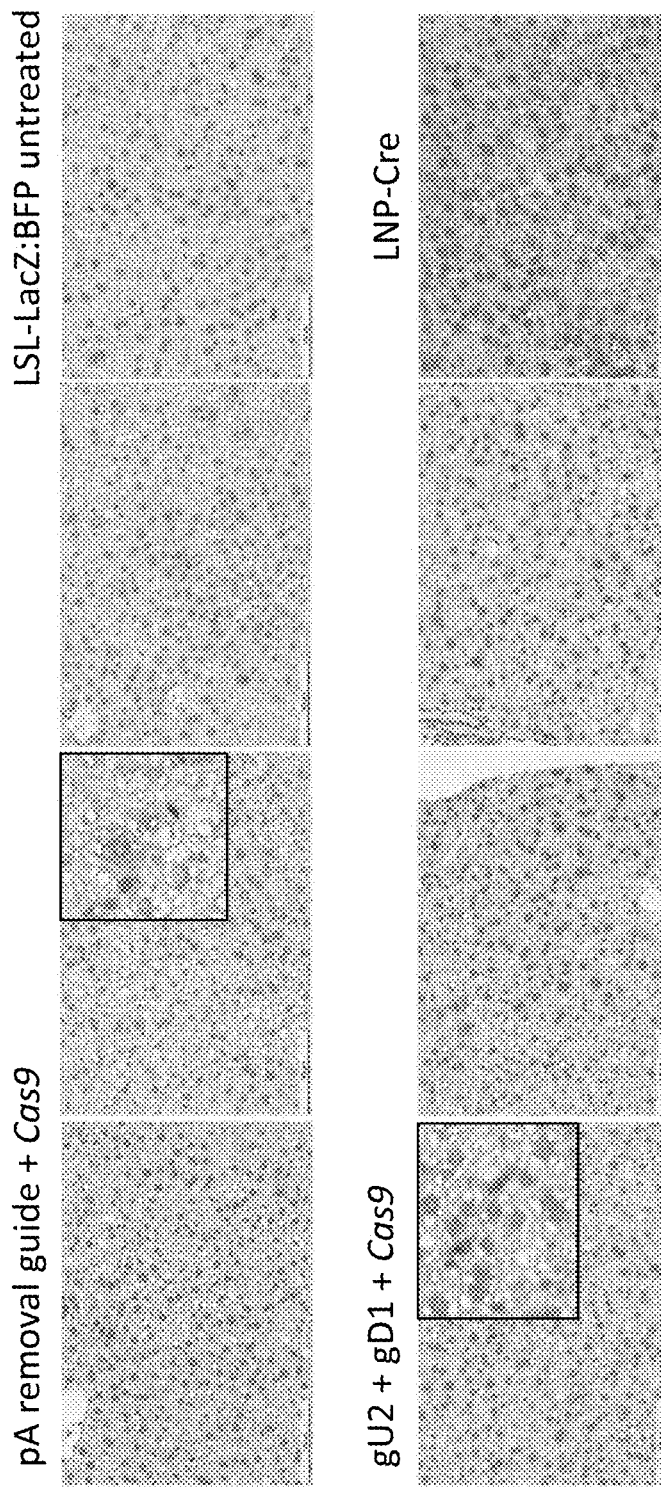
FIG. 8 shows lacZ immunohistochemistry of liver samples from LSL-LacZ:eBFP CRISPR reporter mice treated with Cas9 plus pA removal sgRNA (sgRNA #16), Cas9 together with sgRNAs gU2 and gD1, or LNP-Cre recombinase. Liver samples from untreated mice were used as a control. Brown-stained cells indicate expression of the LACZ protein.
Figure 11:
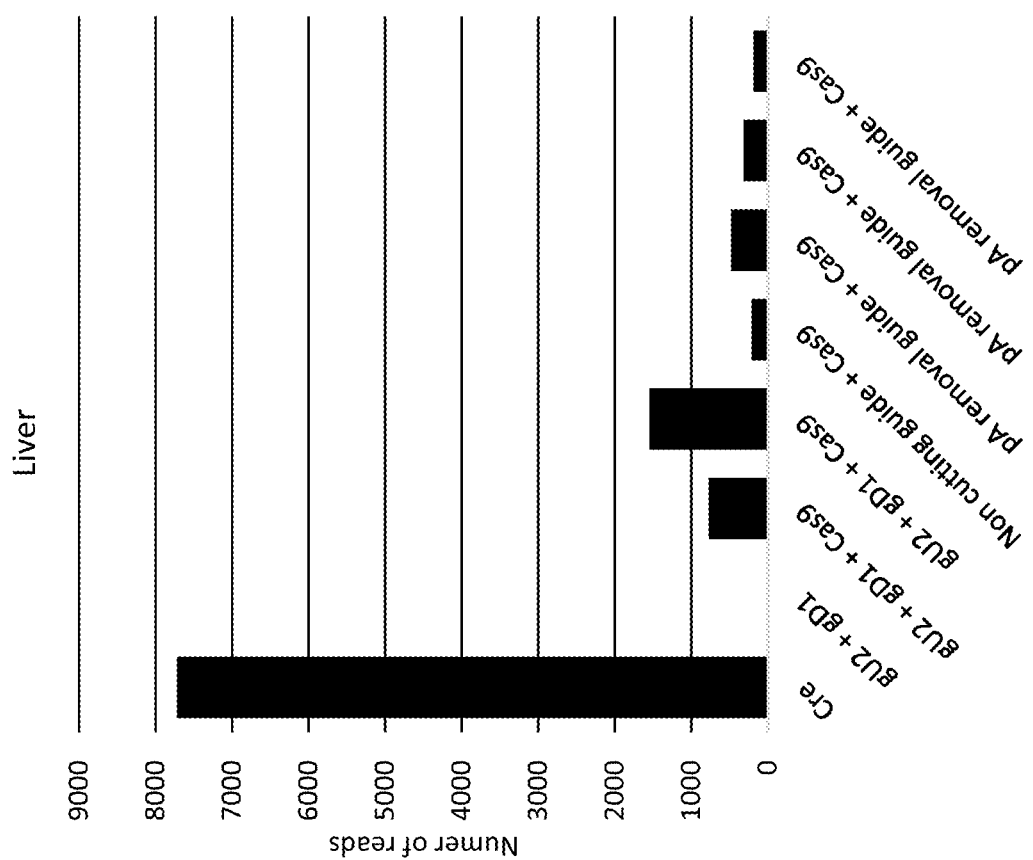
FIG. 11 shows non-homologous end joining efficiency (number of reads) as determined by next-generating sequencing in cells isolated from livers harvested from mice comprising the LSL-LacZ:eBFP CRISPR reporter allele integrated at the Rosa26 locus one week following injection with the indicated CRISPR/Cas9 or Cre recombinase components.

Mice comprising the LSL-LacZ:eBFP CRISPR reporter allele integrated at the Rosa26 locus were dosed in the following groups: (1) polyA removal guide RNA (gRNA #16)+Cas9 lipid nanoparticle (LNP) (4 mice); (2) gU2 guide RNA+gD1 guide RNA+Cas9 LNP (4 mice); (3) non-cutting guide RNA+Cas9 LNP (2 mice); and (4) Cre recombinase LNP (1 mouse). The animals were dosed with 2 mg/kg LNP in 200 µL tris-saline sucrose buffer by tail vein injection. Cas9 was in the form of mRNA, gRNA was in the form of RNA, and Cre recombinase was in the form of mRNA. One week post-injection, animals were harvested, and tissues were collected for whole mount imaging/lacZ staining, for fixing in 10% formalin for histology/immunohistochemistry, and for next-generation sequencing (NGS). The tissues that were collected included liver, spleen, pancreas, kidney, skeletal muscle, gonad, heart, lung, and brain. Results of whole mount lacZ staining of livers after 72 hours in beta-galactosidase are shown in FIG. 7. Briefly, the livers were fixed in PFA for 30 minutes on ice and were then rinsed three times for 20 minutes on ice. Staining with X-Gal was for 72 hours on ice, with agitation and washing in PBS. Livers were fixed in formalin overnight at 4° C. and then washed with PBS. The Cre-treated mice showed abundant lacZ staining, whereas the mice treated with the non-cutting guide RNA showed no staining. The two test mouse groups—polyA removal guide RNA or the combination of the gU2 and gD1 guide RNAs—both showed lacZ staining, indicating that the upstream polyadenylation signal had been excised in the livers of the mice in vivo. These results are consistent with the lacZ immunohistochemistry results shown in FIG. 8. Briefly, formalin-fixed paraffin embedded liver sections were deparraffinized followed by an antigen retrieval and then blocked. The slides were then incubated with an antibody against LACZ and bound with a secondary antibody conjugated to HRP (horseradish peroxidase). These tissues were then incubated in DAB until the positive cells exhibited a brown color. The slides were then scanned and positive cells identified. Not surprisingly, the staining was lower than that for Cre recombinase because the Cre recombinase allows for easier excision of the Pgk pA, while the guide RNAs are relying on the efficiency of NHEJ and the coinciding of the gRNA+Cas9 complex forming at two different location for collapse to occur. Similarly, these results are also consistent with the next-generation sequencing results from livers harvested from the various mice as shown in FIG. 11. As shown in FIG. 11, the editing efficiency (i.e., number of reads with a deletion between the gRNA target sequences) was higher for the gU2+gD1+Cas9 mice and the polyA removal guide RNA+Cas9 mice than the negative control mice (non-cutting guide RNA plus Cas9, or gU2+gD1 with no Cas9. Similar to the whole mount staining and the immunohistochemistry, Cre recombinase treatment resulted in even higher editing levels. These whole mount staining, immunohistochemistry, and NGS results indicate that the LSL-LacZ:eBFP CRISPR reporter can effectively be used as a reporter for CRISPR/Cas-mediated NHEJ activity in vivo. Different guide RNA target sequences can be engineered into the reporter to test different guide RNAs.

To test the ability of CRISPR/Cas9 to convert eBFP to eGFP via homology-directed repair in the LSL-LacZ:eBFP CRISPR reporter allele, embryonic stem cells comprising a Cre-recombinase-treated reporter allele genomically integrated at the Rosa26 locus (i.e., L-LacZ:eBFP CRISPR reporter allele with the upstream polyadenylation signal has been removed) are electroporated with Cas9 (20 µg) and a guide RNA that targets a target sequence in eBFP (2.5 µg) in the form of a ribonucleoprotein complex and a ssODN (35 µg) designed to convert eBFP to eGFP. The guide RNA target sequence is set forth in SEQ ID NO: 42, and the guide sequence of the guide RNA is set forth in SEQ ID NO: 14. Either of two ssODNs (F and R, representing "forward" and "reverse" complementary single strands; SEQ ID NOS: 15 and 16, respectively) are used.

A Lox-Stop-Lox (LSL) eBFP/eGFP allele as depicted in FIG. 3 can also be an effective HDR reporter in mouse embryonic stem cells (mESCs) as well as in adult mouse tissue. By incorporating the LSL-eBFP allele into Rosa26, eBFP will not normally be expressed in cells and tissues. If the triple polyadenylation signal-neomycin cassette is removed with Cre, eBFP can express. A guide RNA can be introduced to induce a double strand break in eBFP, and a repair donor containing the H66Y mutation can be introduced to convert eBFP to eGFP (or alternatively, for the LSL-eGFP reporter, induce a double strand break in eGFP and introduce a repair donor containing the Y66H mutation to convert eGFP to eBFP).

Figure 9:
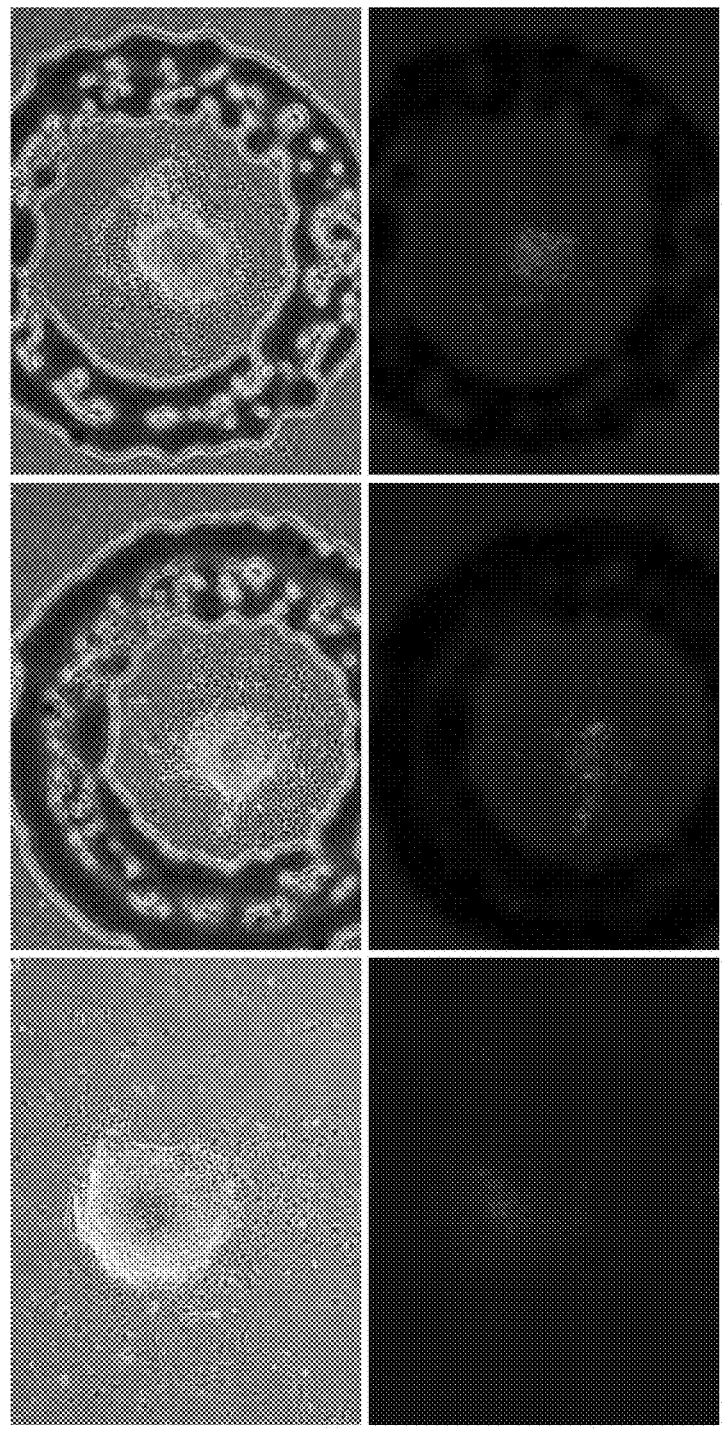
FIG. 9 shows brightfield and fluorescence microscopy (eGFP) images of mouse embryonic stem cells (mESCs) comprising the eBFP CRISPR reporter allele (LSL-eBFP CRISPR reporter allele after treatment with Cre recombinase to generate MAID20090) following treatment with CRISPR/Cas9 and an ssODN repair template to convert eBFP to eGFP. The top row shows brightfield images, and the bottom row shows fluorescence microscopy images (eGFP).

To test the ability of CRISPR/Cas9 to convert eBFP to eGFP via homology-directed repair in the LSL-eBFP CRISPR reporter allele in which the upstream polyadenylation signal has been removed by Cre recombinase (L-eBFP CRISPR reporter allele), embryonic stem cells comprising the reporter allele were electroporated with Cas9 (20 µg) and a guide RNA that targets a target sequence in eBFP (2.5 µg) in the form of a ribonucleoprotein complex and a ssODN (35 µg) designed to convert eBFP to eGFP. The guide RNA target sequence is set forth in SEQ ID NO: 42, and the guide sequence of the guide RNA is set forth in SEQ ID NO: 14. Two ssODNs (F and R, representing "forward" and "reverse" complementary single strands; SEQ ID NOS: 15 and 16, respectively) were used in separate experiments. As shown in FIG. 9, the CRISPR/Cas9 and ssODN F successfully converted eBFP to eGFP, and the eGFP is expressed. The top row in FIG. 9 shows brightfield images, and the bottom row shows fluorescence microscopy images (eGFP).

Similar experiments were performed in hematopoietic stem cells and progenitors cells ex vivo. To test the ability of CRISPR/Cas9 to convert eBFP to eGFP via homology-directed repair in the LSL-eBFP CRISPR reporter allele in which the upstream polyadenylation signal has been removed (L-eBFP CRISPR reporter allele), bone marrow cells were extracted from mice containing the reporter integrated at the Rosa26 locus. Briefly, the femurs and tibias were harvested from the mice, and the bone marrow was extracted. Hematopoietic and progenitor cells (HSPC) were further isolated using the EasySep kit from STEMCELL. The cells were plated in 24-well plates at a density between 250,000 to 1,000,000 cells per well in StemSpan SFEM (STEM cell #09650) media comprising SCF at 100 ng/mL, TPO at 100 ng/mL, Flt3L at 100 ng/mL, IL-6 at 50 ng/mL, and IL-3 at 30 ng/mL. The cells were electroporated with Cas9, a guide RNA that targets a target sequence in eBFP, and an ssODN designed to convert eBFP to eGFP. The guide RNA target sequence is set forth in SEQ ID NO: 42, and the guide sequence of the guide RNA is set forth in SEQ ID NO: 14. The sequences of the ssODNs used are set forth in SEQ ID NOS: 15 and 16.

Figure 10A:
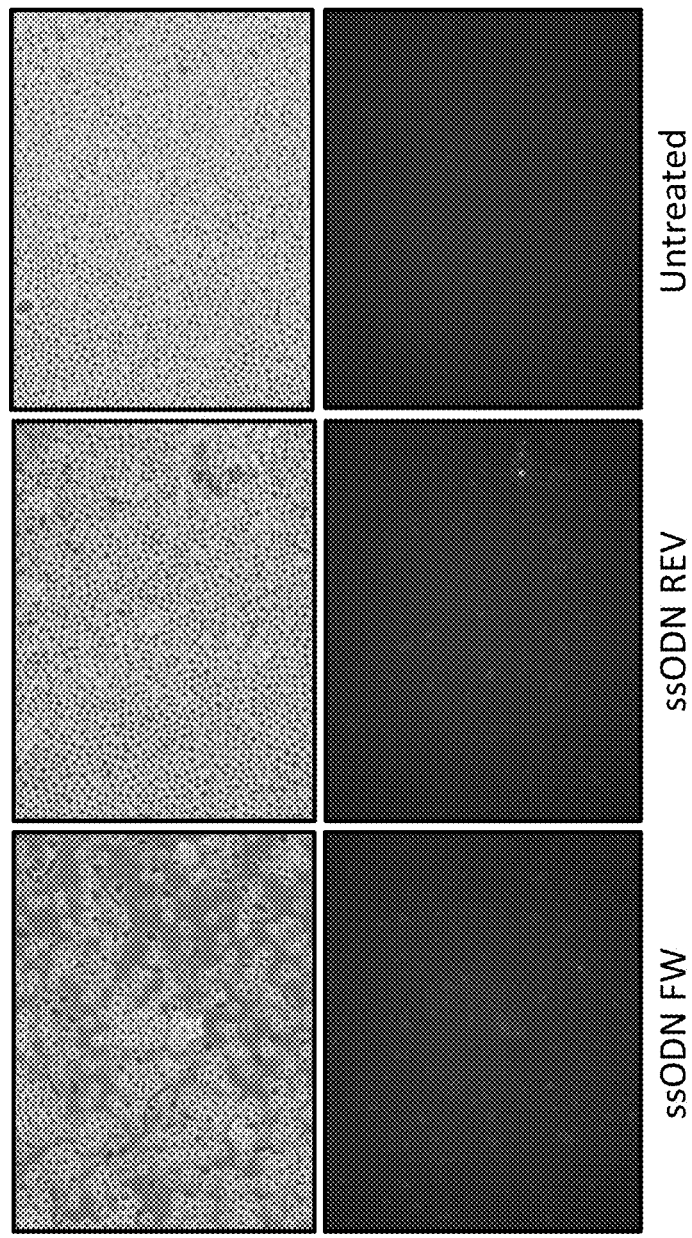
FIG. 10A shows brightfield and fluorescence microscopy (eGFP) images of hematopoietic stem and progenitor cell (HSPC) isolated from mice comprising the eBFP CRISPR reporter allele (LSL-eBFP CRISPR reporter allele after treatment with Cre recombinase to generate MAID20090) genomically integrated at the Rosa26 locus following treatment with CRISPR/Cas9 ribonucleoprotein complexes and an ssODN repair template (FW or REV) via electroporation to convert eBFP to eGFP. The top row shows brightfield images, and the bottom row shows fluorescence microscopy (eGFP) 48 hours after electroporation.
Figure 10B:
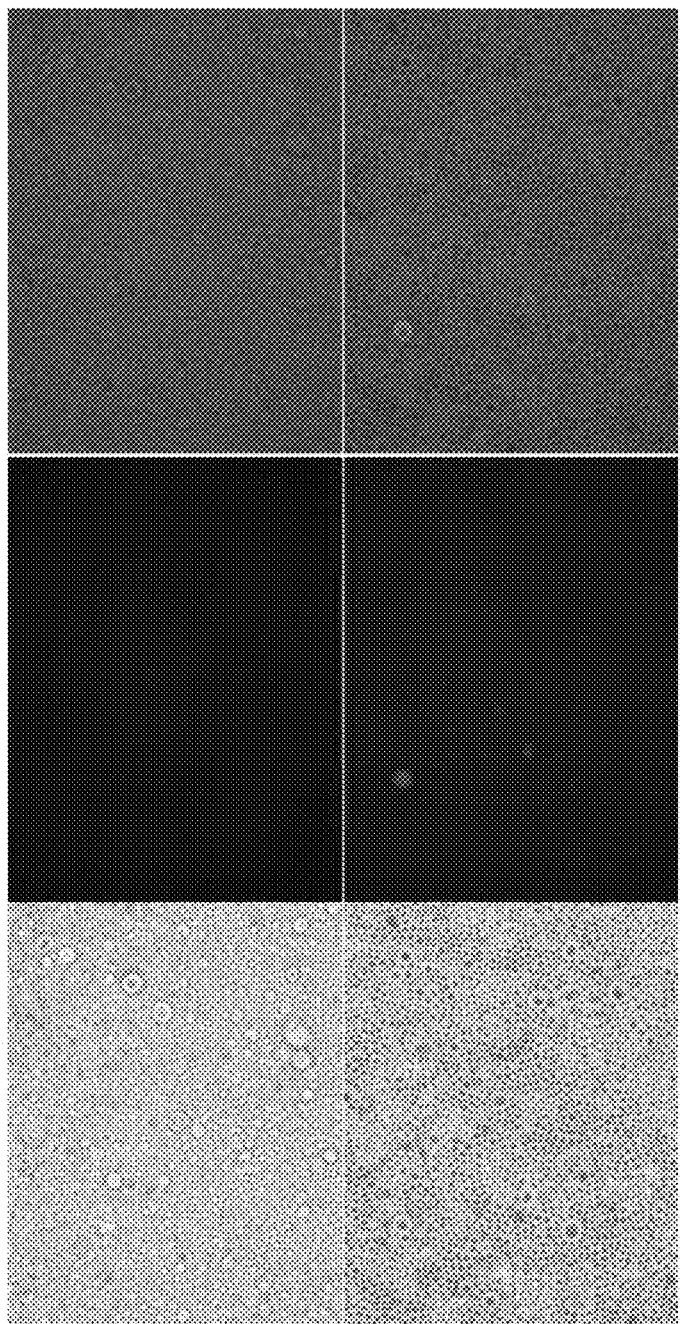
FIG. 10B shows brightfield and fluorescence microscopy (eGFP) images of hematopoietic stem and progenitor cell (HSPC) isolated from mice comprising eBFP CRISPR reporter allele (LSL-eBFP CRISPR reporter allele after treatment with Cre recombinase to generate MAID20090) genomically integrated at the Rosa26 locus following treatment with CRISPR/Cas9 ribonucleoprotein complexes and an ssODN FW repair template via electroporation to convert eBFP to eGFP. The top row shows untreated control cells, and the bottom row shows treated cells. The first column shows brightfield images, and the second and third columns show fluorescence microscopy images (eGFP) 7 days after electroporation.

Specifically, Cas9-sgRNA RNPs were used and were generated by incubating 200 ng to 1 μg of sgRNA with 1 μg Cas9 protein (PNA Bio) for 10-15 minutes at room temperature and then electroporating into 10,000 murine hematopoietic stem and progenitor cells (HSPCs) after 1-3 hours in culture. The optimized electroporation condition for murine HSPCs is 1700V, 20 ms, and 1 pulse using Neon transfection system (Thermo Fisher Scientific). The following EP conditions were tested using 10 nM ssODN+RNP of Cas9+sgRNA: (1) 1720V 10 pulse width, 2 pulse, and cell density: 5e6; (2) 1680V 20 pulse width, 1 pulse, and cell density: 6e7; and (3) 1700V 20 pulse width, 1 pulse, and cell density: 1e8. Brightfield and fluorescence microscopy images 48 hours after electroporation (1720V 10 pulse width, 2 pulse, cell density: 5e6) with Cas9/sgRNA RNP and ssODN FW or Cas9/sgRNA RNP and ssODN REV are shown in FIG. 10A. Untreated cells were used as a negative control. Brightfield images are shown in the top row, and fluorescence microscopy images (eGFP) are shown in the bottom row. Images of the cells 7 days after electroporation are shown in FIG. 10B. The first column shows brightfield images, and the second and third columns show fluorescence microscopy images (eGFP). The fluorescence is especially clear in some larger, differentiated cells. As shown in FIGS. 10A and 10B, the CRISPR/Cas9 and ssODN successfully converted eBFP to eGFP ex vivo in primary cells isolated from the L-eBFP reporter mice, and the eGFP is expressed.

To determine the effectiveness of eGFP as an HDR readout in adult mice in vivo, mESCs targeted with the CRISPR reporter allele shown in FIG. 1A or 3 or Cre-recombinase-treated versions of these alleles were microinjected into 8-cell mouse embryos using the VELOCIMOUSE® method. See, e.g., U.S. Pat. No. 7,576,259; 7,659,442; 7,294,754; US 2008/007800; and Poueymirou et al. (2007) Nature Biotech. 25(1):91-99, each of which is herein incorporated by reference in its entirety for all purposes. Specifically, a small hole was created in the zona pellucida to facilitate the injection of targeted mESC. These injected 8-cell embryos were transferred to surrogate mothers to produce live pups carrying the transgene. Upon gestation in a surrogate mother, the injected embryos produced F0 mice that carried no detectable host embryo contribution. The fully ES cell-derived mice were normal, healthy, and fertile (with germline transmission). The mice can be used to evaluate the feasibility of correcting a mutation in an adult mouse livers using the Cas9 system. To this end, primary hepatocytes are harvested from LSL-eBFP/eGFP targeted mice and are used to assess methods of correcting a point mutation in these non-dividing cells. The most efficient approach can be determined. All materials are then introduced into the mouse via tail vein injection of lipid nanoparticles or adeno-associated virus or by another suitable delivery method. Livers or other tissues of these mice are harvested, and assessment of eGFP expression is performed to look for correctly modified cells. Next-generation sequencing is also performed to look for correctly modified cells. Next-generation sequencing and RNAseq can provide information on the types of cells in the liver or other tissues in which the CRISPR/Cas9 is active.

We claim:

1. A mouse or rat comprising a CRISPR reporter for assessing CRISPR/Cas-induced excision of a nucleic acid between first and second guide RNA target sequences,
 wherein the CRISPR reporter is integrated at a target genomic locus and comprises a first polyadenylation signal flanked by the first and second guide RNA target sequences followed by a reporter cassette comprising a coding sequence for a first reporter protein and a coding sequence for a second reporter protein in any order,
 wherein the first reporter protein and the second reporter protein are different, and
 wherein the mouse or rat expresses the first reporter protein and the second reporter protein when the first polyadenylation signal is excised.

2. The mouse or rat of claim 1, wherein the CRISPR reporter is for assessing CRISPR/Cas-induced recombination of the CRISPR reporter with an exogenous donor nucleic acid.

3. The mouse or rat of claim 2, wherein the first reporter protein comprises a third guide RNA target sequence, wherein recombination of the CRISPR reporter with the exogenous donor nucleic acid changes the coding sequence for the first reporter protein into a coding sequence for a third reporter protein.

4. The mouse or rat of claim 3, wherein the coding sequence for the first reporter protein is changed into the coding sequence for the third reporter protein by changing a single codon.

5. The mouse or rat of claim 3, wherein the third guide RNA target sequence overlaps with the portion of the coding sequence for the first reporter protein modified by the exogenous donor nucleic acid.

6. The mouse or rat of claim 1, wherein one of the first and second reporter proteins comprises a fluorescent reporter protein.

7. The mouse or rat of claim 6, wherein the fluorescent reporter protein comprises an enhanced green fluorescent protein (eGFP) or an enhanced blue fluorescent protein (eBFP).

8. The mouse or rat of claim 6, wherein the first and second reporter proteins comprise the fluorescent reporter protein and a non-fluorescent reporter protein.

9. The mouse or rat of claim 8, wherein the fluorescent reporter protein can be detected in a flow cytometry assay, and the non-fluorescent protein can be detected in a histochemical assay.

10. The mouse or rat of claim 1, wherein one of the first and second reporter proteins comprises a beta-galactosidase protein.

11. The mouse or rat of claim 1, wherein the first polyadenylation signal is also flanked by recombinase recognition sites for a first recombinase.

12. The mouse or rat of claim 11, wherein the recombinase recognition sites for the first recombinase are loxP sequences.

13. The mouse or rat of claim 1, wherein the reporter cassette comprises a multicistronic nucleic acid comprising the coding sequence for the first reporter protein and the coding sequence for the second reporter protein separated by an intervening internal ribosome entry site (IRES) or an intervening 2A peptide coding sequence.

14. The mouse or rat of claim 13, wherein the multicistronic nucleic acid comprises a beta-galactosidase coding sequence and an enhanced blue fluorescent protein (eBFP) coding sequence or an enhanced green fluorescent protein (eGFP) coding sequence separated by an intervening P2A peptide coding sequence.

15. The mouse or rat of claim 1, wherein the CRISPR reporter is operably linked to an endogenous promoter at the target genomic locus.

16. The mouse or rat of claim 1, wherein the 5' end of the CRISPR reporter further comprises a 3' splicing sequence.

17. The mouse or rat of claim 1, wherein the CRISPR reporter further comprises a selection cassette.

18. The mouse or rat of claim 17, wherein the selection cassette is flanked by recombinase recognition sites for a second recombinase.

19. The mouse or rat of claim 17, wherein the selection cassette comprises a drug resistance gene.

20. The mouse or rat of claim 1, wherein the distance between the first guide RNA target sequence and the second guide RNA target sequence is less than 500 base pairs.

21. The mouse or rat of claim 1, wherein the first guide RNA target sequence and the second guide RNA target sequence are identical, and each comprises SEQ ID NO: 41.

22. The mouse or rat of claim 1, wherein the mouse or rat is the rat.

23. The mouse or rat of claim 1, wherein the mouse or rat is the mouse.

24. The mouse or rat of claim 1, wherein the target genomic locus is a safe harbor locus.

25. The mouse or rat of claim 24, wherein the safe harbor locus is a Rosa26 locus.

26. The mouse or rat of claim 25, wherein the CRISPR reporter is inserted into the first intron of the Rosa26 locus.

27. The mouse or rat of claim 1, wherein the mouse or rat is the mouse, and
wherein the target genomic locus is the Rosa26 locus, and
wherein the CRISPR reporter is operably linked to the endogenous Rosa26 promoter, is inserted into the first intron of the Rosa26 locus, and comprises from 5' to 3':
(a) a 3' splicing sequence;
(b) a first polyadenylation signal flanked by:
   (i) first and second loxP sites; and
   (ii) first and second guide RNA target sequences, wherein the first guide RNA target sequence and the second guide RNA target sequence are identical, and each comprises SEQ ID NO: 41; and
(c) a reporter cassette, comprising from 5' to 3':
   (i) a beta-galactosidase coding sequence;
   (ii) a P2A coding sequence;
   (iii) an enhanced blue fluorescent protein (eBFP) coding sequence, wherein the eBFP coding sequence comprises a third guide RNA target sequence comprising SEQ ID NO: 42; and
   (iv) a second polyadenylation signal, wherein the first polyadenylation signal and the second polyadenylation signal are different.

28. The mouse or rat of claim 27, wherein the CRISPR reporter further comprises:
(d) a selection cassette 3' of the reporter cassette, wherein the selection cassette is flanked by FRT sites and comprises from 5' to 3':
   (i) a neomycin phosphotransferase coding sequence operably linked to a human ubiquitin promoter; and
   (ii) a third polyadenylation signal.

29. The mouse or rat of claim 1, wherein the mouse or rat is heterozygous for the CRISPR reporter at the target genomic locus.

30. The mouse or rat of claim 1, wherein the mouse or rat is homozygous for the CRISPR reporter at the target genomic locus.

* * * * *

UNITED STATES PATENT AND TRADEMARK OFFICE
CERTIFICATE OF CORRECTION

| | |
|---|---|
| PATENT NO. | : 11,021,719 B2 |
| APPLICATION NO. | : 16/050806 |
| DATED | : June 1, 2021 |
| INVENTOR(S) | : Guochun Gong et al. |

It is certified that error appears in the above-identified patent and that said Letters Patent is hereby corrected as shown below:

On the Title Page

Item (54) and in the Specification, Column 1, Lines 1-6, Delete "CRISPER/CAS" and insert --CRISPR/CAS--

Signed and Sealed this
Tenth Day of May, 2022

Katherine Kelly Vidal
*Director of the United States Patent and Trademark Office*

SEQUENCE LISTING

```
<160> NUMBER OF SEQ ID NOS: 60

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
gctggactac gtcgtgtgcc                                              20

<210> SEQ ID NO 2
<211> LENGTH: 20
<212> TYPE: RNA
<213> ORGANISM: Artificial Sequence
<220> FEATURE:
<223> OTHER INFORMATION: Synthetic

<400> SEQUENCE: 2
cgaccugaug cagcucucgg                                              20

<210> SEQ ID NO 3
<211> LENGTH: 18
<212> TYPE: PRT
<213> ORGANISM: Artificial Sequence
<220> FEATURE:
<223> OTHER INFORMATION: Synthetic

<400> SEQUENCE: 3

Glu Gly Arg Gly Ser Leu Leu Thr Cys Gly Asp Val Glu Glu Asn Pro
1               5                   10                  15
```

Gly Pro

<210> SEQ ID NO 4
<211> LENGTH: 19
<212> TYPE: PRT
<213> ORGANISM: Artificial Sequence
<220> FEATURE:
<223> OTHER INFORMATION: Synthetic

<400> SEQUENCE: 4

```
Ala Thr Asn Phe Ser Leu Leu Lys Gln Ala Gly Asp Val Glu Glu Asn
1               5                   10                  15

Pro Gly Pro
```

<210> SEQ ID NO 5
<211> LENGTH: 20
<212> TYPE: PRT
<213> ORGANISM: Artificial Sequence
<220> FEATURE:
<223> OTHER INFORMATION: Synthetic

<400> SEQUENCE: 5

```
Gln Cys Thr Asn Tyr Ala Leu Leu Lys Leu Ala Gly Asp Val Glu Ser
1               5                   10                  15

Asn Pro Gly Pro
            20
```

<210> SEQ ID NO 6
<211> LENGTH: 22
<212> TYPE: PRT
<213> ORGANISM: Artificial Sequence
<220> FEATURE:
<223> OTHER INFORMATION: Synthetic

<400> SEQUENCE: 6

```
Val Lys Gln Thr Leu Asn Phe Asp Leu Leu Lys Leu Ala Gly Asp Val
1               5                   10                  15

Glu Ser Asn Pro Gly Pro
            20
```

<210> SEQ ID NO 7
<211> LENGTH: 82
<212> TYPE: RNA
<213> ORGANISM: Artificial Sequence
<220> FEATURE:
<223> OTHER INFORMATION: Synthetic

<400> SEQUENCE: 7

```
guuggaacca uucaaaacag cauagcaagu uaaaauaagg cuaguccguu aucaacuuga    60
aaaaguggca ccgagucggu gc                                            82
```

<210> SEQ ID NO 8
<211> LENGTH: 76
<212> TYPE: RNA
<213> ORGANISM: Artificial Sequence
<220> FEATURE:
<223> OTHER INFORMATION: Synthetic

<400> SEQUENCE: 8

```
guuuuagagc uagaaauagc aaguuaaaau aaggcuaguc cguuaucaac uugaaaaagu    60
ggcaccgagu cggugc                                                   76
```

```
<210> SEQ ID NO 9
<211> LENGTH: 86
<212> TYPE: RNA
<213> ORGANISM: Artificial Sequence
<220> FEATURE:
<223> OTHER INFORMATION: Synthetic

<400> SEQUENCE: 9
guuuaagagc uaugcuggaa acagcauagc aaguuuaaau aaggcuaguc cguuaucaac    60
uugaaaaagu ggcaccgagu cggugc                                         86

<210> SEQ ID NO 10
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: n = A, T, C, or G

<400> SEQUENCE: 10
gnnnnnnnnn nnnnnnnnnn ngg                                            23

<210> SEQ ID NO 11
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(21)
<223> OTHER INFORMATION: n = A, T, C, or G

<400> SEQUENCE: 11
nnnnnnnnnn nnnnnnnnnn ngg                                            23

<210> SEQ ID NO 12
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(23)
<223> OTHER INFORMATION: n = A, T, C, or G

<400> SEQUENCE: 12
ggnnnnnnnn nnnnnnnnnn nnngg                                          25

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
cgacttcgtg acgtgcggta                                                20

<210> SEQ ID NO 14
<211> LENGTH: 20
<212> TYPE: RNA
<213> ORGANISM: Artificial Sequence
<220> FEATURE:
```

<223> OTHER INFORMATION: Synthetic

<400> SEQUENCE: 14
gcugaagcac ugcacgccau                                                    20

<210> SEQ ID NO 15
<211> LENGTH: 123
<212> TYPE: DNA
<213> ORGANISM: Artificial Sequence
<220> FEATURE:
<223> OTHER INFORMATION: Synthetic

<400> SEQUENCE: 15
ttcatctgca ccaccggcaa gctgcccgtg ccctggccca ccctcgtgac caccctgacc        60
tacggcgtgc agtgcttcag ccgctacccc gaccacatga agcagcacga cttcttcaag       120
tcc                                                                     123

<210> SEQ ID NO 16
<211> LENGTH: 123
<212> TYPE: DNA
<213> ORGANISM: Artificial Sequence
<220> FEATURE:
<223> OTHER INFORMATION: Synthetic

<400> SEQUENCE: 16
ggacttgaag aagtcgtgct gcttcatgtg gtcggggtag cggctgaagc actgcacgcc        60
gtaggtcagg gtggtcacga gggtgggcca gggcacgggc agcttgccgg tggtgcagat       120
gaa                                                                     123

<210> SEQ ID NO 17
<211> LENGTH: 7807
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(120)
<223> OTHER INFORMATION: Mouse Upstream Sequence
<220> FEATURE:
<221> NAME/KEY: misc_feature
<222> LOCATION: (215)..(234)
<223> OTHER INFORMATION: Pgk Excision sgRNA v2 Target Site
<220> FEATURE:
<221> NAME/KEY: misc_feature
<222> LOCATION: (243)..(262)
<223> OTHER INFORMATION: Pgk Excision sgRNA v4 Target Site
<220> FEATURE:
<221> NAME/KEY: misc_feature
<222> LOCATION: (248)..(281)
<223> OTHER INFORMATION: LoxP
<220> FEATURE:
<221> NAME/KEY: misc_feature
<222> LOCATION: (263)..(282)
<223> OTHER INFORMATION: Pgk Excision sgRNA v3 Target Site
<220> FEATURE:
<221> NAME/KEY: misc_feature
<222> LOCATION: (305)..(327)
<223> OTHER INFORMATION: Pgk Excision sgRNA v1A Target Site
<220> FEATURE:
<221> NAME/KEY: misc_feature
<222> LOCATION: (336)..(796)
<223> OTHER INFORMATION: Pgk Poly(A)
<220> FEATURE:
<221> NAME/KEY: misc_feature
<222> LOCATION: (337)..(356)
<223> OTHER INFORMATION: Pgk Disruption sgRNA v4 (cGM4) Target Site
<220> FEATURE:
<221> NAME/KEY: misc_feature

```
<222> LOCATION: (371)..(376)
<223> OTHER INFORMATION: Pgk Poly(A) Recognition Motif
<220> FEATURE:
<221> NAME/KEY: misc_feature
<222> LOCATION: (385)..(404)
<223> OTHER INFORMATION: Pgk Disruption sgRNA v5 (cGM5) Target Site
<220> FEATURE:
<221> NAME/KEY: misc_feature
<222> LOCATION: (405)..(424)
<223> OTHER INFORMATION: Pgk Disruption sgRNA v1 (cGM2) Target Site
<220> FEATURE:
<221> NAME/KEY: misc_feature
<222> LOCATION: (452)..(471)
<223> OTHER INFORMATION: Pgk Disruption sgRNA v2 (cGM) Target Site
<220> FEATURE:
<221> NAME/KEY: misc_feature
<222> LOCATION: (571)..(590)
<223> OTHER INFORMATION: Pgk Disruption sgRNA v3 (cGM3) Target Site
<220> FEATURE:
<221> NAME/KEY: misc_feature
<222> LOCATION: (794)..(813)
<223> OTHER INFORMATION: Pgk Excision sgRNA v5 Target Site
<220> FEATURE:
<221> NAME/KEY: misc_feature
<222> LOCATION: (797)..(819)
<223> OTHER INFORMATION: Pgk Excision sgRNA v1B Target Site
<220> FEATURE:
<221> NAME/KEY: misc_feature
<222> LOCATION: (803)..(822)
<223> OTHER INFORMATION: Pgk Excision sgRNA v6 Target Site
<220> FEATURE:
<221> NAME/KEY: misc_feature
<222> LOCATION: (820)..(853)
<223> OTHER INFORMATION: LoxP
<220> FEATURE:
<221> NAME/KEY: misc_feature
<222> LOCATION: (862)..(3930)
<223> OTHER INFORMATION: LacZ
<220> FEATURE:
<221> NAME/KEY: misc_feature
<222> LOCATION: (3931)..(3996)
<223> OTHER INFORMATION: P2A
<220> FEATURE:
<221> NAME/KEY: misc_feature
<222> LOCATION: (3997)..(4713)
<223> OTHER INFORMATION: eBFP
<220> FEATURE:
<221> NAME/KEY: misc_feature
<222> LOCATION: (4193)..(4212)
<223> OTHER INFORMATION: eBFP sgRNA Target Site
<220> FEATURE:
<221> NAME/KEY: misc_feature
<222> LOCATION: (4748)..(4969)
<223> OTHER INFORMATION: SV40 Poly(A)
<220> FEATURE:
<221> NAME/KEY: misc_feature
<222> LOCATION: (4976)..(5023)
<223> OTHER INFORMATION: Frt
<220> FEATURE:
<221> NAME/KEY: misc_feature
<222> LOCATION: (5030)..(6242)
<223> OTHER INFORMATION: Human Ubiquitin C Promoter
<220> FEATURE:
<221> NAME/KEY: misc_feature
<222> LOCATION: (6243)..(6309)
<223> OTHER INFORMATION: EM7 Promoter
<220> FEATURE:
<221> NAME/KEY: misc_feature
<222> LOCATION: (6310)..(7113)
<223> OTHER INFORMATION: Neomycin Phosphotransferase
<220> FEATURE:
<221> NAME/KEY: misc_feature
<222> LOCATION: (7122)..(7598)
<223> OTHER INFORMATION: Pgk Poly(A)
<220> FEATURE:
<221> NAME/KEY: misc_feature
<222> LOCATION: (7609)..(7656)
<223> OTHER INFORMATION: Frt
<220> FEATURE:
```

<221> NAME/KEY: misc_feature
<222> LOCATION: (7663)..(7807)
<223> OTHER INFORMATION: Mouse Downstream Sequence

<400> SEQUENCE: 17

```
ggagtgttgc aataccttc tgggagttct ctgctgcctc ctggcttctg aggaccgccc      60
tgggcctggg agaatccctt cccctcttc cctcgtgatc tgcaactcca gtctttctag     120
ttgaccagct cggcggtgac ctgcacgtct agggcgcagt agtccagggt ttccttgatg    180
atgtcatact tatcctgtcc ctttttttc cacagggcgc gccactagtg gatccggaac    240
ccttaatata acttcgtata atgtatgcta tacgaagtta ttaggtccct cgacctgcag    300
gaatcgacct gatgcagctc tcggagggg gatccgctgt aagtctgcag aaattgatga    360
tctattaaac aataaagatg tccactaaaa tggaagtttt tcctgtcata ctttgttaag    420
aagggtgaga acagagtacc tacattttga atggaaggat tggagctacg ggggtggggg    480
tggggtggga ttagataaat gcctgctctt tactgaaggc tctttactat tgctttatga    540
taatgtttca tagttggata tcataattta acaagcaaa accaaattaa gggccagctc    600
attcctccca ctcatgatct atagatctat agatctctcg tgggatcatt gttttctct    660
tgattcccac tttgtggttc taagtactgt ggtttccaaa tgtgtcagtt tcatagcctg    720
aagaacgaga tcagcagcct ctgttccaca tacacttcat tctcagtatt gttttgccaa    780
gttctaattc catcagcgac ctgatgcagc tctcggagga taacttcgta taatgtatgc    840
tatacgaagt tatccgccac catgggtacc gatttaaatg atccagtggt cctgcagagg    900
agagattggg agaatcccgg tgtgacacag ctgaacagac tagccgccca ccctccttt    960
gcttcttgga gaaacagtga ggaagctagg acagacagac caagccagca actcagatct   1020
ttgaacgggg agtggagatt tgcctggttt ccggcaccag aagcggtgcc ggaaagctgg   1080
ctggagtgcg atcttcctga ggccgatact gtcgtcgtcc cctcaaactg gcagatgcac   1140
ggttacgatg cgcccatcta caccaacgtg acctatccca ttacggtcaa tccgccgttt   1200
gttcccacgg agaatccgac gggttgttac tcgctcacat ttaatgttga tgaaagctgg   1260
ctacaggaag ccagacgcg aattattttt gatggcgtta actcggcgtt tcatctgtgg   1320
tgcaacgggc gctgggtcgg ttacggccag gacagtcgtt tgccgtctga atttgacctg   1380
agcgcatttt tacgcgccgg agaaaaccgc ctcgcggtga tggtgctgcg ctggagtgac   1440
ggcagttatc tggaagatca ggatatgtgg cggatgagcg gcattttccg tgacgtctcg   1500
ttgctgcata aaccgactac acaaatcagc gatttccatg ttgccactcg ctttaatgat   1560
gatttcagcc gcgctgtact ggaggctgaa gttcagatgt gcggcgagtt gcgtgactac   1620
ctacgggtaa cagttctttt atggcagggt gaaacgcagg tcgccagcgg caccgcgcct   1680
ttcggcggtg aaattatcga tgagcgtggt ggttatgccg atcgcgtcac actacgtctg   1740
aacgtcgaaa acccgaaact gtggagcgcc gaaatcccga atctctatcg tgcggtggtt   1800
gaactgcaca ccgccgacgg cacgctgatt gaagcagaag cctgcgatgt cggttttccgc   1860
gaggtgcgga ttgaaaatgg tctgctgctg ctgaacggca agccgttgct gattcgaggc   1920
gttaaccgtc acgagcatca tcctctgcat ggtcaggtca tggatgagca acgatggtg   1980
caggatatcc tgctgatgaa gcagaacaac tttaacgccg tgcgctgttc gcattatccg   2040
aaccatccgc tgtggtacac gctgtgcgac cgctacggcc tgtatgtggt ggatgaagcc   2100
aatattgaaa cccacggcat ggtgccaatg aatcgtctga ccgatgatcc gcgctggcta   2160
ccggcgatga gcgaacgcgt aacgcgaatg gtgcagcgcg atcgtaatca cccgagtgtg   2220
```

```
atcatctggt cgctggggaa tgaatcaggc cacggcgcta atcacgacgc gctgtatcgc   2280
tggatcaaat ctgtcgatcc ttcccgcccg gtgcagtatg aaggcggcgg agccgacacc   2340
acggccaccg atattatttg cccgatgtac gcgcgcgtgg atgaagacca gcccttcccg   2400
gctgtgccga aatggtccat caaaaaatgg ctttcgctac ctggagagac gcgcccgctg   2460
atcctttgcg aatacgccca cgcgatgggt aacagtcttg gcggtttcgc taaatactgg   2520
caggcgtttc gtcagtatcc ccgtttacag ggcggcttcg tctgggactg ggtggatcag   2580
tcgctgatta aatatgatga aaacggcaac ccgtggtcgg cttacggcgg tgattttggc   2640
gatacgccga acgatcgcca gttctgtatg aacggtctgg tctttgccga ccgcacgccg   2700
catccagcgc tgacggaagc aaaacaccag cagcagttttt ccagttccg tttatccggg   2760 caaaccatcg aagtgaccag cgaatacctg ttccgtcata gcgataacga gctcctgcac   2820
tggatggtgg cgctggatgg taagccgctg gcaagcggtg aagtgcctct ggatgtcgct   2880
ccacaaggta acagttgat tgaactgcct gaactaccgc agccggagag cgccgggcaa   2940
ctctggctca cagtacgcgt agtgcaaccg aacgcgaccg catggtcaga agccgggcac   3000
atcagcgcct ggcagcagtg gcgtctggcg gaaaacctca gtgtgacgct ccccgccgcg   3060
tcccacgcca tcccgcatct gaccaccagc gaaatggatt tttgcatcga gctgggtaat   3120
aagcgttggc aatttaaccg ccagtcaggc tttctttcac agatgtggat tggcgataaa   3180
aaacaactgc tgacgccgct gcgcgatcag ttcacccgtg caccgctgga taacgacatt   3240
ggcgtaagtg aagcgacccg cattgaccct aacgcctggg tcgaacgctg gaaggcggcg   3300
ggccattacc aggccgaagc agcgttgttg cagtgcacgg cagatacact tgctgatgcg   3360
gtgctgatta cgaccgctca cgcgtggcag catcagggga aaaccttatt tatcagccgg   3420
aaaacctacc ggattgatgg tagtggtcaa atggcgatta ccgttgatgt tgaagtggcg   3480
agcgatacac cgcatccggc gcggattggc ctgaactgcc agctggcgca ggtagcagag   3540
cgggtaaact ggctcggatt agggccgcaa gaaaactatc ccgaccgcct tactgccgcc   3600
tgttttgacc gctgggatct gccattgtca gacatgtata cccgtacgt cttcccgagc   3660 gaaaacggtc tgcgctgcgg gacgcgcgaa ttgaattatg gcccacacca gtggcgcggc   3720
gacttccagt tcaacatcag ccgctacagt caacagcaac tgatggaaac cagccatcgc   3780
catctgctgc acgcggaaga aggcacatgg ctgaatatcg acggtttcca tatggggatt   3840
ggtggcgacg actcctggag cccgtcagta tcggcggaat tccagctgag cgccggtcgc   3900
taccattacc agttggtctg gtgtcaaaaa ggaagcggag ctactaactt cagcctgctg   3960
aagcaggctg gagacgtgga ggagaaccct ggacctgtga gcaagggcga ggagctgttc   4020
accggggtgg tgcccatcct ggtcgagctg gacggcgacg taaacggcca aagttcagc   4080 gtgtccggcg agggcgaggg cgatgccacc tacggcaagc tgaccctgaa gttcatctgc   4140
accaccggca agctgcccgt gccctggccc accctcgtga ccaccctgac ccatggcgtg   4200
cagtgcttca gccgctaccc cgaccacatg aagcagcacg acttcttcaa gtccgccatg   4260
cccgaaggct acgtccagga gcgcaccatc ttcttcaagg acgacggcaa ctacaagacc   4320
cgcgccgagg tgaagttcga gggcgacacc ctggtgaacc gcatcgagct gaagggcatc   4380
gacttcaagg aggacggcaa catcctgggg cacaagctgg agtacaacta caacagccac   4440
aacgtctata tcatggccga caagcagaag aacggcatca aggtgaactt caagatccgc   4500
cacaacatcg aggacggcag cgtgcagctc gccgaccact accagcagaa cacccccatc   4560
```

```
ggcgacggcc ccgtgctgct gcccgacaac cactacctga gcacccagtc cgccctgagc    4620
aaagacccca acgagaagcg cgatcacatg gtcctgctgg agttcgtgac cgccgccggg    4680
atcactctcg gcatggacga gctgtacaag taataattct agagtcgggg cggccggccg    4740
cttcgagcag acatgataag atacattgat gagtttggac aaaccacaac tagaatgcag    4800
tgaaaaaaat gctttatttg tgaaatttgt gatgctattg ctttatttgt aaccattata    4860
agctgcaata acaagttaa caacaacaat tgcattcatt ttatgtttca ggttcagggg    4920
gaggtgtggg aggttttttta aagcaagtaa aacctctaca aatgtggtac tcgaggaagt    4980
tcctattccg aagttcctat tctctagaaa gtataggaac ttcatgcatg gcctccgcgc    5040
cgggttttgg cgcctcccgc gggcgccccc ctcctcacgg cgagcgctgc cacgtcagac    5100
gaagggcgca gcgagcgtcc tgatccttcc gcccggacgc tcaggacagc ggcccgctgc    5160
tcataagact cggccttaga accccagtat cagcagaagg acattttagg acgggacttg    5220
ggtgactcta gggcactggt tttctttcca gagagcggaa caggcgagga aaagtagtcc    5280
cttctcggcg attctgcgga gggatctccg tggggcggtg aacgccgatg attatataag    5340
gacgcgccgg gtgtggcaca gctagttccg tcgcagccgg gatttgggtc gcggttcttg    5400
tttgtggatc gctgtgatcg tcacttggtg agtagcgggc tgctgggctg gccggggctt    5460
tcgtggccgc cgggccgctc ggtgggacgg aagcgtgtgg agagaccgcc aagggctgta    5520
gtctgggtcc gcgagcaagg ttgccctgaa ctggggggttg gggggagcgc agcaaaatgg    5580
cggctgttcc cgagtcttga atggaagacg cttgtgaggc gggctgtgag gtcgttgaaa    5640
caaggtgggg ggcatggtgg gcggcaagaa cccaaggtct tgaggccttc gctaatgcgg    5700
gaaagctctt attcgggtga gatgggctgg ggcaccatct ggggaccctg acgtgaagtt    5760
tgtcactgac tggagaactc ggtttgtcgt ctgttgcggg ggcggcagtt atggcggtgc    5820
cgttgggcag tgcacccgta cctttgggag gcgcgcgccct cgtcgtgtcg tgacgtcacc    5880
cgttctgttg gcttataatg cagggtgggg ccacctgccg gtaggtgtgc ggtaggcttt    5940
tctccgtcgc aggacgcagg gttcgggcct agggtaggct ctcctgaatc gacaggcgcc    6000
ggacctctgg tgaggggagg gataagtgag gcgtcagttt cttggtcgg ttttatgtac    6060 ctatcttctt aagtagctga agctccggtt ttgaactatg cgctcggggt tggcgagtgt    6120
gttttgtgaa gttttttagg cacctttga aatgtaatca tttgggtcaa tatgtaatt    6180 tcagtgttag actagtaaat tgtccgctaa attctggccg ttttttggctt ttttgttaga    6240 cgtgttgaca attaatcatc ggcatagtat atcggcatag tataatacga caaggtgagg    6300
aactaaacca tgggatcggc cattgaacaa gatggattgc acgcaggttc tccggccgct    6360
tgggtggaga ggctattcgg ctatgactgg gcacaacaga caatcggctg ctctgatgcc    6420
gccgtgttcc ggctgtcagc gcaggggcgc ccggttcttt ttgtcaagac cgacctgtcc    6480
ggtgccctga tgaactgca ggacgaggca gcgcggctat cgtggctggc cacgacgggc    6540
gttccttgcg cagctgtgct cgacgttgtc actgaagcgg gaagggactg gctgctattg    6600
ggcgaagtgc cggggcagga tctcctgtca tctcaccttg ctcctgccga gaaagtatcc    6660
atcatggctg atgcaatgcg gcggctgcat acgcttgatc cggctacctg cccattcgac    6720
caccaagcga aacatcgcat cgagcgagca cgtactcgga tggaagccgg tcttgtcgat    6780
caggatgatc tggacgaaga gcatcagggg ctcgcgccag ccgaactgtt cgccaggctc    6840
aaggcgcgca tgcccgacgg cgatgatctc gtcgtgaccc atggcgatgc ctgcttgccg    6900
aatatcatgg tggaaaatgg ccgcttttct ggattcatcg actgtggccg gctgggtgtg    6960
```

```
gcggaccgct atcaggacat agcgttggct acccgtgata ttgctgaaga gcttggcggc    7020
gaatgggctg accgcttcct cgtgctttac ggtatcgccg ctcccgattc gcagcgcatc    7080
gccttctatc gccttcttga cgagttcttc tgaggggatc cgctgtaagt ctgcagaaat    7140
tgatgatcta ttaaacaata aagatgtcca ctaaaatgga agttttcct gtcatacttt     7200 gttaagaagg gtgagaacag agtacctaca ttttgaatgg aaggattgga gctacggggg    7260
tgggggtggg gtgggattag ataaatgcct gctctttact gaaggctctt tactattgct    7320
ttatgataat gtttcatagt tggatatcat aatttaaaca agcaaaacca aattaagggc    7380
cagctcattc ctcccactca tgatctatag atctatagat ctctcgtggg atcattgttt    7440
ttctcttgat tcccactttg tggttctaag tactgtggtt tccaaatgtg tcagtttcat    7500
agcctgaaga acgagatcag cagcctctgt tccacataca cttcattctc agtattgttt    7560
tgccaagttc taattccatc agacctcgac ctgcagcccc tagtcgacga agttcctatt    7620
ccgaagttcc tattctctag aaagtatagg aacttcgcta gctaaaattg gagggacaag    7680
acttcccaca gattttcggt tttgtcggga agtttttaa taggggcaaa taaggaaaat     7740
gggaggatag gtagtcatct ggggttttat gcagcaaaac tacaggttat tattgcttgt    7800
gatccgc                                                             7807

<210> SEQ ID NO 18
<211> LENGTH: 3716
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(172)
<223> OTHER INFORMATION: Mouse Upstream Sequence
<220> FEATURE:
<221> NAME/KEY: misc_feature
<222> LOCATION: (226)..(259)
<223> OTHER INFORMATION: LoxP
<220> FEATURE:
<221> NAME/KEY: misc_feature
<222> LOCATION: (357)..(423)
<223> OTHER INFORMATION: EM7 Promoter
<220> FEATURE:
<221> NAME/KEY: misc_feature
<222> LOCATION: (424)..(1227)
<223> OTHER INFORMATION: Neomycin Phosphotransferase
<220> FEATURE:
<221> NAME/KEY: misc_feature
<222> LOCATION: (1236)..(2489)
<223> OTHER INFORMATION: Triple Poly(A)
<220> FEATURE:
<221> NAME/KEY: misc_feature
<222> LOCATION: (2517)..(2550)
<223> OTHER INFORMATION: LoxP
<220> FEATURE:
<221> NAME/KEY: misc_feature
<222> LOCATION: (2596)..(3315)
<223> OTHER INFORMATION: eBFP
<220> FEATURE:
<221> NAME/KEY: misc_feature
<222> LOCATION: (2795)..(2814)
<223> OTHER INFORMATION: eBFP sgRNA Target Site
<220> FEATURE:
<221> NAME/KEY: misc_feature
<222> LOCATION: (3350)..(3571)
<223> OTHER INFORMATION: SV40 Poly(A)
<220> FEATURE:
<221> NAME/KEY: misc_feature
<222> LOCATION: (3572)..(3716)
<223> OTHER INFORMATION: Mouse Downstream Sequence
```

<400> SEQUENCE: 18

```
ctgcagtgga gtaggcgggg agaaggccgc acccttctcc ggaggggga ggggagtgtt      60
gcaataccttt tctgggagtt ctctgctgcc tcctggcttc tgaggaccgc cctgggcctg    120
ggagaatccc ttccccctct tccctcgtga tctgcaactc cagtcttcct agttgaccag    180
ctcggcggtg acctgcacgt ctagggcgca gtagtccagg gtttccttga tgatgtcata    240
cttatcctgt ccctttttt tccacagggc gcgccactag tggatccgga acccttaata    300
taacttcgta taatgtatgc tatacgaagt tattaggtcc ctcgacctgc aggaattgtt    360
gacaattaat catcggcata gtatatcggc atagtataat acgacaaggt gaggaactaa    420
accatgggat cggccattga acaagatgga ttgcacgcag gttctccggc cgcttgggtg    480
gagaggctat tcggctatga ctgggcacaa cagacaatcg gctgctctga tgccgccgtg    540
ttccggctgt cagcgcaggg gcgcccggtt cttttttgtca agaccgacct gtccggtgcc    600
ctgaatgaac tgcaggacga ggcagcgcgg ctatcgtggc tggccacgac gggcgttcct    660
tgcgcagctg tgctcgacgt tgtcactgaa gcgggaaggg actggctgct attgggcgaa    720
gtgccggggc aggatctcct gtcatctcac cttgctcctg ccgagaaagt atccatcatg    780
gctgatgcaa tgcggcggct gcatacgctt gatccggcta cctgcccatt cgaccaccaa    840
gcgaaacatc gcatcgagcg agcacgtact cggatggaag ccggtcttgt cgatcaggat    900
gatctggacg aagagcatca ggggctcgcg ccagccgaac tgttcgccag gctcaaggcg    960
cgcatgcccg acggcgatga tctcgtcgtg acccatggcg atgcctgctt gccgaatatc   1020
atggtggaaa atggccgctt ttctggattc atcgactgtg gccggctggg tgtggcggac   1080
cgctatcagg acatagcgtt ggctacccgt gatattgctg aagagcttgg cggcgaatgg   1140
gctgaccgct tcctcgtgct ttacggtatc gccgctcccg attcgcagcg catcgccttc   1200
tatcgccttc ttgacgagtt cttctgaggg gatccgctgt aagtctgcag aaattgatga   1260
tctattaaac aataaagatg tccactaaaa tggaagtttt tcctgtcata ctttgttaag   1320
aagggtgaga acagagtacc tacattttga atggaaggat tggagctacg ggggtggggg   1380
tggggtggga ttagataaat gcctgctctt tactgaaggc tctttactat tgctttatga   1440
taatgtttca tagttggata tcataattta acaagcaaa accaaattaa gggccagctc   1500
attcctccca ctcatgatct atagatctat agatctctcg tgggatcatt gttttttctct   1560
tgattcccac tttgtggttc taagtactgt ggtttccaaa tgtgtcagtt tcatagcctg   1620
aagaacgaga tcagcagcct ctgttccaca tacacttcat tctcagtatt gttttgccaa   1680
gttctaattc catcagaagc ttgcagatct gcgactctag aggatctgcg actctagagg   1740
atcataatca gccataccac atttgtagag gttttacttg ctttaaaaaa cctcccacac   1800
ctcccctga acctgaaaca taaatgaat gcaattgttg ttgttaactt gtttattgca   1860
gcttataatg gttacaaata aagcaatagc atcacaaatt tcacaaataa agcattttt   1920
tcactgcatt ctagttgtgg tttgtccaaa ctcatcaatg tatcttatca tgtctggatc   1980
tgcgactcta gaggatcata atcagccata ccacatttgt agaggtttta cttgctttaa   2040
aaaacctccc cacacctccc ctgaacctga aacataaaat gaatgcaatt gttgttgtta   2100
acttgtttat tgcagcttat aatggttaca ataaagcaa tagcatcaca aatttcacaa   2160
ataaagcatt ttttcactg cattctagtt gtggtttgtc caaactcatc aatgtatctt   2220
atcatgtctg gatctgcgac tctagaggat cataatcagc cataccacat tgtagaggt   2280
tttacttgct ttaaaaaaacc tcccacacct ccccctgaac ctgaaacata aatgaatgc   2340
```

```
aattgttgtt gttaacttgt ttattgcagc ttataatggt tacaaataaa gcaatagcat    2400
cacaaatttc acaaataaag cattttttc actgcattct agttgtggtt tgtccaaact     2460
catcaatgta tcttatcatg tctggatccc catcaagctg atccggaacc cttaatataa    2520
cttcgtataa tgtatgctat acgaagttat taggtccctc gacctgcagc ccaagctagt    2580
gcccgggccg ccaccatggt gagcaagggc gaggagctgt tcaccggggt ggtgcccatc    2640
ctggttgagc tggacggcga cgtaaacggc cacaagttca gcgtgtccgg cgagggcgag    2700
ggcgatgcca cctacggcaa gctgaccctg aagttcatct gcaccaccgg caagctgccc    2760 gtgcccggc ccaccctcgt gaccaccctg acccatggcg tgcagtgctt cagccgctac     2820
cccgaccaca tgaagcagca cgacttcttc aagtccgcca tgcccgaagg ctacgtccag    2880
gagcgcacca tcttcttcaa ggacgacggc aactacaaga cccgcgccga ggtgaagttc    2940
gagggcgaca ccctggtgaa ccgcatcgag ctgaagggca tcgacttcaa ggaggacggc    3000
aacatcctgg ggcacaagct ggagtacaac tacaacagcc acaacgtcta tatcatggcc    3060
gacaagcaga agaacggcat caaggtgaac ttcaagatcc gccacaacat cgaggacggc    3120
agcgtgcagc tcgccgacca ctaccagcag aacacccca tcggcgacgg ccccgtgctg     3180
ctgcccgaca accactacct gagcacccag tccgccctga gcaaagaccc caacgagaag    3240
cgcgatcaca tggtcctgct ggagttcgtg accgccgccg ggatcactct cggcatggac    3300
gagctgtaca agtaataatt ctagagtcgg ggcggccggc cgcttcgagc agacatgata    3360
agatacattg atgagtttgg acaaaccaca actagaatgc agtgaaaaaa atgctttatt    3420
tgtgaaattt gtgatgctat tgctttattt gtaaccatta taagctgcaa taaacaagtt    3480
aacaacaaca attgcattca ttttatgttt caggttcagg gggaggtgtg ggaggttttt    3540
taaagcaagt aaaacctcta caaatgtggt actcgagtaa aattggaggg acaagacttc    3600
ccacagattt tcggttttgt cgggaagttt tttaataggg gcaaataagg aaaatgggag    3660
gataggtagt catctggggt tttatgcagc aaaaactacag gttattattg cttgtg       3716
```

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
cccgcgcggt gatcacctag    20

<210> SEQ ID NO 20
<211> LENGTH: 20
<212> TYPE: RNA
<213> ORGANISM: Artificial Sequence
<220> FEATURE:
<223> OTHER INFORMATION: Synthetic

<400> SEQUENCE: 20
gggcgcgcca cuaguggauc    20

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
catacgatat gcttcaataa                                               20

<210> SEQ ID NO 22
<211> LENGTH: 20
<212> TYPE: RNA
<213> ORGANISM: Artificial Sequence
<220> FEATURE:
<223> OTHER INFORMATION: Synthetic

<400> SEQUENCE: 22
guaugcuaua cgaaguuauu                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
taatatgctt caatataatt                                               20

<210> SEQ ID NO 24
<211> LENGTH: 20
<212> TYPE: RNA
<213> ORGANISM: Artificial Sequence
<220> FEATURE:
<223> OTHER INFORMATION: Synthetic

<400> SEQUENCE: 24
auuauacgaa guuauauuaa                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
gtcgctggac tacgtcgaga                                               20

<210> SEQ ID NO 26
<211> LENGTH: 20
<212> TYPE: RNA
<213> ORGANISM: Artificial Sequence
<220> FEATURE:
<223> OTHER INFORMATION: Synthetic

<400> SEQUENCE: 26
cagcgaccug augcagcucu                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
ataggaggct ctcgacgtag                                               20

<210> SEQ ID NO 28
<211> LENGTH: 20

```
<212> TYPE: RNA
<213> ORGANISM: Artificial Sequence
<220> FEATURE:
<223> OTHER INFORMATION: Synthetic

<400> SEQUENCE: 28
uauccuccga gagcugcauc                                               20

<210> SEQ ID NO 29
<211> LENGTH: 20
<212> TYPE: RNA
<213> ORGANISM: Artificial Sequence
<220> FEATURE:
<223> OTHER INFORMATION: Synthetic

<400> SEQUENCE: 29
ccuucuuaac aaaguaugac                                               20

<210> SEQ ID NO 30
<211> LENGTH: 20
<212> TYPE: RNA
<213> ORGANISM: Artificial Sequence
<220> FEATURE:
<223> OTHER INFORMATION: Synthetic

<400> SEQUENCE: 30
uggaaggauu ggagcuacgg                                               20

<210> SEQ ID NO 31
<211> LENGTH: 20
<212> TYPE: RNA
<213> ORGANISM: Artificial Sequence
<220> FEATURE:
<223> OTHER INFORMATION: Synthetic

<400> SEQUENCE: 31
aacaagcaaa accaaauuaa                                               20

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
ggaagaattg tttcatactg                                               20

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
accttcctaa cctcgatgcc                                               20

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
```

```
ttgttcgttt tggtttaatt                                              20

<210> SEQ ID NO 35
<211> LENGTH: 20
<212> TYPE: RNA
<213> ORGANISM: Artificial Sequence
<220> FEATURE:
<223> OTHER INFORMATION: Synthetic

<400> SEQUENCE: 35
caauuucugc agacuuacag                                              20

<210> SEQ ID NO 36
<211> LENGTH: 20
<212> TYPE: RNA
<213> ORGANISM: Artificial Sequence
<220> FEATURE:
<223> OTHER INFORMATION: Synthetic

<400> SEQUENCE: 36
aggaaaaacu uccauuuuag                                              20

<210> SEQ ID NO 37
<211> LENGTH: 16
<212> TYPE: RNA
<213> ORGANISM: Artificial Sequence
<220> FEATURE:
<223> OTHER INFORMATION: Synthetic

<400> SEQUENCE: 37
guuuuagagc uaugcu                                                  16

<210> SEQ ID NO 38
<211> LENGTH: 67
<212> TYPE: RNA
<213> ORGANISM: Artificial Sequence
<220> FEATURE:
<223> OTHER INFORMATION: Synthetic

<400> SEQUENCE: 38
agcauagcaa guuaaaauaa ggcuaguccg uuaucaacuu gaaaaagugg caccgagucg   60
gugcuuu                                                            67

<210> SEQ ID NO 39
<211> LENGTH: 77
<212> TYPE: RNA
<213> ORGANISM: Artificial Sequence
<220> FEATURE:
<223> OTHER INFORMATION: Synthetic

<400> SEQUENCE: 39
guuuuagagc uagaaauagc aaguuaaaau aaggcuaguc cguuaucaac uugaaaaagu   60
ggcaccgagu cggugcu                                                 77

<210> SEQ ID NO 40
<211> LENGTH: 1053
<212> TYPE: RNA
<213> ORGANISM: Artificial Sequence
<220> FEATURE:
<223> OTHER INFORMATION: Synthetic

<400> SEQUENCE: 40
augcccaaga agaagaggaa gguguccaau uuacugaccg uacaccaaaa uuugccugca   60
uuaccggucg augcaacgag ugaugagguu cgcaagaacc ugauggacau guucaggggau  120
```

```
cgccaggcgu uuucugagca uaccuggaaa augcuucugu ccguuugccg gucgugggcg    180
gcauggugca aguugaauaa ccggaaaugg uuucccgcag aaccugaaga uguucgcgau    240
uaucuucuau aucuucaggc gcgcggucug gcaguaaaaa cuauccagca acauuuggc     300 cagcuaaaca ugcuucaucg ucgguccggg cugccacgac caagugacag caaugcuguu    360
ucacugguua ugcggcggau ccgaaaagaa aacguugaug ccggugaacg ugcaaaacag    420
gcucuagcgu ucgaacgcac ugauuucgac cagguucguu cacucaugga aaauagcgau    480
cgcugccagg auauacguaa ucuggcauuu cuggggauug cuuauaacac ccguuacgu     540 auagccgaaa uugccaggau cagguuaaa gauaucucac guacgacgg ugggagaaug      600 uuaauccaua uuggcagaac gaaaacgcug guuagcaccg caggguuaga aaggcacuu     660 agccuggggg uaacuaaacu ggucgagcga uggauuuccg ucucuggugu agcugaugau    720
ccgaauaacu accuguuuug ccgggucaga aaaaauggug uugccgcgcc aucugccacc    780
agccagcuau caacucgcgc ccuggaaggg auuuuugaag caacucaucg auugauuuac    840
ggcgcuaagg augacucugg ucagagauac cuggccuggu cuggacacag ugcccguguc    900
ggagccgcgc gagauauggc ccgcgcugga guuucaauac cggagaucau gcaagcuggu    960
ggcuggacca auguaaauau ugucaugaac uauauccgua accuggauag ugaaacaggg   1020 gcaaugguc gccugcugga agauggcgau uag                                 1053
```

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
cgacctgatg cagctctcgg                                                20

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
gctgaagcac tgcacgccat                                                20

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
gggcgcgcca ctagtggatc                                                20

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44

```
gtatgctata cgaagttatt                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45
attatacgaa gttatattaa                                              20

<210> SEQ ID NO 46
<211> LENGTH: 20
<212> TYPE: DNA
<213> ORGANISM: Artificial Sequence
<220> FEATURE:
<223> OTHER INFORMATION: Synthetic

<400> SEQUENCE: 46
cagcgacctg atgcagctct                                              20

<210> SEQ ID NO 47
<211> LENGTH: 20
<212> TYPE: DNA
<213> ORGANISM: Artificial Sequence
<220> FEATURE:
<223> OTHER INFORMATION: Synthetic

<400> SEQUENCE: 47
tatcctccga gagctgcatc                                              20

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
ccttcttaac aaagtatgac                                              20

<210> SEQ ID NO 49
<211> LENGTH: 20
<212> TYPE: DNA
<213> ORGANISM: Artificial Sequence
<220> FEATURE:
<223> OTHER INFORMATION: Synthetic

<400> SEQUENCE: 49
tggaaggatt ggagctacgg                                              20

<210> SEQ ID NO 50
<211> LENGTH: 20
<212> TYPE: DNA
<213> ORGANISM: Artificial Sequence
<220> FEATURE:
<223> OTHER INFORMATION: Synthetic

<400> SEQUENCE: 50
aacaagcaaa accaaattaa                                              20

<210> SEQ ID NO 51
<211> LENGTH: 20
<212> TYPE: DNA
<213> ORGANISM: Artificial Sequence
```

```
<220> FEATURE:
<223> OTHER INFORMATION: Synthetic

<400> SEQUENCE: 51
caatttctgc agacttacag                                              20

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
aggaaaaact tccattttag                                              20

<210> SEQ ID NO 53
<211> LENGTH: 1391
<212> TYPE: PRT
<213> ORGANISM: Artificial Sequence
<220> FEATURE:
<223> OTHER INFORMATION: Synthetic

<400> SEQUENCE: 53
```

Met Asp Lys Pro Lys Lys Arg Lys Val Lys Tyr Ser Ile Gly Leu
1               5                   10                  15

Asp Ile Gly Thr Asn Ser Val Gly Trp Ala Val Ile Thr Asp Glu Tyr
            20                  25                  30

Lys Val Pro Ser Lys Lys Phe Lys Val Leu Gly Asn Thr Asp Arg His
        35                  40                  45

Ser Ile Lys Lys Asn Leu Ile Gly Ala Leu Leu Phe Asp Ser Gly Glu
    50                  55                  60

Thr Ala Glu Ala Thr Arg Leu Lys Arg Thr Ala Arg Arg Arg Tyr Thr
65                  70                  75                  80

Arg Arg Lys Asn Arg Ile Cys Tyr Leu Gln Glu Ile Phe Ser Asn Glu
                85                  90                  95

Met Ala Lys Val Asp Asp Ser Phe Phe His Arg Leu Glu Glu Ser Phe
            100                 105                 110

Leu Val Glu Glu Asp Lys Lys His Glu Arg His Pro Ile Phe Gly Asn
        115                 120                 125

Ile Val Asp Glu Val Ala Tyr His Glu Lys Tyr Pro Thr Ile Tyr His
    130                 135                 140

Leu Arg Lys Lys Leu Val Asp Ser Thr Asp Lys Ala Asp Leu Arg Leu
145                 150                 155                 160

Ile Tyr Leu Ala Leu Ala His Met Ile Lys Phe Arg Gly His Phe Leu
                165                 170                 175

Ile Glu Gly Asp Leu Asn Pro Asp Asn Ser Asp Val Asp Lys Leu Phe
            180                 185                 190

Ile Gln Leu Val Gln Thr Tyr Asn Gln Leu Phe Glu Glu Asn Pro Ile
        195                 200                 205

Asn Ala Ser Gly Val Asp Ala Lys Ala Ile Leu Ser Ala Arg Leu Ser
    210                 215                 220

Lys Ser Arg Arg Leu Glu Asn Leu Ile Ala Gln Leu Pro Gly Glu Lys
225                 230                 235                 240

Lys Asn Gly Leu Phe Gly Asn Leu Ile Ala Leu Ser Leu Gly Leu Thr
                245                 250                 255

Pro Asn Phe Lys Ser Asn Phe Asp Leu Ala Glu Asp Ala Lys Leu Gln
            260                 265                 270

```
Leu Ser Lys Asp Thr Tyr Asp Asp Leu Asp Asn Leu Leu Ala Gln
        275                 280                 285

Ile Gly Asp Gln Tyr Ala Asp Leu Phe Leu Ala Ala Lys Asn Leu Ser
290                 295                 300

Asp Ala Ile Leu Leu Ser Asp Ile Leu Arg Val Asn Thr Glu Ile Thr
305                 310                 315                 320

Lys Ala Pro Leu Ser Ala Ser Met Ile Lys Arg Tyr Asp Glu His His
                325                 330                 335

Gln Asp Leu Thr Leu Leu Lys Ala Leu Val Arg Gln Gln Leu Pro Glu
                340                 345                 350

Lys Tyr Lys Glu Ile Phe Phe Asp Gln Ser Lys Asn Gly Tyr Ala Gly
        355                 360                 365

Tyr Ile Asp Gly Gly Ala Ser Gln Glu Glu Phe Tyr Lys Phe Ile Lys
370                 375                 380

Pro Ile Leu Glu Lys Met Asp Gly Thr Glu Glu Leu Leu Val Lys Leu
385                 390                 395                 400

Asn Arg Glu Asp Leu Leu Arg Lys Gln Arg Thr Phe Asp Asn Gly Ser
                405                 410                 415

Ile Pro His Gln Ile His Leu Gly Glu Leu His Ala Ile Leu Arg Arg
        420                 425                 430

Gln Glu Asp Phe Tyr Pro Phe Leu Lys Asp Asn Arg Glu Lys Ile Glu
                435                 440                 445

Lys Ile Leu Thr Phe Arg Ile Pro Tyr Tyr Val Gly Pro Leu Ala Arg
        450                 455                 460

Gly Asn Ser Arg Phe Ala Trp Met Thr Arg Lys Ser Glu Glu Thr Ile
465                 470                 475                 480

Thr Pro Trp Asn Phe Glu Glu Val Val Asp Lys Gly Ala Ser Ala Gln
                485                 490                 495

Ser Phe Ile Glu Arg Met Thr Asn Phe Asp Lys Asn Leu Pro Asn Glu
                500                 505                 510

Lys Val Leu Pro Lys His Ser Leu Leu Tyr Glu Tyr Phe Thr Val Tyr
        515                 520                 525

Asn Glu Leu Thr Lys Val Lys Tyr Val Thr Glu Gly Met Arg Lys Pro
        530                 535                 540

Ala Phe Leu Ser Gly Glu Gln Lys Lys Ala Ile Val Asp Leu Leu Phe
545                 550                 555                 560

Lys Thr Asn Arg Lys Val Thr Val Lys Gln Leu Lys Glu Asp Tyr Phe
                565                 570                 575

Lys Lys Ile Glu Cys Phe Asp Ser Val Glu Ile Ser Gly Val Glu Asp
                580                 585                 590

Arg Phe Asn Ala Ser Leu Gly Thr Tyr His Asp Leu Leu Lys Ile Ile
                595                 600                 605

Lys Asp Lys Asp Phe Leu Asp Asn Glu Glu Asn Glu Asp Ile Leu Glu
        610                 615                 620

Asp Ile Val Leu Thr Leu Thr Leu Phe Glu Asp Arg Glu Met Ile Glu
625                 630                 635                 640

Glu Arg Leu Lys Thr Tyr Ala His Leu Phe Asp Asp Lys Val Met Lys
                645                 650                 655

Gln Leu Lys Arg Arg Arg Tyr Thr Gly Trp Gly Arg Leu Ser Arg Lys
                660                 665                 670

Leu Ile Asn Gly Ile Arg Asp Lys Gln Ser Gly Lys Thr Ile Leu Asp
        675                 680                 685
```

```
Phe Leu Lys Ser Asp Gly Phe Ala Asn Arg Asn Phe Met Gln Leu Ile
    690                 695                 700

His Asp Asp Ser Leu Thr Phe Lys Glu Asp Ile Gln Lys Ala Gln Val
705                 710                 715                 720

Ser Gly Gln Gly Asp Ser Leu His Glu His Ile Ala Asn Leu Ala Gly
                725                 730                 735

Ser Pro Ala Ile Lys Lys Gly Ile Leu Gln Thr Val Lys Val Val Asp
                740                 745                 750

Glu Leu Val Lys Val Met Gly Arg His Lys Pro Glu Asn Ile Val Ile
                755                 760                 765

Glu Met Ala Arg Glu Asn Gln Thr Thr Gln Lys Gly Gln Lys Asn Ser
770                 775                 780

Arg Glu Arg Met Lys Arg Ile Glu Glu Gly Ile Lys Glu Leu Gly Ser
785                 790                 795                 800

Gln Ile Leu Lys Glu His Pro Val Glu Asn Thr Gln Leu Gln Asn Glu
                805                 810                 815

Lys Leu Tyr Leu Tyr Tyr Leu Gln Asn Gly Arg Asp Met Tyr Val Asp
                820                 825                 830

Gln Glu Leu Asp Ile Asn Arg Leu Ser Asp Tyr Asp Val Asp His Ile
                835                 840                 845

Val Pro Gln Ser Phe Leu Lys Asp Asp Ser Ile Asp Asn Lys Val Leu
850                 855                 860

Thr Arg Ser Asp Lys Asn Arg Gly Lys Ser Asp Asn Val Pro Ser Glu
865                 870                 875                 880

Glu Val Val Lys Lys Met Lys Asn Tyr Trp Arg Gln Leu Leu Asn Ala
                885                 890                 895

Lys Leu Ile Thr Gln Arg Lys Phe Asp Asn Leu Thr Lys Ala Glu Arg
                900                 905                 910

Gly Gly Leu Ser Glu Leu Asp Lys Ala Gly Phe Ile Lys Arg Gln Leu
                915                 920                 925

Val Glu Thr Arg Gln Ile Thr Lys His Val Ala Gln Ile Leu Asp Ser
                930                 935                 940

Arg Met Asn Thr Lys Tyr Asp Glu Asn Asp Lys Leu Ile Arg Glu Val
945                 950                 955                 960

Lys Val Ile Thr Leu Lys Ser Lys Leu Val Ser Asp Phe Arg Lys Asp
                965                 970                 975

Phe Gln Phe Tyr Lys Val Arg Glu Ile Asn Asn Tyr His His Ala His
                980                 985                 990

Asp Ala Tyr Leu Asn Ala Val Val Gly Thr Ala Leu Ile Lys Lys Tyr
                995                 1000                1005

Pro Lys Leu Glu Ser Glu Phe Val Tyr Gly Asp Tyr Lys Val Tyr
    1010                1015                1020

Asp Val Arg Lys Met Ile Ala Lys Ser Glu Gln Glu Ile Gly Lys
    1025                1030                1035

Ala Thr Ala Lys Tyr Phe Phe Tyr Ser Asn Ile Met Asn Phe Phe
    1040                1045                1050

Lys Thr Glu Ile Thr Leu Ala Asn Gly Glu Ile Arg Lys Arg Pro
    1055                1060                1065

Leu Ile Glu Thr Asn Gly Glu Thr Gly Glu Ile Val Trp Asp Lys
    1070                1075                1080

Gly Arg Asp Phe Ala Thr Val Arg Lys Val Leu Ser Met Pro Gln
    1085                1090                1095

Val Asn Ile Val Lys Lys Thr Glu Val Gln Thr Gly Gly Phe Ser
```

| | | | | | | | | | | |
|---|---|---|---|---|---|---|---|---|---|---|
| | | 1100 | | | | 1105 | | | | 1110 |
| Lys | Glu | Ser | Ile | Leu | Pro | Lys | Arg | Asn | Ser | Asp | Lys | Leu | Ile | Ala |
| | | 1115 | | | | 1120 | | | | 1125 | | | | |

Arg Lys Lys Asp Trp Asp Pro Lys Lys Tyr Gly Gly Phe Asp Ser
1130              1135              1140

Pro Thr Val Ala Tyr Ser Val Leu Val Val Ala Lys Val Glu Lys
1145              1150              1155

Gly Lys Ser Lys Lys Leu Lys Ser Val Lys Glu Leu Leu Gly Ile
1160              1165              1170

Thr Ile Met Glu Arg Ser Ser Phe Glu Lys Asn Pro Ile Asp Phe
1175              1180              1185

Leu Glu Ala Lys Gly Tyr Lys Glu Val Lys Lys Asp Leu Ile Ile
1190              1195              1200

Lys Leu Pro Lys Tyr Ser Leu Phe Glu Leu Glu Asn Gly Arg Lys
1205              1210              1215

Arg Met Leu Ala Ser Ala Gly Glu Leu Gln Lys Gly Asn Glu Leu
1220              1225              1230

Ala Leu Pro Ser Lys Tyr Val Asn Phe Leu Tyr Leu Ala Ser His
1235              1240              1245

Tyr Glu Lys Leu Lys Gly Ser Pro Glu Asp Asn Glu Gln Lys Gln
1250              1255              1260

Leu Phe Val Glu Gln His Lys His Tyr Leu Asp Glu Ile Ile Glu
1265              1270              1275

Gln Ile Ser Glu Phe Ser Lys Arg Val Ile Leu Ala Asp Ala Asn
1280              1285              1290

Leu Asp Lys Val Leu Ser Ala Tyr Asn Lys His Arg Asp Lys Pro
1295              1300              1305

Ile Arg Glu Gln Ala Glu Asn Ile Ile His Leu Phe Thr Leu Thr
1310              1315              1320

Asn Leu Gly Ala Pro Ala Ala Phe Lys Tyr Phe Asp Thr Thr Ile
1325              1330              1335

Asp Arg Lys Arg Tyr Thr Ser Thr Lys Glu Val Leu Asp Ala Thr
1340              1345              1350

Leu Ile His Gln Ser Ile Thr Gly Leu Tyr Glu Thr Arg Ile Asp
1355              1360              1365

Leu Ser Gln Leu Gly Gly Asp Lys Arg Pro Ala Ala Thr Lys Lys
1370              1375              1380

Ala Gly Gln Ala Lys Lys Lys Lys
1385              1390

<210> SEQ ID NO 54
<211> LENGTH: 4173
<212> TYPE: DNA
<213> ORGANISM: Artificial Sequence
<220> FEATURE:
<223> OTHER INFORMATION: Synthetic

<400> SEQUENCE: 54
atggacaagc ccaagaaaaa gcggaaagtg aagtacagca tcggcctgga catcggcacc     60
aactctgtgg ctgggccgt gatcaccgac gagtacaagg tgcccagcaa gaaattcaag    120
gtgctgggca acaccgacag cacagcatc aagaagaacc tgatcggcgc cctgctgttc    180
gacagcggcg aaacagccga ggccaccaga ctgaagagaa ccgccagaag aagatacacc    240
aggcggaaga caggatctg ctatctgcaa gagatcttca gcaacgagat ggccaaggtg    300

|  |  |  |  |  |  |
|---|---|---|---|---|---|
| gacgacagct | tcttccacag | actggaagag | tccttcctgg | tggaagagga | caagaagcac | 360 |
| gagagacacc | ccatcttcgg | caacatcgtg | gacgaggtgg | cctaccacga | gaagtacccc | 420 |
| accatctacc | acctgagaaa | gaaactggtg | gacagcaccg | acaaggccga | cctgagactg | 480 |
| atctacctgg | ccctggccca | catgatcaag | ttcagaggcc | acttcctgat | cgagggcgac | 540 |
| ctgaaccccg | acaacagcga | cgtggacaag | ctgttcatcc | agctggtgca | gacctacaac | 600 |
| cagctgttcg | aggaaaaccc | catcaacgcc | agcggcgtgg | acgccaaggc | tatcctgtct | 660 |
| gccagactga | gcaagagcag | aaggctggaa | atctgatcg | cccagctgcc | cggcgagaag | 720 |
| aagaacggcc | tgttcggcaa | cctgattgcc | ctgagcctgg | gcctgacccc | caacttcaag | 780 |
| agcaacttcg | acctggccga | ggatgccaaa | ctgcagctga | gcaaggacac | ctacgacgac | 840 |
| gacctggaca | acctgctggc | ccagatcggc | gaccagtacg | ccgacctgtt | cctggccgcc | 900 |
| aagaacctgt | ctgacgccat | cctgctgagc | gacatcctga | gagtgaacac | cgagatcacc | 960 |
| aaggccccc | tgagcgcctc | tatgatcaag | agatacgacg | agcaccacca | ggacctgacc | 1020 |
| ctgctgaaag | ctctcgtgcg | gcagcagctg | cctgagaagt | acaaagaaat | cttcttcgac | 1080 |
| cagagcaaga | acggctacgc | cggctacatc | gatggcggcg | ctagccagga | agagttctac | 1140 |
| aagttcatca | agcccatcct | ggaaaagatg | gacggcaccg | aggaactgct | cgtgaagctg | 1200 |
| aacagagagg | acctgctgag | aaagcagaga | accttcgaca | acggcagcat | cccccaccag | 1260 |
| atccacctgg | gagagctgca | cgctatcctg | agaaggcagg | aagatttta | cccattcctg | 1320 |
| aaggacaacc | gggaaaagat | cgagaagatc | ctgaccttca | ggatcccta | ctacgtgggc | 1380 |
| cccctggcca | gaggcaacag | cagattcgcc | tggatgacca | gaaagagcga | ggaaaccatc | 1440 |
| accccctgga | acttcgagga | agtggtggac | aagggcgcca | gcgcccagag | cttcatcgag | 1500 |
| agaatgacaa | acttcgataa | gaacctgccc | aacgagaagg | tgctgcccaa | gcacagcctg | 1560 |
| ctgtacgagt | acttcaccgt | gtacaacgag | ctgaccaaag | tgaaatacgt | gaccgaggga | 1620 |
| atgagaaagc | ccgccttcct | gagcggcgag | cagaaaaagg | ccatcgtgga | cctgctgttc | 1680 |
| aagaccaaca | gaaaagtgac | cgtgaagcag | ctgaagagg | actacttcaa | gaaaatcgag | 1740 |
| tgcttcgact | ccgtggaaat | ctccggcgtg | gaagatagat | caacgcctc | cctgggcaca | 1800 |
| taccacgatc | tgctgaaaat | tatcaaggac | aaggacttcc | tggataacga | agagaacgag | 1860 |
| gacattctgg | aagatatcgt | gctgaccctg | acactgtttg | aggaccgcga | gatgatcgag | 1920 |
| gaaaggctga | aacctacgc | tcacctgttc | gacgacaaag | tgatgaagca | gctgaagaga | 1980 |
| aggcggtaca | ccggctgggg | caggctgagc | agaaagctga | tcaacggcat | cagagacaag | 2040 |
| cagagcggca | agacaatcct | ggatttcctg | aagtccgacg | gcttcgccaa | ccggaacttc | 2100 |
| atgcagctga | tccacgacga | cagcctgaca | ttcaaagagg | acatccagaa | agcccaggtg | 2160 |
| tccggccagg | gcgactctct | gcacgagcat | atcgctaacc | tggccggcag | ccccgctatc | 2220 |
| aagaagggca | tcctgcagac | agtgaaggtg | gtggacgagc | tcgtgaaagt | gatgggcaga | 2280 |
| cacaagcccg | agaacatcgt | gatcgagatg | gctagagaa | accagaccac | ccagaaggga | 2340 |
| cagaagaact | cccgcgagag | gatgaagaga | atcgaagagg | gcatcaaaga | gctgggcagc | 2400 |
| cagatcctga | agaacacccc | cgtggaaaac | acccagctgc | agaacgagaa | gctgtacctg | 2460 |
| tactacctgc | agaatggccg | ggatatgtac | gtggaccagg | aactggacat | caacagactg | 2520 |
| tccgactacg | atgtggacca | tatcgtgcct | cagagctttc | tgaaggacga | ctccatcgat | 2580 |
| aacaaagtgc | tgactcggag | cgacaagaac | agaggcaaga | gcgacaacgt | gcctccgaa | 2640 |
| gaggtcgtga | agaagatgaa | gaactactgg | cgacagctgc | tgaacgccaa | gctgattacc | 2700 |

```
cagaggaagt tcgataacct gaccaaggcc gagagaggcg gcctgagcga gctggataag    2760
gccggcttca tcaagaggca gctggtggaa accagacaga tcacaaagca cgtggcacag    2820
atcctggact cccggatgaa cactaagtac gacgaaaacg ataagctgat ccgggaagtg    2880
aaagtgatca ccctgaagtc caagctggtg tccgatttcc ggaaggattt ccagttttac    2940
aaagtgcgcg agatcaacaa ctaccaccac gcccacgacg cctacctgaa cgccgtcgtg    3000
ggaaccgccc tgatcaaaaa gtaccctaag ctggaaagcg agttcgtgta cggcgactac    3060
aaggtgtacg acgtgcggaa gatgatcgcc aagagcgagc aggaaatcgg caaggctacc    3120
gccaagtact tcttctacag caacatcatg aacttttca agaccgaaat caccctggcc      3180
aacggcgaga tcagaaagcg ccctctgatc gagacaaacg gcgaaaccgg ggagatcgtg    3240
tgggataagg gcagagactt cgccacagtg cgaaaggtgc tgagcatgcc caagtgaat    3300 atcgtgaaaa agaccgaggt gcagacaggc ggcttcagca aagagtctat cctgcccaag    3360
aggaacagcg acaagctgat cgccagaaag aaggactggg accccaagaa gtacggcggc    3420
ttcgacagcc ctaccgtggc ctactctgtg ctggtggtgg ctaaggtgga aaagggcaag    3480
tccaagaaac tgaagagtgt gaaagagctg ctggggatca ccatcatgga agaagcagc     3540 tttgagaaga cccctatcga ctttctggaa gccaagggct acaagaagt gaaaaggac      3600 ctgatcatca agctgcctaa gtactccctg ttcgagctgg aaaacggcag aaagagaatg    3660
ctggcctctg ccggcgaact gcagaaggga acgagctgg ccctgcctag caaatatgtg     3720
aacttcctgt acctggcctc ccactatgag aagctgaagg gcagccctga ggacaacgaa    3780
cagaaacagc tgtttgtgga acagcataag cactacctgg acgagatcat cgagcagatc    3840
agcgagttct ccaagagagt gatcctggcc gacgccaatc tggacaaggt gctgtctgcc    3900
tacaacaagc acagggacaa gcctatcaga gagcaggccg agaatatcat ccacctgttc    3960
accctgacaa acctgggcgc tcctgccgcc ttcaagtact tgacaccac catcgaccgg    4020 aagaggtaca ccagcaccaa agaggtgctg gacgccaccc tgatccacca gagcatcacc    4080
ggcctgtacg agacaagaat cgacctgtct cagctgggag gcgacaagag acctgccgcc    4140
actaagaagg ccggacaggc caaaaagaag aag                                 4173

<210> SEQ ID NO 55
<211> LENGTH: 23
<212> TYPE: RNA
<213> ORGANISM: Artificial Sequence
<220> FEATURE:
<223> OTHER INFORMATION: Synthetic

<400> SEQUENCE: 55
gcugaagcac ugcacgccau ggg                                              23

<210> SEQ ID NO 56
<211> LENGTH: 23
<212> TYPE: DNA
<213> ORGANISM: Artificial Sequence
<220> FEATURE:
<223> OTHER INFORMATION: Synthetic

<400> SEQUENCE: 56
gctgaagcac tgcacgccat ggg                                              23

<210> SEQ ID NO 57
<211> LENGTH: 1499
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(172)
<223> OTHER INFORMATION: Mouse Upstream Sequence
<220> FEATURE:
<221> NAME/KEY: misc_feature
<222> LOCATION: (300)..(333)
<223> OTHER INFORMATION: LoxP
<220> FEATURE:
<221> NAME/KEY: misc_feature
<222> LOCATION: (379)..(1098)
<223> OTHER INFORMATION: eBFP
<220> FEATURE:
<221> NAME/KEY: misc_feature
<222> LOCATION: (1133)..(1354)
<223> OTHER INFORMATION: SV40 Poly(A)
<220> FEATURE:
<221> NAME/KEY: misc_feature
<222> LOCATION: (1355)..(1499)
<223> OTHER INFORMATION: Mouse Downstream Sequence

<400> SEQUENCE: 57
```

| | | | | |
|---|---|---|---|---|
| ctgcagtgga | gtaggcgggg | agaaggccgc | acccttctcc | ggaggggggga | ggggagtgtt | 60 |
| gcaataccctt | tctgggagtt | ctctgctgcc | tcctggcttc | tgaggaccgc | cctgggcctg | 120 |
| ggagaatccc | ttcccctct | tccctcgtga | tctgcaactc | cagtctttct | agttgaccag | 180 |
| ctcggcggtg | acctgcacgt | ctagggcgca | gtagtccagg | gtttccttga | tgatgtcata | 240 |
| cttatcctgt | cccttttttt | tccacagggc | gcgccactag | tggatccgga | acccttaata | 300 |
| taacttcgta | taatgtatgc | tatacgaagt | tattaggtcc | ctcgacctgc | agcccaagct | 360 |
| agtgcccggg | ccgccaccat | ggtgagcaag | ggcgaggagc | tgttcaccgg | ggtggtgccc | 420 |
| atcctggttg | agctggacgg | cgacgtaaac | ggccacaagt | tcagcgtgtc | cggcgagggc | 480 |
| gagggcgatg | ccacctacgg | caagctgacc | ctgaagttca | tctgcaccac | cggcaagctg | 540 |
| cccgtgccct | ggcccaccct | cgtgaccacc | ctgacccatg | gcgtgcagtg | cttcagccgc | 600 |
| taccccgacc | acatgaagca | gcacgacttc | ttcaagtccg | ccatgcccga | aggctacgtc | 660 |
| caggagcgca | ccatcttctt | caaggacgac | ggcaactaca | agacccgcgc | cgaggtgaag | 720 |
| ttcgagggcg | acaccctggt | gaaccgcatc | gagctgaagg | gcatcgactt | caaggaggac | 780 |
| ggcaacatcc | tggggcacaa | gctggagtac | aactacaaca | gccacaacgt | ctatatcatg | 840 |
| gccgacaagc | agaagaacgg | catcaaggtg | aacttcaaga | tccgccacaa | catcgaggac | 900 |
| ggcagcgtgc | agctcgccga | ccactaccag | cagaacaccc | ccatcggcga | cggccccgtg | 960 |
| ctgctgcccg | acaaccacta | cctgagcacc | cagtccgccc | tgagcaaaga | ccccaacgag | 1020 |
| aagcgcgatc | acatggtcct | gctggagttc | gtgaccgccg | ccgggatcac | tctcggcatg | 1080 |
| gacgagctgt | acaagtaata | attctagagt | cggggcggcc | ggccgcttcg | agcagacatg | 1140 |
| ataagataca | ttgatgagtt | tggacaaacc | acaactagaa | tgcagtgaaa | aaaatgcttt | 1200 |
| atttgtgaaa | tttgtgatgc | tattgcttta | tttgtaacca | ttataagctg | caataaacaa | 1260 |
| gttaacaaca | acaattgcat | tcattttatg | tttcaggttc | agggggaggt | gtgggaggtt | 1320 |
| ttttaaagca | agtaaaacct | ctacaaatgt | ggtactcgag | taaaattgga | gggacaagac | 1380 |
| ttcccacaga | ttttcggttt | tgtcgggaag | ttttttaata | ggggcaaata | aggaaaatgg | 1440 |
| gaggataggt | agtcatctgg | ggttttatgc | agcaaaacta | caggttatta | ttgcttgtg | 1499 |

```
<210> SEQ ID NO 58
<211> LENGTH: 7235
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(120)
<223> OTHER INFORMATION: Mouse Upstream Sequence
<220> FEATURE:
<221> NAME/KEY: misc_feature
<222> LOCATION: (248)..(281)
<223> OTHER INFORMATION: LoxP
<220> FEATURE:
<221> NAME/KEY: misc_feature
<222> LOCATION: (290)..(3358)
<223> OTHER INFORMATION: LacZ
<220> FEATURE:
<221> NAME/KEY: misc_feature
<222> LOCATION: (3359)..(3424)
<223> OTHER INFORMATION: P2A
<220> FEATURE:
<221> NAME/KEY: misc_feature
<222> LOCATION: (3425)..(4141)
<223> OTHER INFORMATION: eBFP
<220> FEATURE:
<221> NAME/KEY: misc_feature
<222> LOCATION: (4176)..(4397)
<223> OTHER INFORMATION: SV40 Poly(A)
<220> FEATURE:
<221> NAME/KEY: misc_feature
<222> LOCATION: (4404)..(4451)
<223> OTHER INFORMATION: Frt
<220> FEATURE:
<221> NAME/KEY: misc_feature
<222> LOCATION: (4458)..(5670)
<223> OTHER INFORMATION: Ubiquitin Promoter
<220> FEATURE:
<221> NAME/KEY: misc_feature
<222> LOCATION: (5671)..(5737)
<223> OTHER INFORMATION: EM7 Promoter
<220> FEATURE:
<221> NAME/KEY: misc_feature
<222> LOCATION: (5738)..(6541)
<223> OTHER INFORMATION: Neomycin Phosphotransferase
<220> FEATURE:
<221> NAME/KEY: misc_feature
<222> LOCATION: (6550)..(7026)
<223> OTHER INFORMATION: Pgk Poly(A)
<220> FEATURE:
<221> NAME/KEY: misc_feature
<222> LOCATION: (7037)..(7084)
<223> OTHER INFORMATION: Frt
<220> FEATURE:
<221> NAME/KEY: misc_feature
<222> LOCATION: (7091)..(7235)
<223> OTHER INFORMATION: Mouse Downstream Sequence

<400> SEQUENCE: 58
ggagtgttgc aataccttttc tgggagttct ctgctgcctc ctggcttctg aggaccgccc      60
tgggcctggg agaatccctt ccccctcttc cctcgtgatc tgcaactcca gtctttctag     120
ttgaccagct cggcggtgac ctgcacgtct agggcgcagt agtccagggt ttccttgatg     180
atgtcatact tatcctgtcc cttttttttc cacaggcgc gccactagtg gatccggaac      240
ccttaatata acttcgtata atgtatgcta tacgaagtta tccgccacca tgggtaccga     300
tttaaatgat ccagtggtcc tgcagaggag agattgggag aatcccggtg tgacacagct     360
gaacagacta gccgcccacc ctcccttttgc ttcttggaga acagtgagg aagctaggac      420 agacagacca agccagcaac tcagatcttt gaacggggag tggagatttg cctggttttcc    480 ggcaccagaa gcggtgccgg aaagctggct ggagtgcgat cttcctgagg ccgatactgt     540
cgtcgtcccc tcaaactggc agatgcacgg ttacgatgcg cccatctaca ccaacgtgac     600
```

| | |
|---|---:|
| ctatcccatt acggtcaatc cgccgtttgt tcccacggag aatccgacgg gttgttactc | 660 |
| gctcacattt aatgttgatg aaagctggct acaggaaggc cagacgcgaa ttattttga | 720 |
| tggcgttaac tcggcgtttc atctgtggtg caacgggcgc tgggtcggtt acggccagga | 780 |
| cagtcgtttg ccgtctgaat ttgacctgag cgcatttta cgcgccggag aaaaccgcct | 840 |
| cgcggtgatg gtgctgcgct ggagtgacgg cagttatctg gaagatcagg atatgtggcg | 900 |
| gatgagcggc attttccgtg acgtctcgtt gctgcataaa ccgactacac aaatcagcga | 960 |
| tttccatgtt gccactcgct ttaatgatga tttcagccgc gctgtactgg aggctgaagt | 1020 |
| tcagatgtgc ggcgagttgc gtgactacct acgggtaaca gtttctttat ggcagggtga | 1080 |
| aacgcaggtc gccagcggca ccgcgccttt cggcggtgaa attatcgatg agcgtggtgg | 1140 |
| ttatgccgat cgcgtcacac tacgtctgaa cgtcgaaaac ccgaaactgt ggagcgccga | 1200 |
| aatcccgaat ctctatcgtg cggtggttga actgcacacc gccgacggca cgctgattga | 1260 |
| agcagaagcc tgcgatgtcg gtttccgcga ggtgcggatt gaaatggtc tgctgctgct | 1320 |
| gaacggcaag ccgttgctga ttcgaggcgt taaccgtcac gagcatcatc ctctgcatgg | 1380 |
| tcaggtcatg gatgagcaga cgatggtgca ggatatcctg ctgatgaagc agaacaactt | 1440 |
| taacgccgtg cgctgttcgc attatccgaa ccatccgctg tggtacacgc tgtgcgaccg | 1500 |
| ctacggcctg tatgtggtgg atgaagccaa tattgaaacc cacggcatgg tgccaatgaa | 1560 |
| tcgtctgacc gatgatccgc gctggctacc ggcgatgagc gaacgcgtaa cgcgaatggt | 1620 |
| gcagcgcgat cgtaatcacc cgagtgtgat catctggtcg ctggggaatg aatcaggcca | 1680 |
| cggcgctaat cacgacgcgc tgtatcgctg gatcaaatct gtcgatcctt cccgcccggt | 1740 |
| gcagtatgaa ggcggcggag ccgacaccac ggccaccgat attatttgcc cgatgtacgc | 1800 |
| gcgcgtggat gaagaccagc ccttcccggc tgtgccgaaa tggtccatca aaaaatggct | 1860 |
| ttcgctacct ggagagacgc gcccgctgat cctttgcgaa tacgcccacg cgatgggtaa | 1920 |
| cagtcttggc ggtttcgcta aatactggca ggcgtttcgt cagtatcccc gtttacaggg | 1980 |
| cggcttcgtc tgggactggg tggatcagtc gctgattaaa tatgatgaaa acggcaaccc | 2040 |
| gtggtcggct tacggcggtg attttggcga tacgccgaac gatcgccagt tctgtatgaa | 2100 |
| cggtctggtc tttgccgacc gcacgccgca tccagcgctg acggaagcaa acaccagca | 2160 |
| gcagtttttc cagttccgtt tatccgggca accatcgaa gtgaccagcg aatacctgtt | 2220 |
| ccgtcatagc gataacgagc tcctgcactg gatggtggcg ctggatggta agccgctggc | 2280 |
| aagcggtgaa gtgcctctgg atgtcgctcc acaaggtaaa cagttgattg aactgcctga | 2340 |
| actaccgcag ccggagagcg ccgggcaact ctggctcaca gtacgcgtag tgcaaccgaa | 2400 |
| cgcgaccgca tggtcagaag ccgggcacat cagcgcctgg cagcagtggc gtctggcgga | 2460 |
| aaacctcagt gtgacgctcc ccgccgcgtc ccacgccatc ccgcatctga ccaccagcga | 2520 |
| aatggatttt tgcatcgagc tgggtaataa gcgttggcaa tttaaccgcc agtcaggctt | 2580 |
| tctttcacag atgtggattg gcgataaaaa acaactgctg acgccgctgc gcgatcagtt | 2640 |
| cacccgtgca ccgctggata acgacattgg cgtaagtgaa gcgacccgca ttgaccctaa | 2700 |
| cgcctgggtc gaacgctgga aggcggcggg ccattaccag gccgaagcag cgttgttgca | 2760 |
| gtgcacggca gatacacttg ctgatgcggt gctgattacg accgctcacg cgtggcagca | 2820 |
| tcaggggaaa accttatta tcagccgaa aacctaccgg attgatggta gtggtcaaat | 2880 |
| ggcgattacc gttgatgttg aagtggcgag cgatacaccg catccggcgc ggattggcct | 2940 |
| gaactgccag ctggcgcagg tagcagagcg ggtaaactgg ctcggattag ggccgcaaga | 3000 |

```
aaactatccc gaccgcctta ctgccgcctg ttttgaccgc tgggatctgc cattgtcaga      3060
catgtatacc ccgtacgtct tcccgagcga aaacggtctg cgctgcggga cgcgcgaatt      3120
gaattatggc ccacaccagt ggcgcggcga cttccagttc aacatcagcc gctacagtca      3180
acagcaactg atggaaacca gccatcgcca tctgctgcac gcggaagaag gcacatggct      3240
gaatatcgac ggtttccata tggggattgg tggcgacgac tcctggagcc cgtcagtatc      3300
ggcggaattc cagctgagcg ccggtcgcta ccattaccag ttggtctggt gtcaaaaagg      3360
aagcggagct actaacttca gcctgctgaa gcaggctgga gacgtggagg agaaccctgg      3420
acctgtgagc aagggcgagg agctgttcac cggggtggtg cccatcctgg tcgagctgga      3480
cggcgacgta aacggccaca gttcagcgt gtccggcgag ggcgagggcg atgccaccta      3540
cggcaagctg accctgaagt tcatctgcac caccggcaag ctgcccgtgc cctggcccac      3600
cctcgtgacc accctgaccc atggcgtgca gtgcttcagc cgctaccccg accacatgaa      3660
gcagcacgac ttcttcaagt ccgccatgcc cgaaggctac gtccaggagc gcaccatctt      3720
cttcaaggac gacggcaact acaagacccg cgccgaggtg aagttcgagg gcgacaccct      3780
ggtgaaccgc atcgagctga agggcatcga cttcaaggag gacggcaaca tcctggggca      3840
caagctggag tacaactaca acagccacaa cgtctatatc atggccgaca gcagaagaa      3900
cggcatcaag gtgaacttca agatccgcca caacatcgag gacggcagcg tgcagctcgc      3960
cgaccactac cagcagaaca cccccatcgg cgacggcccc gtgctgctgc ccgacaacca      4020
ctacctgagc acccagtccg ccctgagcaa agacccaac gagaagcgcg atcacatggt      4080
cctgctggag ttcgtgaccg ccgccgggat cactctcggc atggacgagc tgtacaagta      4140
ataattctag agtcggggcg gccggccgct tcgagcagac atgataagat acattgatga      4200
gtttggacaa accacaacta gaatgcagtg aaaaaaatgc tttatttgtg aaatttgtga      4260
tgctattgct ttatttgtaa ccattataag ctgcaataaa caagttaaca acaacaattg      4320
cattcatttt atgtttcagg ttcaggggga ggtgtgggag gttttttaaa gcaagtaaaa      4380
cctctacaaa tgtggtactc gaggaagttc ctattccgaa gttcctattc tctagaaagt      4440
ataggaactt catgcatggc ctccgcgccg ggttttggcg cctcccgcgg gcgcccccct      4500
cctcacggcg agcgctgcca cgtcagacga agggcgcagc gagcgtcctg atccttccgc      4560
ccggacgctc aggacagcgg cccgctgctc ataagactcg gccttagaac cccagtatca      4620
gcagaaggac attttaggac gggacttggg tgactctagg cactggtttt ctttccaga      4680
gagcggaaca ggcgaggaaa agtagtccct tctcggcgat tctgcggagg gatctccgtg      4740
gggcggtgaa cgccgatgat tatataagga cgcgccgggt gtggcacagc tagttccgtc      4800
gcagccggga tttgggtcgc ggttcttgtt tgtggatcgc tgtgatcgtc acttggtgag      4860
tagcgggctg ctgggctggc cggggctttc gtggccgccg ggccgctcgg tgggacggaa      4920
gcgtgtggag agaccgccaa gggctgtagt ctgggtccgc gagcaaggtt gccctgaact      4980
gggggttggg gggagcgcag caaaatggcg gctgttcccg agtcttgaat ggaagacgct      5040
tgtgaggcgg gctgtgaggt cgttgaaaca aggtgggggg catggtgggc ggcaagaacc      5100
caaggtcttg aggccttcgc taatgcggga agctcttat tcgggtgaga tgggctgggg      5160
caccatctgg ggaccctgac gtgaagtttg tcactgactg gagaactcgg tttgtcgtct      5220
gttgcggggg cggcagttat ggcggtgccg ttggcagtg cacccgtacc tttgggagcg      5280
cgcgccctcg tcgtgtcgtg acgtcacccg ttctgttggc ttataatgca gggtgggggcc      5340
```

| | |
|---|---|
| acctgccggt aggtgtgcgg taggcttttc tccgtcgcag gacgcagggt tcgggcctag | 5400 |
| ggtaggctct cctgaatcga caggcgccgg acctctggtg aggggaggga taagtgaggc | 5460 |
| gtcagtttct ttggtcggtt ttatgtacct atcttcttaa gtagctgaag ctccggtttt | 5520 |
| gaactatgcg ctcggggttg gcgagtgtgt tttgtgaagt tttttaggca ccttttgaaa | 5580 |
| tgtaatcatt tgggtcaata tgtaattttc agtgttagac tagtaaattg tccgctaaat | 5640 |
| tctggccgtt tttggctttt ttgttagacg tgttgacaat taatcatcgg catagtatat | 5700 |
| cggcatagta taatacgaca aggtgaggaa ctaaaccatg ggatcggcca ttgaacaaga | 5760 |
| tggattgcac gcaggttctc cggccgcttg ggtggagagg ctattcggct atgactgggc | 5820 |
| acaacagaca atcggctgct ctgatgccgc cgtgttccgg ctgtcagcgc aggggcgccc | 5880 |
| ggttcttttt gtcaagaccg acctgtccgg tgccctgaat gaactgcagg acgaggcagc | 5940 |
| gcggctatcg tggctggcca cgacgggcgt tccttgcgca gctgtgctcg acgttgtcac | 6000 |
| tgaagcggga agggactggc tgctattggg cgaagtgccg gggcaggatc tcctgtcatc | 6060 |
| tcaccttgct cctgccgaga agtatccat catggctgat gcaatgcggc ggctgcatac | 6120 |
| gcttgatccg gctacctgcc cattcgacca ccaagcgaaa catcgcatcg agcgagcacg | 6180 |
| tactcggatg aagccggtc ttgtcgatca ggatgatctg gacgaagagc atcagggct | 6240 |
| cgcgccagcc gaactgttcg ccaggctcaa ggcgcgcatg cccgacggcg atgatctcgt | 6300 |
| cgtgacccat ggcgatgcct gcttgccgaa tatcatggtg aaaatggcc gcttttctgg | 6360 |
| attcatcgac tgtggccggc tgggtgtggc ggaccgctat caggacatag cgttggctac | 6420 |
| ccgtgatatt gctgaagagc ttggcggcga atgggctgac cgcttcctcg tgctttacgg | 6480 |
| tatcgccgct cccgattcgc agcgcatcgc cttctatcgc cttcttgacg agttcttctg | 6540 |
| aggggatccg ctgtaagtct gcagaaattg atgatctatt aaacaataaa gatgtccact | 6600 |
| aaaatggaag ttttcctgt catactttgt taagaagggt gagaacagag tacctacatt | 6660 |
| ttgaatggaa ggattggagc tacggggggt ggggtggggt gggattagat aaatgcctgc | 6720 |
| tctttactga aggctcttta ctattgcttt atgataatgt ttcatagttg gatatcataa | 6780 |
| tttaaacaag caaaaccaaa ttaagggcca gctcattcct cccactcatg atctatagat | 6840 |
| ctatagatct ctcgtgggat cattgttttt ctcttgattc ccactttgtg gttctaagta | 6900 |
| ctgtggtttc caaatgtgtc agtttcatag cctgaagaac gagatcagca gcctctgttc | 6960 |
| cacatacact tcattctcag tattgttttg ccaagttcta attccatcag acctcgacct | 7020 |
| gcagccccta gtcgacgaag ttcctattcc gaagttccta ttctctagaa agtataggaa | 7080 |
| cttcgctagc taaaattgga gggacaagac ttcccacaga ttttcggttt tgtcgggaag | 7140 |
| ttttttaata ggggcaaata aggaaaatgg gaggataggt agtcatctgg ggttttatgc | 7200 |
| agcaaaacta caggttatta ttgcttgtga tccgc | 7235 |

<210> SEQ ID NO 59
<211> LENGTH: 7235
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(120)
<223> OTHER INFORMATION: Mouse Upstream Sequence
<220> FEATURE:
<221> NAME/KEY: misc_feature
<222> LOCATION: (248)..(281)
<223> OTHER INFORMATION: LoxP

```
<220> FEATURE:
<221> NAME/KEY: misc_feature
<222> LOCATION: (290)..(3358)
<223> OTHER INFORMATION: LacZ
<220> FEATURE:
<221> NAME/KEY: misc_feature
<222> LOCATION: (3359)..(3424)
<223> OTHER INFORMATION: P2A
<220> FEATURE:
<221> NAME/KEY: misc_feature
<222> LOCATION: (3425)..(4141)
<223> OTHER INFORMATION: eGFP
<220> FEATURE:
<221> NAME/KEY: misc_feature
<222> LOCATION: (4176)..(4397)
<223> OTHER INFORMATION: SV40 Poly(A)
<220> FEATURE:
<221> NAME/KEY: misc_feature
<222> LOCATION: (4404)..(4451)
<223> OTHER INFORMATION: Frt
<220> FEATURE:
<221> NAME/KEY: misc_feature
<222> LOCATION: (4458)..(5670)
<223> OTHER INFORMATION: Ubiquitin Promoter
<220> FEATURE:
<221> NAME/KEY: misc_feature
<222> LOCATION: (5671)..(5737)
<223> OTHER INFORMATION: EM7 Promoter
<220> FEATURE:
<221> NAME/KEY: misc_feature
<222> LOCATION: (5738)..(6541)
<223> OTHER INFORMATION: Neomycin Phosphotransferase
<220> FEATURE:
<221> NAME/KEY: misc_feature
<222> LOCATION: (6550)..(7026)
<223> OTHER INFORMATION: Pgk Poly(A)
<220> FEATURE:
<221> NAME/KEY: misc_feature
<222> LOCATION: (7037)..(7084)
<223> OTHER INFORMATION: Frt
<220> FEATURE:
<221> NAME/KEY: misc_feature
<222> LOCATION: (7091)..(7235)
<223> OTHER INFORMATION: Mouse Downstream Sequence

<400> SEQUENCE: 59
ggagtgttgc aataccttc tgggagttct ctgctgcctc ctggcttctg aggaccgccc      60
tgggcctggg agaatccctt cccctcttc cctcgtgatc tgcaactcca gtctttctag    120
ttgaccagct cggcggtgac ctgcacgtct agggcgcagt agtccagggt ttccttgatg    180
atgtcatact tatcctgtcc ctttttttc cacagggcgc gccactagtg gatccggaac    240
ccttaatata acttcgtata atgtatgcta tacgaagtta ccgccacca tgggtaccga    300 tttaaatgat ccagtggtcc tgcagaggag agattgggag aatcccggtg tgacacagct    360
gaacagacta gccgcccacc ctcccttgc ttcttggaga acagtgagg aagctaggac      420 agacagacca agccagcaac tcagatcttt gaacggggag tggagatttg cctggtttcc    480
ggcaccagaa gcggtgccgg aaagctggct ggagtgcgat cttcctgagg ccgatactgt    540
cgtcgtcccc tcaaactggc agatgcacgg ttacgatgcg cccatctaca ccaacgtgac    600
ctatcccatt acggtcaatc cgccgtttgt tcccacggag aatccgacgg ttgttactc    660 gctcacattt aatgttgatg aaagctggct acaggaaggc cagacgcgaa ttatttttga    720
tggcgttaac tcggcgtttc atctgtggtg caacgggcgc tgggtcggtt acggccagga    780
cagtcgtttg ccgtctgaat ttgacctgag cgcattttta cgcgccggag aaaaccgcct    840
cgcggtgatg gtgctgcgct ggagtgacgg cagttatctg gaagatcagg atatgtggcg    900
gatgagcggc attttccgtg acgtctcgtt gctgcataaa ccgactacac aaatcagcga    960
```

| | | | | | |
|---|---|---|---|---|---|
| tttccatgtt | gccactcgct | ttaatgatga | tttcagccgc | gctgtactgg | aggctgaagt | 1020 |
| tcagatgtgc | ggcgagttgc | gtgactacct | acgggtaaca | gtttcttat | ggcagggtga | 1080 |
| aacgcaggtc | gccagcggca | ccgcgccttt | cggcggtgaa | attatcgatg | agcgtggtgg | 1140 |
| ttatgccgat | cgcgtcacac | tacgtctgaa | cgtcgaaaac | ccgaaactgt | ggagcgccga | 1200 |
| aatcccgaat | ctctatcgtg | cggtggttga | actgcacacc | gccgacggca | cgctgattga | 1260 |
| agcagaagcc | tgcgatgtcg | gtttccgcga | ggtgcggatt | gaaaatggtc | tgctgctgct | 1320 |
| gaacggcaag | ccgttgctga | ttcgaggcgt | taaccgtcac | gagcatcatc | ctctgcatgg | 1380 |
| tcaggtcatg | gatgagcaga | cgatggtgca | ggatatcctg | ctgatgaagc | agaacaactt | 1440 |
| taacgccgtg | cgctgttcgc | attatccgaa | ccatccgctg | tggtacacgc | tgtgcgaccg | 1500 |
| ctacggcctg | tatgtggtgg | atgaagccaa | tattgaaacc | cacggcatgg | tgccaatgaa | 1560 |
| tcgtctgacc | gatgatccgc | gctggctacc | ggcgatgagc | gaacgcgtaa | cgcgaatggt | 1620 |
| gcagcgcgat | cgtaatcacc | cgagtgtgat | catctggtcg | ctggggaatg | aatcaggcca | 1680 |
| cggcgctaat | cacgacgcgc | tgtatcgctg | gatcaaatct | gtcgatcctt | cccgcccggt | 1740 |
| gcagtatgaa | ggcggcggag | ccgacaccac | ggccaccgat | attatttgcc | cgatgtacgc | 1800 |
| gcgcgtggat | gaagaccagc | ccttcccggc | tgtgccgaaa | tggtccatca | aaaaatggct | 1860 |
| ttcgctacct | ggagagacgc | gcccgctgat | cctttgcgaa | tacgcccacg | cgatgggtaa | 1920 |
| cagtcttggc | ggtttcgcta | aatactggca | ggcgtttcgt | cagtatcccc | gtttacaggg | 1980 |
| cggcttcgtc | tgggactggg | tggatcagtc | gctgattaaa | tatgatgaaa | acggcaaccc | 2040 |
| gtggtcggct | tacggcggtg | attttggcga | tacgccgaac | gatcgccagt | tctgtatgaa | 2100 |
| cggtctggtc | tttgccgacc | gcacgccgca | tccagcgctg | acggaagcaa | acaccagca | 2160 |
| gcagttttc | cagttccgtt | tatccgggca | aaccatcgaa | gtgaccagcg | aatacctgtt | 2220 |
| ccgtcatagc | gataacgagc | tcctgcactg | gatggtggcg | ctggatggta | agccgctggc | 2280 |
| aagcggtgaa | gtgcctctgg | atgtcgctcc | acaaggtaaa | cagttgattg | aactgcctga | 2340 |
| actaccgcag | ccggagagcg | ccgggcaact | ctggctcaca | gtacgcgtag | tgcaaccgaa | 2400 |
| cgcgaccgca | tggtcagaag | ccgggcacat | cagcgcctgg | cagcagtggc | gtctggcgga | 2460 |
| aaacctcagt | gtgacgctcc | ccgccgcgtc | ccacgccatc | ccgcatctga | ccaccagcga | 2520 |
| aatggatttt | tgcatcgagc | tgggtaataa | gcgttggcaa | tttaaccgcc | agtcaggctt | 2580 |
| tctttcacag | atgtggattg | gcgataaaaa | acaactgctg | acgccgctgc | gcgatcagtt | 2640 |
| cacccgtgca | ccgctggata | acgacattgg | cgtaagtgaa | gcgacccgca | ttgaccctaa | 2700 |
| cgcctgggtc | gaacgctgga | aggcggcggg | ccattaccag | gccgaagcag | cgttgttgca | 2760 |
| gtgcacggca | gatacacttg | ctgatgcggt | gctgattacg | accgctcacg | cgtggcagca | 2820 |
| tcaggggaaa | accttattta | tcagccggaa | aacctaccgg | attgatggta | gtggtcaaat | 2880 |
| ggcgattacc | gttgatgttg | aagtggcgag | cgataccccg | catccggcgc | ggattggcct | 2940 |
| gaactgccag | ctggcgcagg | tagcagagcg | ggtaaactgg | ctcggattag | gccgcaagaa | 3000 |
| aaactatccc | gaccgcctta | ctgccgcctg | ttttgaccgc | tgggatctgc | cattgtcaga | 3060 |
| catgtatacc | ccgtacgtct | tcccgagcga | aaacggtctg | cgctgcggga | cgcgcgaatt | 3120 |
| gaattatggc | ccacaccagt | ggcgcggcga | cttccagttc | aacatcagcc | gctacagtca | 3180 |
| acagcaactg | atggaaacca | gccatcgcca | tctgctgcac | gcggaagaag | gcacatggct | 3240 |
| gaatatcgac | ggtttccata | tggggattgg | tggcgacgca | tcctggagcc | cgtcagtatc | 3300 |
| ggcggaattc | cagctgagcg | ccggtcgcta | ccattaccag | ttggtctggt | gtcaaaaagg | 3360 |

```
aagcggagct actaacttca gcctgctgaa gcaggctgga gacgtggagg agaaccctgg    3420
acctgtgagc aagggcgagg agctgttcac cggggtggtg cccatcctgg tcgagctgga    3480
cggcgacgta aacggccaca gtttcagcgt gtccggcgag ggcgagggcg atgccaccta    3540
cggcaagctg accctgaagt tcatctgcac caccggcaag ctgcccgtgc cctggcccac    3600
cctcgtgacc accctgacct acggcgtgca gtgcttcagc cgctaccccg accacatgaa    3660
gcagcacgac ttcttcaagt ccgccatgcc cgaaggctac gtccaggagc gcaccatctt    3720
cttcaaggac gacggcaact acaagacccg cgccgaggtg aagttcgagg gcgacaccct    3780
ggtgaaccgc atcgagctga agggcatcga cttcaaggag gacggcaaca tcctggggca    3840
caagctggag tacaactaca acagccacaa cgtctatatc atggccgaca agcagaagaa    3900
cggcatcaag gtgaacttca agatccgcca caacatcgag gacggcagcg tgcagctcgc    3960
cgaccactac cagcagaaca cccccatcgg cgacggcccc gtgctgctgc ccgacaacca    4020
ctacctgagc acccagtccg ccctgagcaa agaccccaac gagaagcgcg atcacatggt    4080
cctgctggag ttcgtgaccg ccgccgggat cactctcggc atggacgagc tgtacaagta    4140
ataattctag agtcggggcg gccggccgct tcgagcagac atgataagat acattgatga    4200
gtttggacaa accacaacta gaatgcagtg aaaaaaatgc tttatttgtg aaatttgtga    4260
tgctattgct ttatttgtaa ccattataag ctgcaataaa caagttaaca acaacaattg    4320
cattcatttt atgtttcagg ttcagggggga ggtgtgggag gttttttaaa gcaagtaaaa    4380
cctctacaaa tgtggtactc gaggaagttc ctattccgaa gttcctattc tctagaaagt    4440
ataggaactt catgcatggc ctccgcgccg gttttggcg cctcccgcgg gcgccccct    4500 cctcacggcg agcgctgcca cgtcagacga agggcgcagc gagcgtcctg atccttccgc    4560
ccggacgctc aggacagcgg cccgctgctc ataagactcg gccttagaac cccagtatca    4620
gcagaaggac atttttaggac gggacttggg tgactctagg cactggtttt ctttccaga    4680 gagcggaaca ggcgaggaaa agtagtccct tctcggcgat tctgcggagg gatctccgtg    4740
gggcggtgaa cgccgatgat tatataagga cgcgccgggt gtggcacagc tagttccgtc    4800
gcagccggga tttgggtcgc ggttcttgtt tgtggatcgc tgtgatcgtc acttggtgag    4860
tagcgggctg ctgggctggc cggggctttc gtggccgccg ggccgctcgg tgggacggaa    4920
gcgtgtggag agaccgccaa gggctgtagt ctgggtccgc gagcaaggtt gccctgaact    4980
gggggttggg gggagcgcag caaaatggcg gctgttcccg agtcttgaat ggaagacgct    5040
tgtgaggcgg gctgtgaggt cgttgaaaca aggtgggggg catggtgggc ggcaagaacc    5100
caaggtcttg aggccttcgc taatgcggga aagctcttat tcgggtgaga tgggctgggg    5160
caccatctgg ggaccctgac gtgaagtttg tcactgactg gagaactcgg tttgtcgtct    5220
gttgcggggg cggcagttat ggcggtgccg ttgggcagtg cacccgtacc tttgggagcg    5280
cgcgccctcg tcgtgtcgtg acgtcacccg ttctgttggc ttataatgca gggtggggcc    5340
acctgccggt aggtgtgcgg taggcttttc tccgtcgcag gacgcagggt tcgggcctag    5400
ggtaggctct cctgaatcga caggcgccgg acctctggtg aggggaggga taagtgaggc    5460
gtcagtttct ttggtcggtt ttatgtacct atcttcttaa gtagctgaag ctccggtttt    5520
gaactatgcg ctcggggttg gcgagtgtgt tttgtgaagt tttttaggca cctttgaaa    5580 tgtaatcatt tgggtcaata tgtaattttc agtgttagac tagtaaattg tccgctaaat    5640
tctggccgtt tttggctttt ttgttagacg tgttgacaat taatcatcgg catagtatat    5700
```

```
cggcatagta taatacgaca aggtgaggaa ctaaaccatg ggatcggcca ttgaacaaga    5760
tggattgcac gcaggttctc cggccgcttg ggtggagagg ctattcggct atgactgggc    5820
acaacagaca atcggctgct ctgatgccgc cgtgttccgg ctgtcagcgc aggggcgccc    5880
ggttcttttt gtcaagaccg acctgtccgg tgccctgaat gaactgcagg acgaggcagc    5940
gcggctatcg tggctggcca cgacgggcgt tccttgcgca gctgtgctcg acgttgtcac    6000
tgaagcggga agggactggc tgctattggg cgaagtgccg gggcaggatc tcctgtcatc    6060
tcaccttgct cctgccgaga agtatccat catggctgat gcaatgcggc ggctgcatac    6120
gcttgatccg gctacctgcc cattcgacca ccaagcgaaa catcgcatcg agcgagcacg    6180
tactcggatg gaagccggtc ttgtcgatca ggatgatctg gacgaagagc atcagggct    6240 cgcgccagcc gaactgttcg ccaggctcaa ggcgcgcatg cccgacggcg atgatctcgt    6300
cgtgacccat ggcgatgcct gcttgccgaa tatcatggtg gaaaatggcc gcttttctgg    6360
attcatcgac tgtggccggc tgggtgtggc ggaccgctat caggacatag cgttggctac    6420
ccgtgatatt gctgaagagc ttggcggcga atgggctgac cgcttcctcg tgctttacgg    6480
tatcgccgct cccgattcgc agcgcatcgc cttctatcgc cttcttgacg agttcttctg    6540
aggggatccg ctgtaagtct gcagaaattg atgatctatt aaacaataaa gatgtccact    6600
aaaatggaag ttttcctgt catactttgt taagaagggt gagaacagag tacctacatt    6660
ttgaatggaa ggattggagc tacggggtg gggtggggt gggattagat aaatgcctgc    6720
tctttactga aggctcttta ctattgcttt atgataatgt tcatagttg gatatcataa    6780 tttaaacaag caaaaccaaa ttaagggcca gctcattcct cccactcatg atctatagat    6840
ctatagatct ctcgtgggat cattgttttt ctcttgattc ccactttgtg gttctaagta    6900 ctgtggttc caaatgtgtc agtttcatag cctgaagaac gagatcagca gcctctgttc    6960
cacatacact tcattctcag tattgttttg ccaagttcta attccatcag acctcgacct    7020
gcagccccta gtcgacgaag ttcctattcc gaagttccta ttctctagaa agtataggaa    7080
cttcgctagc taaaattgga gggacaagac ttcccacaga ttttcggttt tgtcgggaag    7140
ttttttaata ggggcaaata aggaaaatgg gaggataggt agtcatctgg ggttttatgc    7200
agcaaaacta caggttatta ttgcttgtga tccgc                              7235
```

<210> SEQ ID NO 60
<211> LENGTH: 1499
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(172)
<223> OTHER INFORMATION: Mouse Upstream Sequence
<220> FEATURE:
<221> NAME/KEY: misc_feature
<222> LOCATION: (300)..(333)
<223> OTHER INFORMATION: LoxP
<220> FEATURE:
<221> NAME/KEY: misc_feature
<222> LOCATION: (379)..(1098)
<223> OTHER INFORMATION: eGFP
<220> FEATURE:
<221> NAME/KEY: misc_feature
<222> LOCATION: (1133)..(1354)
<223> OTHER INFORMATION: SV40 Poly(A)
<220> FEATURE:
<221> NAME/KEY: misc_feature
<222> LOCATION: (1355)..(1499)
<223> OTHER INFORMATION: Mouse Downstream Sequence

```
<400> SEQUENCE: 60
ctgcagtgga gtaggcgggg agaaggccgc acccttctcc ggaggggga ggggagtgtt      60 gcaataccTT tctgggagtt ctctgctgcc tcctggcttc tgaggaccgc cctgggcctg    120
ggagaatccc ttcccctct tccctcgtga tctgcaactc cagtctttct agttgaccag    180
ctcggcggtg acctgcacgt ctagggcgca gtagtccagg gtttccttga tgatgtcata    240
cttatcctgt cccttttttt tccacagggc gcgccactag tggatccgga acccttaata    300
taacttcgta taatgtatgc tatacgaagt tattaggtcc ctcgacctgc agcccaagct    360
agtgcccggg ccgccaccat ggtgagcaag ggcgaggagc tgttcaccgg ggtggtgccc    420
atcctggttg agctggacgg cgacgtaaac ggccacaagt tcagcgtgtc cggcgagggc    480
gagggcgatg ccacctacgg caagctgacc ctgaagttca tctgcaccac cggcaagctg    540
cccgtgccct ggcccaccct cgtgaccacc ctgacctacg gcgtgcagtg cttcagccgc    600
taccccgacc acatgaagca gcacgacttc ttcaagtccg ccatgcccga aggctacgtc    660
caggagcgca ccatcttctt caaggacgac ggcaactaca agacccgcgc cgaggtgaag    720
ttcgagggcg acaccctggt gaaccgcatc gagctgaagg gcatcgactt caaggaggac    780
ggcaacatcc tggggcacaa gctggagtac aactacaaca gccacaacgt ctatatcatg    840
gccgacaagc agaagaacgg catcaaggtg aacttcaaga tccgccacaa catcgaggac    900
ggcagcgtgc agctcgccga ccactaccag cagaacaccc ccatcggcga cggccccgtg    960
ctgctgcccg acaaccacta cctgagcacc cagtccgccc tgagcaaaga ccccaacgag   1020
aagcgcgatc acatggtcct gctggagttc gtgaccgccg ccgggatcac tctcggcatg   1080
gacgagctgt acaagtaata attctagagt cggggcggcc ggccgcttcg agcagacatg   1140
ataagataca ttgatgagtt tggacaaacc acaactagaa tgcagtgaaa aaaatgcttt   1200
atttgtgaaa tttgtgatgc tattgcttta tttgtaacca ttataagctg caataaacaa   1260
gttaacaaca acaattgcat tcattttatg tttcaggttc aggggggagg tgtgggaggtt   1320 ttttaaagca gtaaaaacct ctacaaatgt ggtactcgag taaaattgga gggacaagac   1380
ttcccacaga ttttcggttt tgtcgggaag tttttttaata ggggcaaata aggaaaatgg   1440
gaggataggt agtcatctgg ggttttatgc agcaaaacta caggttatta ttgcttgtg    1499
```